(12) United States Patent
Srinivasan et al.

(10) Patent No.: US 10,690,651 B2
(45) Date of Patent: Jun. 23, 2020

(54) SMALL MOLECULE METABOLITES FOR THE DIAGNOSIS OF BACTERIAL VAGINOSIS AND ASSESSMENT OF DISEASE RISK

(71) Applicant: Fred Hutchinson Cancer Research Center, Seattle, WA (US)

(72) Inventors: Sujatha Srinivasan, Redmond, WA (US); David N. Fredricks, Seattle, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 15/566,240

(22) PCT Filed: Apr. 13, 2016

(86) PCT No.: PCT/US2016/027266
§ 371 (c)(1),
(2) Date: Oct. 13, 2017

(87) PCT Pub. No.: WO2016/168284
PCT Pub. Date: Oct. 20, 2016

(65) Prior Publication Data
US 2018/0113109 A1 Apr. 26, 2018

Related U.S. Application Data

(60) Provisional application No. 62/146,867, filed on Apr. 13, 2015.

(51) Int. Cl.
*C12Q 1/00* (2006.01)
*G01N 33/487* (2006.01)
*C12Q 1/689* (2018.01)
*G01N 33/68* (2006.01)
*C12Q 1/06* (2006.01)
*C12Q 1/68* (2018.01)

(52) U.S. Cl.
CPC ............ *G01N 33/487* (2013.01); *C12Q 1/06* (2013.01); *C12Q 1/689* (2013.01); *G01N 33/6812* (2013.01); *C12Q 1/68* (2013.01); *C12Q 2600/112* (2013.01); *G01N 2570/00* (2013.01); *G01N 2800/36* (2013.01); *G01N 2800/56* (2013.01)

(58) Field of Classification Search
CPC .................................................... G01N 33/487
See application file for complete search history.

(56) References Cited

U.S. PATENT DOCUMENTS

2014/0220572 A1 8/2014 Mastroeni et al.
2018/0080057 A1* 3/2018 Reid .......................... C12P 7/42

OTHER PUBLICATIONS

Yeoman et al., A Multi-Omic System-Based Approach Reveals Metabolic Markers of Bacterial Vaginosis and Insight into the Disease, PLOS One, Feb. 2013, vol. 8, No. 2; Author's Manuscript used pp. 1-18; p. 3, col. 2, para 41; Pasge 6, col. 1, para 2; p. 10, col. 2, para 1-4 Table 4; p. 12, col. 1, para 3; p. 13, col. 2, para 1; p. 15, col. 2, para 3.
Wood et al., Methylotrophic Bacteria in Trimethylaminuria and Bacterial Vaginosis, Handbook of Hydrocrbon and Lipid Microbiology, 2010, pp. 3227-3240; p. 3236, para 4.
Laghi et al., Rifaximin Modulates the Vaginal Microbiome and Metabolome in Women Affected by Bacterial Vaginosis, Antimicrobial Agents and Chemotherapy, Jun. 2014, vol. 58, No. 6, pp. 3411-3420; p. 3416, col. 1, para 2.
Ison et al., "Non-volatile fatty acids in the diagnosis of non-specific vaginitis," *J Clin Pathol* 36:1367-1370, 1983.
Sobel, "Bacterial vaginosis," *Annu. Rev. Med.* 51:349-356, 2000.
Spiegel, "Bacterial Vaginosis," *Clinical Microbiology Reviews* 4(4):485-502, 1991.
Witkin et al., "Complexities of the Uniquely Human Vagina," *Sci Transl Med* 4(132):1-4, 2012 (5 pages).
Fredricks et al., "Molecular Identification of Bacteria Associated with Bacterial Vaginosis," *N Engl J Med* 353(18):1899-1911, 2005.
Ravel et al., "Vaginal microbiome of reproductive age-women," *PNAS* 108(Suppl. 1):4680-4687, 2011.
Srinivasan et al., "Bacterial Communities in Women with Bacterial Vaginosis: High Resolution Phylogenetic Analyses Reveal Relationships of Microbiota to Clinical Criteria," *PLoS One* 7(6):e37818, 2012 (15 pages).
Koumans et al., "The Prevalence of Bacterial Vaginosis in the United States, 2001-2004; Associations with Symptoms, Sexual Behaviors, and Reproductive Health," *Sexually Transmitted Diseases* 34(11):864-869, 2007.
Cherpes et al., "Association between Acquisition of Herpes Simplex Virus Type 2 in Women and Bacterial Vaginosis," *Clinical Infectious Diseases* 37:319-325, 2003.
Schwebke et al., "Risk Factors for Bacterial Vaginosis in Women at High Risk for Sexually Transmitted Diseases," *Sexually Transmitted Diseases* 32(11):654-658, 2005.
Taha et al., "Bacterial vaginosis and disturbances of vaginal flora: association with increased acquisition of HIV," *AIDS* 12:1699-1706, 1998.
Cohen et al., "Bacterial Vaginosis Associated with Increased Risk of Female-to-Male HIV-1 Transmission: A Prospective Cohort Analysis among African Couples," *PLoS Medicine* 9(6):e1001251, 2012 (9 pages).
Hillier et al., "The Role of Bacterial Vaginosis and Vaginal Bacteria in Amniotic Fluid Infection in Women in Preterm Labor with Intact Fetal Membranes," *Clin Infect Dis* 20(Suppl 2):S276-S278, 1995.
Haggerty et al., "Bacterial Vaginosis and Anaerobic Bacteria Are Associated with Endometritis," *Clinical Infectious Diseases* 39:990-995, 2004.

(Continued)

*Primary Examiner* — Albert M Navarro
(74) *Attorney, Agent, or Firm* — Seed Intellectual Property Law Group LLP

(57) ABSTRACT

The invention disclosed herein generally relates to methods and kits for diagnosing, assessing disease risk, treating, and preventing bacterial vaginosis (BV) and associated conditions. Additional embodiments include methods for developing metabolic profiles associated with increased disease risk, and developing new approaches to treat BV based on interrupting metabolic networks.

18 Claims, 13 Drawing Sheets
Specification includes a Sequence Listing.

(56) References Cited

OTHER PUBLICATIONS

Marrazzo et al., "Risk Factors for Cervicitis among Women with Bacterial Vaginosis," *JID* 193:617-624, 2006.
Hummelen et al., "Deep Sequencing of the Vaginal Microbiota of Women with HIV," *PLoS ONE* 5(8):e12078, 2010 (9 pages).
Nugent et al., "Reliability of Diagnosing Bacterial Vaginosis Is Improved by a Standardized Method of Gram Stain Interpretation," *Journal of Clinical Microbiology* 29(2):297-301, 1991.
Chen et al., "Amine Content of Vaginal Fluid from Untreated and Treated Patients with Nonspecific Vaginitis," *J. Clin. Invest.* 63:828-835, 1979.
Sobel et al., "Diagnosing vaginal infections through measurement of biogenic amines by ion mobility spectrometry," *European Journal of Obstetrics of Gynecology and Reproductive Biology* 163:81-84, 2012.
Wolrath et al., "Analysis of Bacterial Vaginosis-Related Amines in Vaginal Fluid by Gas Chromatography and Mass Spectrometry," *Journal of Clinical Microbiology* 39(11):4026-4031, 2001.
Chen et al., "Biochemical Diagnosis of Vaginitis: Determination of Diamines in Vaginal Fluid," *The Journal of Infectious Diseases* 145(3):337-345, 1982.
Brand et al., "Trimethylamine: The Substance Mainly Responsible for the Fishy Odor Often associated with bacterial vaginosis," *Obstet Gynecol* 68:682-685, 1986.
Giacomini et al., "Accuracy of Cervical/Vaginal Cytology in the Diagnosis of Bacterial Vaginosis," *Sexually Transmitted Diseases* 25(1):24-27, 1998.
Pheifer et al., "Nonspecific vaginitis: Role of Haemophilus vaginalis and Treatment with Metronidazole," *N Engl J Med* 298(26):1429-1434, 1978.
Fredricks et al., "Targeted PCR for Detection of Vaginal Bacteria Associated with Bacterial Vaginosis," 45(10):3270-3276, 2007.
Marrazzo et al., "Relationship of Specific Vaginal Bacteria and Bacterial Vaginosis Treatment Failure in Women Who Have Sex with Women: A Cohort Study," *Ann Intern Med* 149(1):20-28, 2008 (NIH Public Access Author Manuscript, available in PMC Jan. 26, 2009)(16 pages).
Abubucker et al., "Metabolic Reconstruction for Metagenomic Data and Its Application to the Human Microbiome," *PLoS Computational Biology* 8(6):e1002358, 2012 (17 pages).
Gajer et al., "Temporal Dynamics of the Human Vaginal Microbiota," *Sci Transl Med* 4(132):132ra52, 2012 (NIH Public Access Author Manuscript, available in PMC Jul. 25, 2013)(21 pages).
Wolrath et al., "Trimethylamine content in vaginal secretion and its relation to bacterial vaginosis" *AMPIS* 110:819-824, 2002.
Mendes-Soares et al., "Comparative Functional Genomics of *Lactobacillus* spp. Reveals Possible Mechanisms for Specialization of Vaginal Lactobacilli to Their Environment," *Journal of Bacteriology* 196(7):1458-1470, 2014.
Macklaim et al., "At the crossroads of vaginal health and disease, the genome sequence of Lactobacillus iners AB-1," *PNAS* 108(1):4688-4695, 2011.
Kurihara et al., "A Putrescine-Inducible Pathway Comprising PuuE-YneI in Which γ-Aminobutyrate Is Degraded into Succinate in *Escherichia coli* K-12," *Journal of Bacteriology* 192(18):4582-4591, 2010.
Kurihara et al., "A Novel Putrescine Utilization Pathway Involves γ-Glutamylated Intermediates of *Escherichia coli* K-12," *The Journal of Biological Chemistry* 280(6):4602-4608, 2005.
Koeth et al., "Intestinal microbiota metabolism of L-carnitine, a nutrient in red meat, promotes atherosclerosis," *Nat Med.* 19(5):576-585, 2013 (HHS Public Access Author manuscript, available in PMC Nov. 1, 2013)(28 pages).
Cunningham et al., "Proinflammatory Properties of Unsaturated Fatty Acids and Their Monohydroxy Metabolites," *Prostaglandins* 30(3):497-509, 1985.
Stoltz et al., "Effect of Metabolic Inhibitors on Arachidonic Acid Metabolism in the Corneal Epithelium: Evidence for Cytochrome P450-Mediated Reactions," *Journal of Ocular Pharmacology* 10(1):307-317, 1994.

Spector, "Essentiality of Fatty Acids," *Lipids* 43:S1-3, 1999.
Hillier et al., "Association Between Bacterial Vaginosis and Preterm Delivery of a Low-Birth-Weight Infant," *N Engl J Med* 333:1737-1742, 1995.
Klebanoff et al., "Is bacterial vaginosis a stronger risk factor for preterm birth when it is diagnosed earlier in gestation?," *American Journal of Obstetrics and Gynecology* 192:470-477, 2005.
Holmes et al., "Vaginal Redox Potential in Bacterial Vaginosis (Nonspecific Vaginitis)," *The Journal of Infectious Diseases* 152(2):379-382, 1985.
Kemp et al., "Non-equilibrium thermodynamics of thiol/disulfide redox systems: A perspective on redox systems biology," *Free Radic Biol Med* 44(6):921-937, 2008 (NIH Public Access Author Manuscript, available in PMC Mar. 15, 2009)(30 pages).
Circu et al., "Redox biology of the intestine," *Free Radic Res* 45(11-12):1245-1266, 2011 (NIH Public Access Author Manuscript, available in PMC Nov. 1, 2012)(35 pages).
Henkel, "Leukocytes and oxidative stress: dilemma for sperm function and male fertility," *Asian Journal of Andrology* 13:43-52, 2011.
Lewis et al., "Degradation, Foraging, and Depletion of Mucus Sialoglycans by the Vagina-adapted Actinobacterium Gardnerella vaginalis," *The Journal of Biological Chemistry* 288(17):12067-12079, 2013.
Briselden et al., "Sialidases (Neuraminidases) in Bacterial Vaginosis and Bacterial Vaginosis-Associated Microflora," *Journal of Clinical Microbiology* 30(3):663-666, 1992.
Cauci et al., "High sialidase levels increase preterm birth risk among women who are bacterial vaginosis-positive early gestation," *Am J Obstet Gynecol* 204(142):e1-e9, 2011.
McGregor et al., "Bacterial vaginosis is associated with prematurity and vaginal fluid mucinase and sialidase: Results of a controlled trial of topical clindamycin cream," *Am J Obstet Gynecol* 170:1048-1060, 1994.
Olmsted et al., "Glycosidase and Proteinase Activity of Anaerobic Gram-Negative Bacteria Isolated from Women With Bacterial Vaginosis," *Sexually Transmitted Diseases* 30(3):257-261, 2003.
Myziuk et al., "BVBlue Test for Diagnosis of Bacterial Vaginosis," *Journal of Clinical Microbiology* 41(5):1925-1928, 2003.
Wiggins et al., "Use of 5-Bromo-4-Chloro-3-Indolyl-α-D-N-Acetylneuraminic Acid in a Novel Spot Test to Identify Sialidase Activity in Vaginal Swabs from Women with Bacterial Vaginosis," *Journal of Clinical Microbiology* 38(8):3096-3097, 2000.
Cauci et al., "Vaginal hydrolytic enzymes, immunoglobulin A against Gardnerella vaginalis toxin, and risk of early preterm birth among women in preterm labor with bacterial vaginosis or intermediate flora," *Am J Obstet Gynecol* 187(4):877-881, 2002.
Cauci et al., "Determination of Immunoglobulin A against Gardnerella vaginalis Hemolysin, Sialidase, and Prolidase Activities in Vaginal Fluid: Implications for Adverse Pregnancy Outcomes," *J Clin Microbiol* 41(1):435-438, 2003.
Moran et al., "Sweet-talk: role of host glycosylation in bacterial pathogenesis of the gastrointestinal tract," *Gut* 60:1412-1425, 2011.
Slomiany et al., "Salivary Mucins in Oral Mucosal Defense," *Gen. Pharmac.* 27(5):761-771, 1996.
Greiner et al., "Nontypeable Haemophilus infleunzae Strain 2019 Produces a Biofilm Containing N-Acetylneuraminic Acid That May Mimic Sialylated O-Linked Glycans," *Infection and Immunity* 72(7):4249-4260, 2004.
Srinivasan et al., "The Human Vaginal Bacterial Biota and Bacterial Vaginosis," *Interdisciplinary Perspectives on Infectious Diseases* 2008(750479):1-22, 2008 (23 pages).
Swidsinski et al., "Adherent Biofilms in Bacterial Vaginosis," *Obstetrics & Gynecology* 106(5):1013-1023, 2005.
Swidsinski et al., "An adherent Gardnerella vaginalis biofilm persists on the vaginal epithelium after standard therapy with oral metronidazole," *Am J Obstet Gynecol* 197:1.e1-1.e6, 2007 (6 pages).
Khot et al., "Development and optimization of quantitative PCR for the diagnosis of invasive aspergillosis with bronchoalveolar lavage fluid," *BMC Infectious Diseases* 8(73): 2008 (13 pages).

(56) References Cited

OTHER PUBLICATIONS

Fredricks et al., "Changes in Vaginal Bacterial Concentrations with Intravaginal Metronidazole Therapy for Bacterial Vaginosis as Assessed by Quantitative PCR," *Journal of Clinical Microbiology* 47(3):721-726, 2009.

Srinivasan et al., "Temporal Variability of Human Vaginal Bacteria and Relationship with Bacterial Vaginosis," *PLoS ONE* 5(4):e10197, 2010 (8 pages).

Matsen et al., "pplacer: linear time maximum-likelihood and Bayesian phylogenetic placement of sequences onto a fixed reference tree," *BMC Bioinformatics* 11:538, 2010 (16 pages).

Evans et al., "Integrated, Nontargeted Ultrahigh Performance Liquid Chromatography/Electrospray Ionization Tandem Mass Spectrometry Platform for the Identification and Relative Quantification of the Small-Molecule Complement of Biological Systems," *Anal. Chem.* 81:6656-6667, 2009.

Lawton et al., "Analysis of the adult human plasma metabolome," *Pharmacogenomics* 9(4):383-397, 2008.

Ohta et al., "Untargeted Metabolomic Profiling as an Evaluative Tool of Fenofibrate-Induced Toxicology in Fischer 344 Male Rats," *Toxicologic Pathology* 37:521-535, 2009.

Friedman et al., "Regularization Paths for Generalized Linear Models via Coordinate Descent," *J. Stat Softw* 33(1):1-22, 2010 (NIH Public Access Author Manuscript, available in PMC Aug. 30, 2010)(20 pages).

\* cited by examiner

Metabolites negatively associated with BV clinical criteria

SEQUENCE LISTING

```
<160> NUMBER OF SEQ ID NOS: 12

<210> SEQ ID NO 1
<211> LENGTH: 21
<212> TYPE: DNA
<213> ORGANISM: Eggerthella-like bacteria

<400> SEQUENCE: 1
gaccaacctg cctcttacat t                                            21

<210> SEQ ID NO 2
<211> LENGTH: 22
<212> TYPE: DNA
<213> ORGANISM: Eggerthella-like bacteria

<400> SEQUENCE: 2
gcatacatca tgtgatatgt gc                                           22

<210> SEQ ID NO 3
<211> LENGTH: 24
<212> TYPE: DNA
<213> ORGANISM: Eggerthella-like bacteria

<400> SEQUENCE: 3
aaaagaaatt ctggctaata ccaa                                         24

<210> SEQ ID NO 4
<211> LENGTH: 17
<212> TYPE: DNA
<213> ORGANISM: Prevotella buccalis

<400> SEQUENCE: 4
gcgcgacgtg tcgtgca                                                 17

<210> SEQ ID NO 5
<211> LENGTH: 17
<212> TYPE: DNA
<213> ORGANISM: Prevotella buccalis

<400> SEQUENCE: 5
ccggttgagc cggtaca                                                 17

<210> SEQ ID NO 6
<211> LENGTH: 18
<212> TYPE: DNA
<213> ORGANISM: Prevotella buccalis

<400> SEQUENCE: 6
cgccagrtaa gcgtgttg                                                18

<210> SEQ ID NO 7
<211> LENGTH: 22
<212> TYPE: DNA
<213> ORGANISM: Prevotella timonensis
```

```
<400> SEQUENCE: 7
gagcgtaggc tgtctattaa gc                                           22

<210> SEQ ID NO 8
<211> LENGTH: 22
<212> TYPE: DNA
<213> ORGANISM: Prevotella timonensis

<400> SEQUENCE: 8
cttcctgcat actcaagtcg ac                                           22

<210> SEQ ID NO 9
<211> LENGTH: 21
<212> TYPE: DNA
<213> ORGANISM: Prevotella timonensis

<400> SEQUENCE: 9
atttaccggc tcaaccggtg g                                            21

<210> SEQ ID NO 10
<211> LENGTH: 24
<212> TYPE: DNA
<213> ORGANISM: Prevotella amnii

<400> SEQUENCE: 10
ggcttgaatt gcagatgttt atat                                         24

<210> SEQ ID NO 11
<211> LENGTH: 21
<212> TYPE: DNA
<213> ORGANISM: Prevotella amnii

<400> SEQUENCE: 11
ccatgcagca ccttcacaaa t                                            21

<210> SEQ ID NO 12
<211> LENGTH: 20
<212> TYPE: DNA
<213> ORGANISM: Prevotella amnii

<400> SEQUENCE: 12
agatgatata ttcccttcgg                                              20
```

SMALL MOLECULE METABOLITES FOR THE DIAGNOSIS OF BACTERIAL VAGINOSIS AND ASSESSMENT OF DISEASE RISK

CROSS-REFERENCE TO RELATED APPLICATIONS

The present application is a U.S. National Stage entry under 35 U.S.C. § 371 of International Application No. PCT/US2016/027266, filed on Apr. 13, 2016, which claims priority to U.S. Provisional Application No. 62/146,867 filed on Apr. 13, 2015, each of which is incorporated by reference in its entirety.

GOVERNMENT SUPPORT

This invention was made with government support under AI061628 and HG005816 awarded by the National Institutes of Health. The government has certain rights in the invention.

FIELD OF THE INVENTION

The invention disclosed herein generally relates to methods and kits for diagnosing, assessing disease risk, treating, and preventing bacterial vaginosis (BV) and associated conditions. Additional embodiments include methods for developing metabolic profiles associated with increased disease risk, and developing new approaches to treat BV based on interrupting metabolic networks.

BACKGROUND

Bacterial vaginosis (BV) is a common but highly enigmatic condition that is associated with adverse outcomes for women and their neonates. BV is characterized by shifts in the vaginal microbiota from *Lactobacillus* dominant to a microbiota with diverse anaerobic bacteria. Small molecule metabolites in the vagina influence host physiology, affect microbial community composition, and impact risk of adverse health outcomes.

The composition of small molecule metabolites in the human vagina is largely shaped by bacterial metabolism of human derived nutrients. These bacterial metabolites may impact human cell function, inflammation, and disease susceptibility. However, few studies have comprehensively examined the associations between vaginal bacteria and metabolites, and no study has used quantitative PCR to link concentrations of fastidious vaginal bacteria to metabolite concentrations. Individual metabolites associated with BV status have been identified and shown to be useful markers of BV such as lactate (no BV) and succinate (BV) (1-7). However, there are hundreds of other compounds that have not been identified in vaginal fluid and linked to particular bacterial communities or clinical outcomes.

The composition of the human vaginal microbiota ranges from communities dominated by a limited of *Lactobacillus* species to complex communities of diverse anaerobes, most evident with the common condition BV (8-11). BV affects up to 29% of women in the United States (12), and has been associated with several adverse reproductive and health outcomes including elevated risks for acquisition of sexually transmitted infections (13-15), transmission of HIV to male sex partners (16), preterm birth (17), pelvic inflammatory disease (18), and cervicitis (19). The microbiota in BV is heterogeneous; different groups of women have vaginal microbiotas dominated with different bacteria such as BV-associated bacterium-1 (BVAB1), *Leptotrichia/Sneathia* species, *Prevotella* spp., *Gardnerella vaginalis*, or *Lactobacillus iners*, while others are colonized with diverse bacteria and no single dominant bacterium (11, 20). BV is diagnosed in clinical settings using Amsel criteria in which a set of four signs or symptoms are evaluated, with at least three required for a diagnosis of BV (21). Different bacteria are correlated with each of these four clinical criteria (11). Small molecule metabolites can affect at least three of these clinical criteria including vaginal discharge, pH, and amine odor. The diagnosis of BV can also be made using Gram stain interpretation of vaginal fluid smears with enumeration of bacterial morphotypes (22).

Polyamines such as putrescine and cadaverine are found in women with BV and contribute to the fishy amine odor in this condition (1, 23-25). These polyamines are likely produced from decarboxylation of amino acids mediated by bacteria (23). Chen et al. demonstrated that in vitro production of polyamines by mixed anaerobic vaginal bacteria was inhibited in the presence of metronidazole, suggesting a role for bacterial production of polyamines (26). Likewise, trimethylamine has a fishy odor, is found in women with BV, and is also thought to be a product of bacterial metabolism (27). These amines become volatile when pH is elevated, a property utilized in the clinical diagnosis of BV when employing the "whiff test" (4, 28, 29). The amine odor can also be noted in vivo with elevated pH during menses and after vaginal intercourse with men, as the pH of blood and semen are close to 7 leading to enhanced volatilization. It has been suggested that the amines are associated with increased vaginal transudation of fluid and squamous cell exfoliation, resulting in the thin homogeneous grayish-white discharge that is typically associated with BV (4).

Mass spectrometry (when coupled with chromatography) offers the opportunity to measure small molecule metabolites in the vagina, and assign identity to hundreds of compounds simultaneously. One recent study described the metabolite profiles in eight women with BV using this approach, and classified these women in to two groups based on their vaginal metabolite compositions (30). Additional insights into the functions of these bacterial consortia can be gained by linking bacterial community composition and concentrations of bacteria to metabolic signatures.

Current methods of diagnosing BV have numerous disadvantages. Most common methods of diagnosing BV and their disadvantages currently include: (1) Clinical settings: Amsel clinical criteria which include a set of four signs or symptoms of which at least three are required for a positive diagnosis. These include pH, a positive "whiff test," greater than 20% clue cells (vaginal epithelial cells coated with bacteria) and a thin homogeneous discharge. This diagnostic procedure requires a trained clinician and a microscope is needed to evaluate clue cells; (2) Research settings: Vaginal fluid Gram stains and evaluation of the morphotypes based on the Nugent method or variations of the Ison & Hay method. The Nugent method is the gold standard in research settings, however, a highly trained microscopist is needed for evaluating the slides; (3) Detection of bacterial nucleic acids: Gen-Probe has developed a test targeting bacterial nucleic acids from bacteria that cause BV. Testing nucleic acids by PCR is typically expensive. Becton Dickinson has a BD Affirm VPIII system that can detect high levels of *Gardnerella vaginalis* DNA. However, *G. vaginalis* is not specific for the diagnosis of BV, as it is present in 70% of women without BV; (4) Detection of bacterial sialidase: OSOM BVBlue test that measures bacterial sialidases that are elevated in BV. While one study showed that the test was sensitive and specific (Bradshaw et al., 2005 JCM 43:1304-1308), other studies have not been able to demonstrate high sensitivity (Madhivanan et al., 2014 Infect Dis Obstet Gynecol Article ID 908313; Hillier https://clinicaltrials.gov/ct2/show/results/NCT00682851?sect=X01256.)

Thus there is a need for improved methods and kits for diagnosing, assessing disease risk, treating, and preventing BV and associated conditions.

SUMMARY

The present invention describes methods and kits for diagnosing, assessing disease risk, treating and preventing BV and associated conditions.

The method for diagnosing BV in a subject can include collecting a sample from the subject, assessing a small molecule metabolomic profile of a metabolomic signature by measuring levels of at least two indicative metabolites, and comparing the metabolomic profile with a diagnostic metabolomic profile of the signature. A substantial match between the metabolomic profile and the diagnostic metabolomic profile can be indicative of BV.

The method for monitoring disease progression of BV can include collecting a first sample from the subject; assessing a small molecule metabolomic profile of a metabolomic signature by measuring levels of at least two indicative metabolites; comparing the metabolomic profile with a diagnostic metabolomic profile of the signature; collecting a second sample from the subject; assessing a small molecule metabolomic profile of a metabolomic signature in the second sample by measuring levels of at least two indicative metabolites; and comparing the metabolomic profile with a diagnostic metabolomic profile of the signature. The disease progression can be based on substantial matches between the metabolomic profiles and the diagnostic metabolomic profiles. The second sample can be collected after a period of time from the first sample. The period of time can be at least three days.

The methods can include Chromatographic separation and/or mass spectroscopy. The substantial match can be at least 80%.

A kit for diagnosing BV in a subject in which the diagnosis is made with a test apparatus and include reagents for collecting a test sample from a subject; and reagents for measuring the profile of a metabolomics profile by measuring levels of indicative metabolites.

The sample can be vaginal fluid or Cervicovaginal lavage fluid (CVL).

The indicative metabolites can include two or more metabolites selected from the group listed in Table 1.

The indicative metabolites can include lipids, amino acids, nucleotides, co-factors, vitamins, carbohydrates, energy molecules and redox molecules.

The indicative metabolites can include amino acids such as 5-Aminovaleric Acid, Cadaverine, D-Leucic Acid, Glutaric Acid, Histamine, N-Acetylputrescine, Putrescine, Tryptamine, Tyramine, Anthranilate, Arginine, Asparagine, Aspartic Acid, Creatine, Cysteine, Cystine, Glycine, Histidine, iso-Leucine, Leucine, Lysine, Methionine, MethylSuccinate, Ornithine, Phenylalanine, Pipecolate, Reduced glutathione, Serine, Threonine, Tryptophan, Tyrosine, Xanthurenate. The indicative metabolites can include fatty acids such as 13-HODE, 12-HETE, Glycerol-3-P, Arachidonate, Carnitine. The indicative metabolites can include nucleotides such as Oxypurinol, Uracil, Adenosine, AMP, Hypoxanthine, and Urate. The indicative metabolites can include carbohydrates such as Glyceraldehyde, N-Acetylneuraminate, PEP, F16BP/F26BP/G16BP, Glucoronate, Glucose, Glutamic acid, Lactate, Oxalic Acid, and Sorbitol.

BRIEF DESCRIPTION OF THE DRAWINGS

Those of skill in the art will understand that the drawings, described below, are for illustrative purposes only. The drawings are not intended to limit the scope of the present teachings in any way.

FIG. 9 depicts metabolite profiles in women with intermediate Nugent scores. Non-metric multi dimensional scaling (MDS) plot summarizing metabolite profiles in women with and without BV classified by Nugent score. The MDS plot was created using non-metric multi-dimensional scaling of Euclidean distance between log-transformed metabolite concentrations, and represented in 2-dimensional space. Green dots denote women with Nugent scores 0-3, purple dots indicate women with intermediate scores 4-6 and red dots show women with scores 7-10. Women with intermediate Nugent scores have metabolite profiles ranging from those that are similar to women without BV (Nugent 0-3) to profiles which are more BV-like.

FIG. 10 summarizes the log 2 fold change of CVL relative to swab as a function of average log 2 abundance. Of the 101 metabolites detected using the NW-MRC platform, no metabolite was detected only in swab samples.

DETAILED DESCRIPTION OF THE INVENTION

Figure 1:
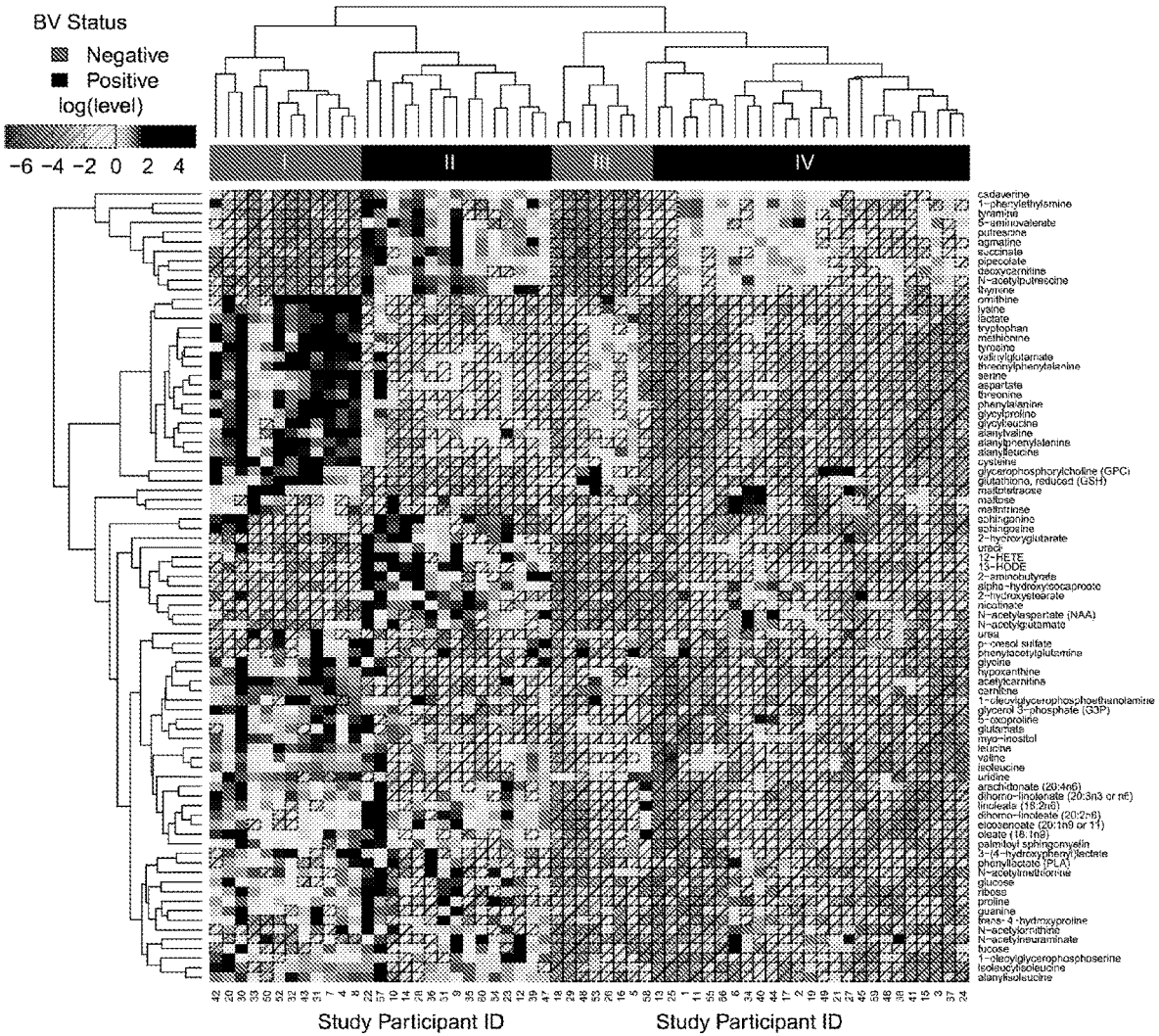
FIG. 1 is a dendrogram showing associations of 30% of most variable metabolites with BV status, determined using Amsel and Nugent criteria. Clustering of the metabolites resulted in four groups (Clusters I-IV). The clustering algorithm was not informed by BV status. Study participant IDs are provided on the x-axis and metabolites are listed on the y-axis. The heat map depicts log-transformed concentrations of the most variable metabolites between the clusters. Values ranged from −6.956 to 4.818.

Unless otherwise noted, terms are to be understood according to conventional usage by those of ordinary skill in the relevant art.

The present invention relates to methods and kits for diagnosing, assessing disease risk, treating and preventing BV and associated conditions.

In some embodiments, the invention relates to a method of diagnosing bacterial vaginosis (BV) in a subject including the steps of collecting a sample from the subject; assessing a small molecule metabolomic profile of a metabolomic signature by measuring levels of metabolites; comparing the metabolomic profile with a diagnostic metabolomic profile of the signature. In some embodiments, a substantial match between the metabolomic profile and the diagnostic metabolomic profile is indicative of bacterial vaginosis.

In some embodiments, the invention relates to a method of monitoring disease progression of BV in a subject including the steps of: collecting a first sample from the subject; assessing a small molecule metabolomic profile of a metabolomic signature by measuring levels of metabolites; comparing the metabolomic profile with a diagnostic metabolomic profile of the signature; wherein the disease progression is based at least in part upon a substantial match between the metabolomic profile and the diagnostic metabolomic profile; collecting a second sample from the subject; assessing a small molecule metabolomic profile of a metabolomic signature by measuring levels of metabolites; comparing the metabolomic profile with a diagnostic metabolomic profile of the signature; wherein the disease progression is based at least in part upon a substantial match between the metabolomic profile and the diagnostic metabolomic profile; wherein the disease progression is based at least in part upon a substantial match between the metabolomic profile and the diagnostic metabolomic profile; wherein the second sample is collected after a period of time from the first sample. The period of time can be 1 day, 2 days, 3 days, 4 days, 5 days, 6 days, 1 week, 2 weeks, 3 weeks, 1 month, 2 months 3 months, 4 months, 5 months or more.

In some embodiments, the invention relates to a kit for diagnosing BV in a subject in which the diagnosis is made with a test apparatus. The kit can include reagents for collecting a test sample from a subject; and reagents for measuring the profile of a metabolomics profile by measuring levels of metabolites.

In some embodiments, sample is vaginal fluid or Cervicovaginal lavage fluid (CVL).

In some embodiments, the metabolites include one or more metabolites selected from the group listed in Table 1. The method can include 1, 2, 3, 4, 5, 6, 7, 8, 9, 10, or more metabolites from the group listed in Table 1.

In some embodiments, the metabolites include one or more metabolites of lipids, amino acids, nucleotides, co-factors, vitamins, carbohydrates, energy molecules or redox molecules. In some embodiments, the metabolites include 1, 2, 3, 4, 5, 6, 7, 8, or all of lipids, amino acids, nucleotides, co-factors, vitamins, carbohydrates, energy molecules or redox molecules.

In some embodiments, the metabolites include one or more amino acids selected from 5-Aminovaleric Acid, Cadaverine, D-Leucic Acid, Glutaric Acid, Histamine, N-Acetylputrescine, Putrescine, Tryptamine, Tyramine, Anthranilate, Arginine, Asparagine, Aspartic Acid, Creatine, Cysteine, Cystine, Glycine, Histidine, iso-Leucine, Leucine, Lysine, Methionine, MethylSuccinate, Ornithine, Phenylalanine, Pipecolate, Reduced glutathione, Serine, Threonine, Tryptophan, Tyrosine, Xanthurenate, and the like. The method can include 0, 1, 2, 3, 4, 5, 6, 7, 8, 9, 10, 11, 12, 13, 14, 15, 16, 17, 18, 19 or more of these amino acids.

In some embodiments, the metabolites can include one or more fatty acids selected from 13-HODE, 12-HETE, Glycerol-3-P, Arachidonate, Carnitine, and the like. The method can include 0, 1, 2, 3, 4, or all of these fatty acids.

In some embodiments, the metabolites can include nucleotides selected from Oxypurinol, Uracil, Adenosine, AMP, Hypoxanthine, Urate, and the like. The method can include 0, 1, 2, 3, 4, 5, or all of these nucleotides.

In some embodiments, the metabolites can include carbohydrates selected from Glyceraldehyde, N-Acetylneuraminate, PEP, F16BP/F26BP/G16BP, Glucoronate, Glucose, Glutamic acid, Lactate, Oxalic Acid, Sorbitol, and the like. The method can include 0, 1, 2, 3, 4, 5, 6, 7, 8, 9 or all of these carbohydrates.

In some embodiments, the a substantial match between the metabolomic profile and the diagnostic metabolomic profile is 50%, 60%, 70%, 80%, 90%, or more.

In some embodiments, the method comprises Chromatographic separation or mass spectroscopy, or both.

In some embodiments, the method includes pyrosequencing of the test sample. In some embodiments, the pyrosequencing targets the V3-V4 region of the 16S-rRNA gene.

TABLE 1

Heat map of statistically significant biochemicals profiled. For paired comparisons, asterisks indicate p≤0.05
** indicate that the mean values are significantly higher for that comparison;* indicates values that are significantly lower). Italicized text indicates 0.05 < p < 0.10.

| PATH-WAY SORT | SUPER PATH-WAY | SUB PATHWAY | BIOCHEMICAL NAME | PLAT-FORM | COMP ID | Fold Change Welch's Two-Sample t-Test Pos Neg | Statistical value Welch's Two-Sample t-Test Pos/Neg | | Mean Values | |
|---|---|---|---|---|---|---|---|---|---|---|
| | | | | | | | p-Value | q-Value | Neg | Pos |
| 1 | Amino acid | Glycine, serine and threonine metabolism | glycine | GC/MS | 11777 | 0.34* | <0.001 | 0.0000 | 3.739741 | 1.263827 |
| 2 | | | sarcosine (N-Methylglycine) | GC/MS | 1516 | 4.44** | <0.001 | 0.0000 | 0.427684 | 1.898044 |
| 7 | | | serine | GC/MS | 1648 | 0.20* | <0.001 | 0.0002 | 6.580896 | 1.285634 |
| 9 | | | N-acetylserine | LC/MS pos | 37076 | 0.41* | <0.001 | 0.007 | 1.707820 | 0.697719 |
| 16 | | | threonine | GC/MS | 1284 | 0.23* | <0.001 | 0.0002 | 5.900021 | 1.329807 |
| 17 | | | N-acetylthreonine | LC/MS neg | 33939 | 0.19* | <0.001 | 0.0000 | 3.111569 | 0.593361 |
| 21 | | | betaine | LC/MS pos | 3141 | 0.70* | 0.0243 | 0.0119 | 1.202041 | 0.844976 |
| 23 | | Alanine and aspartate metabolism | alanine | GC/MS | 1126 | 0.80 | 0.1348 | 0.0520 | 1.891140 | 1.513845 |
| 24 | | | beta-alanine | GC/MS | 55 | 1.62 | 0.2366 | 0.0857 | 0.810754 | 1.310248 |
| 26 | | | N-acetylalanine | LC/MS neg | 1585 | 2.18** | 0.0351 | 0.0165 | 0.915336 | 1.991908 |
| 29 | | | aspartate | GC/MS | 15996 | 0.22* | 0.0013 | 0.0009 | 5.004044 | 1.116333 |
| 31 | | | N-acetylaspartate (NAA) | LC/MS pos | 22185 | 6.21** | <0.001 | 0.0000 | 0.405221 | 2.517588 |
| 38 | | Glutamate metabolism | glutamate | LC/MS pos | 57 | 0.44* | 0.0072 | 0.0042 | 2.753214 | 1.204244 |
| 42 | | | glutamine | LC/MS pos | 53 | 0.56 | 0.1241 | 0.0485 | 1.649106 | 0.931688 |
| 43 | | | pyroglutamine* | LC/MS pos | 32672 | *0.75* | 0.0776 | 0.0329 | 1.288368 | 0.968558 |
| 44 | | | gamma-aminobutyrate (GABA) | GC/MS | 1416 | 0.02* | 0.0148 | 0.0077 | 81.695175 | 1.687678 |
| 45 | | | N-acetylglutamate | LC/MS pos | 15720 | 3.72** | <0.001 | 0.0000 | 0.556992 | 2.073273 |
| 48 | | Histidine metabolism | histidine | LC/MS neg | 59 | 0.02* | <0.001 | 0.0003 | 4.207027 | 0.836916 |
| 50 | | | urocanate | LC/MS pos | 607 | 0.68 | 0.8376 | 0.2431 | 1.282119 | 0.833274 |
| 53 | | | histamine | GC/MS | 1574 | 0.72 | 0.7823 | 0.2313 | 2.076850 | 1.486302 |
| 60 | | Lysine metabolism | cadaverine | GC/MS | 15308 | 27.38** | <0.001 | 0.0000 | 0.146588 | 4.012971 |
| 66 | | | lysine | GC/MS | 1301 | 0.08* | <0.001 | 0.0000 | 11.290963 | 0.915742 |
| 67 | | | 2-aminoadipate | GC/MS | 6146 | 1.04 | 0.2273 | 0.0827 | 1.358665 | 1.407328 |
| 69 | | | pipecolate | LC/MS pos | 1444 | 52.72** | <0.001 | 0.0000 | 0.070170 | 3.699688 |
| 74 | | | N6-acetylysine | LC/MS pos | 36752 | 5.70** | <0.001 | 0.0000 | 0.352662 | 2.009462 |
| 77 | | Phenylalanine & tyrosine | phenylactate (PLA) | LC/MS neg | 22130 | 2.24 | 0.5252 | 0.1668 | 1.685189 | 3.772378 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | | | | |
|---|---|---|---|---|---|---|---|---|---|
| 78 | metabolism | phenylalanine | LC/MS pos | 64 | 0.15* | <0.001 | 0.0000 | 4.537531 | 0.683247 |
| 79.5 | | Isobar: 1-phenylethanamine phenylethylamine | LC/MS pos | 38763 | 5.76** | <0.001 | 0.0000 | 4.475218 | 25.796219 |
| 80 | | phenylacetate | LC/MS neg | 15958 | 3.72** | <0.001 | 0.0001 | 0.175127 | 0.652184 |
| 82 | | p-cresol sulfate | LC/MS neg | 36103 | 0.68 | 0.5443 | 0.1721 | 1.931141 | 1.309778 |
| 90 | | tyrosine | LC/MS pos | 1299 | 0.11* | <0.001 | 0.0000 | 6.775518 | 0.747969 |
| 91 | | 3-(4-hydroxyphenyl)-lactate | LC/MS neg | 32197 | 0.54* | 0.0103 | 0.0056 | 3.235635 | 1.732232 |
| 94 | | tyramine | LC/MS pos | 1603 | 21.24** | <0.001 | 0.0000 | 0.333968 | 7.092416 |
| 106 | | 4-hydroxyphenylacetate | GC/MS | 541 | 51.37** | <0.001 | 0.0000 | 0.049353 | 2.535028 |
| 111 | | N-acetylphenylalanine | LC/MS neg | 33950 | 2.24** | 0.0222 | 0.0110 | 0.633846 | 1.421726 |
| 115 | | phenylacetylglutamine | LC/MS pos | 35126 | 0.54 | 0.1103 | 0.0441 | 2.078089 | 1.129685 |
| 118.5 | | 3-(4-hydroxyphenyl)-propionate | GC/MS | 39587 | 71.71** | <0.001 | 0.0000 | 0.037424 | 2.683498 |
| 119 | | 3-phenylpropionate (hydrocinnamate) | LC/MS neg | 15749 | 14.62** | <0.001 | 0.0002 | 0.119842 | 1.752567 |
| 121 | | phenol sulfate | LC/MS neg | 32553 | 0.80 | 0.7819 | 0.2313 | 0.985803 | 0.792313 |
| 124 | Tryptophan metabolism | kynurenate | LC/MS neg | 1417 | 1.43** | <0.001 | 0.0003 | 0.779062 | 1.115300 |
| 125 | | kynurenine | LC/MS pos | 15140 | 0.46* | 0.0058 | 0.0035 | 1.245910 | 0.571509 |
| 126 | | tryptophan | LC/MS pos | 54 | 0.19* | <0.001 | 0.0000 | 4.789226 | 0.915774 |
| 127 | | indolelactate | GC/MS | 18349 | 0.38* | 0.0198 | 0.0101 | 2.103397 | 0.792366 |
| 131 | | tryptophan betaine | LC/MS pos | 37097 | 1.07 | 0.9049 | 0.2548 | 1.250748 | 1.336430 |
| 136 | | tryptamine | LC/MS pos | 6104 | 24.64** | <0.001 | 0.0000 | 0.634729 | 15.642847 |
| 147 | | 3-indoxyl sulfate | LC/MS neg | 27672 | 0.89 | 0.8494 | 0.2453 | 0.997218 | 0.884641 |
| 148 | | indolepropionate | LC/MS neg | 32405 | 1.54** | 0.0174 | 0.0089 | 0.425099 | 0.653345 |
| 149 | Valine, leucine and isoleucine metabolism | 3-methyl-2-oxobutyrate | LC/MS neg | 21047 | 2.41** | <0.001 | 0.0000 | 0.305080 | 0.734092 |
| 150 | | 3-methyl-2-oxovalerate | LC/MS neg | 15676 | 2.30 | <0.001 | 0.0000 | 0.440157 | 1.010772 |
| 156 | | alpha-hydroxyisocaproate | LC/MS neg | 22132 | 5.83** | <0.001 | 0.0000 | 0.504073 | 2.939890 |
| 157 | | isoleucine | LC/MS pos | 1125 | 0.52* | <0.001 | 0.0002 | 2.412487 | 1.256762 |
| 158 | | leucine | LC/MS pos | 60 | 0.31* | <0.001 | 0.0000 | 3.289422 | 1.005091 |
| 162 | | N-acetylleucine | LC/MS pos | 1587 | 3.24** | <0.001 | 0.0003 | 0.500713 | 1.624179 |
| 163 | | N-acetylvalline | LC/MS pos | 1591 | 223** | <0.001 | 0.0005 | 0.432821 | 0.963793 |
| 167 | | valine | LC/MS pos | 1649 | 0.77* | 0.0282 | 0.0134 | 1.618634 | 1.239967 |
| 170 | | 4-methyl-2-oxopentanoate | LC/MS neg | 22116 | 3.11** | <0.001 | 0.000 | 0.356438 | 1.109900 |
| 175 | | alpha-hydroxyisovalerate | GC/MS | 33937 | 16.12** | <0.001 | 0.0000 | 0.087300 | 1.407149 |
| 177 | | isobutyrylcarnitine | LC/MS pos | 33441 | 0.21* | <0.001 | 0.0000 | 2.624396 | 0.553982 |
| 178 | | 2-hydroxy-3-methylvalerate | LC/MS neg | 36746 | 18.48** | <0.001 | 0.0000 | 0.088556 | 1.636135 |
| 179 | | 2-methyl-butyroylcarnitine | LC/MS pos | 35431 | 0.16* | <0.001 | 0.0000 | 2.672136 | 0.439636 |
| 188 | Cysteine, methionine, SAM, taurine metabolism | cysteine | GC/MS | 31453 | 0.03* | <0.001 | 0.0000 | 15.954344 | 0.509295 |
| 191 | | cystein | GC/MS | 31454 | 0.11* | <0.001 | 0.0002 | 0.698290 | 0.079583 |
| 193 | | methionine sulfoxide | LC/MS pos | 18374 | 0.31* | <0.001 | 0.0000 | 2.456314 | 0.750162 |
| 194 | | N-formylmethionine | LC/MS neg | 2829 | 1.20 | 0.9900 | 0.2758 | 0.652447 | 0.784818 |
| 195 | | hypolaurine | GC/MS | 590 | 0.59 | 0.1398 | 0.0533 | 1.801.513 | 1.061490 |
| 196 | | taurine | GC/MS | 2125 | 1.16 | 0.8229 | 0.2419 | 1.311479 | 1.517780 |
| 199 | | methionine | LC/MS pos | 1302 | 0.25* | <0.001 | 0.0001 | 3.820236 | 0.945843 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | | | | |
|---|---|---|---|---|---|---|---|---|---|
| 201 | | N-acetylmethionine | LC/MS neg | 1589 | *0.99* | 0.0803 | 0.0338 | 1.822001 | 1.799556 |
| 203 | | 2-hydroxybutyrate (AHB) | GC/MS | 21044 | 8.61** | <0.001 | 0.0000 | 0.291261 | 2.508011 |
| 212 | Urea cycle; arginine-, proline-, metabolism | dimethylarginine (SDMA + ADMA) | LC/MS pos | 36808 | 1.33 | 0.1164 | 0.0461 | 0.946267 | 1.262746 |
| 213 | | arginine | LC/MS pos | 1638 | 0.10* | <0.001 | 0.0001 | 4.932915 | 0.512710 |
| 216 | | ornithine | GC/MS | 1493 | 0.05* | <0.001 | 0.0002 | 19.529267 | 0.971406 |
| 217 | | urea | GC/MS | 1670 | 0.31* | 0.0066 | 0.0039 | 3.618807 | 1.108288 |
| 218 | | proline | LC/MS pos | 1898 | *1.49* | 0.0915 | 0.0382 | 1.768739 | 2.631250 |
| 219 | | 5-aminovalerate | GC/MS | 18319 | 36.22** | <0.001 | 0.0000 | 0.248177 | 8.988925 |
| 220 | | citrulline | LC/MS pos | 2132 | 3.28** | <0.001 | 0.0003 | 0.652030 | 2.135567 |
| 221 | | N-acetylornithine | LC/MS pos | 15630 | 1.88 | 0.1094 | 0.0440 | 1.173158 | 2.202987 |
| 224 | | trans-4-hydroxyproline | GC/MS | 1366 | 0.81 | 0.8755 | 0.2492 | 1.710068 | 1.382874 |
| 232 | Creatine metabolism | creatine | LC/MS pos | 27718 | 0.38* | <0.001 | 0.0000 | 1.899790 | 0.714386 |
| 233 | | creatinine | LC/MS pos | 513 | 0.66* | 0.0102 | 0.0056 | 1.415647 | 0.932472 |
| 235 | Butanoate metabolism | 2-aminobutyrate | GC/MS | 1577 | 3.64* | 0.0032 | 0.0021 | 0.842538 | 3.065685 |
| 238 | Polyamine metabolism | 5-methylthioadenosine (MTA) | LC/MS pos | 1419 | *1.49* | 0.0812 | 0.0341 | 0.856503 | 1.275299 |
| 239 | | putrescine | GC/MS | 1408 | 22.00** | <0.001 | 0.0000 | 0.314180 | 6.910507 |
| 240 | | N-acetylputrescine | LC/MS pos | 37496 | 19.83** | <0.001 | 0.0000 | 0.126190 | 2.502043 |
| 241 | | agmatine | GC/MS | 15496 | 18.45** | <0.001 | 0.0000 | 0.226448 | 4.178625 |
| 242 | | spermidine | LC/MS pos | 485 | 1.21 | 0.3210 | 0.1121 | 1.002315 | 1.217463 |
| 244 | | spermine | LC/MS pos | 603 | 0.43* | <0.001 | 0.0003 | 2.466098 | 1.058128 |
| 251 | Glutathione metabolism | glutathione, reduced (GSH) | LC/MS pos | 2127 | 0.03* | <0.001 | 0.0000 | 7.943949 | 0.247406 |
| 253 | | 5-oxoproline | LC/MS pos | 1494 | 0.51* | <0.001 | 0.0001 | 1.812848 | 0.918718 |
| 254 | | glutathione, oxidized (GSSG) | LC/MS pos | 38783 | 0.46* | 0.0494 | 0.0222 | 2.418668 | 1.109746 |
| 261 | Peptide | Dipeptide | glycylvaline | LC/MS pos | 18357 | 0.41* | 0.0035 | 0.0022 | 1.828693 | 0.748924 |
| 262 | | | glycylglycine | GC/MS | 21029 | 0.10* | <0.001 | 0.0000 | 1.241861 | 0.129154 |
| 264 | | | glycylproline | LC/MS pos | 22171 | 0.16* | <0.001 | 0.0000 | 4.315719 | 0.695861 |
| 265 | | | glycylisoleucine | LC/MS pos | 36659 | 0.43* | 0.0018 | 0.0012 | 2.270640 | 0.984348 |
| 266 | | | glycylleucine | LC/MS pos | 34398 | 0.23* | <0.001 | 0.0000 | 3.702514 | 0.869842 |
| 269 | | | glycylphenylalanine | LC/MS neg | 33954 | 0.18* | <0.001 | 0.0000 | 2.415152 | 0.429368 |
| 270 | | | glycyltyrosine | LC/MS neg | 33958 | 0.36* | 0.0023 | 0.0015 | 1.309452 | 0.474025 |
| 272 | | | alanylalanine | LC/MS neg | 15129 | 0.55* | 0.0212 | 0.0108 | 1.844075 | 1.023070 |
| 273 | | | alanylthreonine | LC/MS neg | 37085 | 0.26* | 0.0016 | 0.0010 | 1.516159 | 0.388090 |
| 274 | | | alanylvaline | LC/MS pos | 37084 | 0.27* | 0.0026 | 0.0017 | 3.456289 | 0.921019 |
| 278 | | | alanylleucine | LC/MS pos | 37093 | 0.12* | <0.001 | 0.0000 | 5.516745 | 0.645927 |
| 279 | | | alanylarginine | LC/MS neg | 37096 | 0.34* | 0.0077 | 0.0044 | 1.095681 | 0.374877 |
| 281 | | | alanylglutamate | LC/MS neg | 37064 | 0.16* | <0.001 | 0.0000 | 3.480754 | 0.571405 |
| 283 | | | alanylisoleucine | LC/MS pos | 37118 | 0.74 | 0.1699 | 0.0636 | 1.171897 | 0.871067 |
| 283.5 | | | alanylphenylalanine | LC/MS pos | 38679 | 0.14* | <0.001 | 0.0000 | 4.253526 | 0.599824 |
| 285 | | | alanyltyrosine | LC/MS neg | 37098 | 0.20* | <0.001 | 0.0001 | 1.565923 | 0.319435 |
| 286 | | | aspartylphenylalanine | LC/MS pos | 22175 | 0.36* | <0.001 | 0.0005 | 1.470863 | 0.526500 |
| 286.5 | | | aspartate-glutamate | LC/MS neg | 37461 | 0.30* | <0.001 | 0.0002 | 1.467490 | 0.439940 |
| 287 | | | alpha-glutamylglutamate | LC/MS pos | 22166 | 0.30* | <0.001 | 0.0003 | 2.474494 | 0.739946 |
| 289 | | | prolylleucine | LC/MS neg | 31914 | 0.77* | 0.0247 | 0.0121 | 0.599613 | 0.463184 |
| 291 | | | isoleucylisoleucine | LC/MS pos | 36761 | 0.64* | 0.0280 | 0.0134 | 1.522233 | 0.976674 |
| 292 | | | isoleucylleucine | LC/MS pos | 36760 | 0.67 | 0.1117 | 0.0444 | 1.572229 | 1.055765 |
| 295 | | | leucylleucine | LC/MS neg | 36756 | 0.32 | 0.1026 | 0.0419 | 1.752017 | 0.552354 |
| 299 | | | threonylphenylalanine | LC/MS pos | 31530 | 0.12* | <0.001 | 0.0000 | 6.378384 | 0.783527 |
| 300 | | | phenylalanylphenyl-alanine | LC/MS pos | 38150 | 0.60 | 0.1004 | 0.0412 | 1.023343 | 0.612418 |
| 303 | | | pyroglutamylvaline | LC/MS neg | 32394 | 0.42* | 0.0034 | 0.0021 | 1.198512 | 0.497466 |
| 304 | | | valinylglutamate | LC/MS pos | 32454 | 0.18* | <0.001 | 0.0000 | 4.490319 | 0.795339 |
| 305 | | | Isobar: glycylglutamate; glutamylglycine | LC/MS neg | 34466 | 0.69* | 0.0094 | 0.0053 | 1.373884 | 0.951120 |
| 366 | Carbo-hydrate | Aminosugars metabolism | glucosamine | GC/MS | 18534 | 0.28* | 0.0059 | 0.0035 | 1.108914 | 0.307987 |
| 372 | | | erythronate* | GC/MS | 33477 | 0.72 | 0.3424 | 0.1180 | 1.013308 | 0.732922 |
| 374 | | | N-acetylneuraminate | LC/MS pos | 32377 | 3.14** | <0.001 | 0.0002 | 0.685260 | 2.150771 |
| 379 | | | fucose | GC/MS | 15821 | *1.62* | 0.0686 | 0.0295 | 1.442967 | 2.342404 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | | | | |
|---|---|---|---|---|---|---|---|---|---|
| 389 | | Fructose, | fructose | GC/MS | 31266 | 0.28* | 0.0012 | 0.0008 | 1.756132 | 0.493023 |
| 391 | | mannose, | galactose | GC/MS | 12055 | 5.63** | <0.001 | 0.0004 | 0.318466 | 1.791958 |
| 397 | | galactose, | maltose | GC/MS | 15806 | 0.46 | 0.7206 | 0.2164 | 6.579565 | 3.020671 |
| 398 | | starch, | mannitol | GC/MS | 15335 | 0.02* | 0.0010 | 0.0007 | 5.584213 | 0.114066 |
| 410 | | and sucrose | sorbitol | GC/MS | 15053 | *0.70* | 0.0552 | 0.0241 | 0.535369 | 0.372560 |
| 417 | | metabolism | maltotriose | GC/MS | 15877 | 0.23* | 0.0095 | 0.0053 | 8.598705 | 2.015523 |
| 423 | | | maltotetraose | LC/MS neg | 15910 | 0.28* | 0.0016 | 0.0011 | 11.307067 | 3.204442 |
| 425 | | | maltopentaose | LC/MS neg | 35163 | 0.08* | <0.001 | 0.0000 | 2.031463 | 0.164349 |
| 426 | | | maltohexaose | LC/MS neg | 35170 | 0.12* | <0.001 | 0.0001 | 1.779392 | 0.221209 |
| 430 | | Glycolysis, gluconeo- | 1,5-anhydroglucitol (1.5-AG) | GC/MS | 20675 | 0.15* | <0.001 | 0.0000 | 2.539897 | 0.376257 |
| 432 | | genesis, | glycerate | GC/MS | 1572 | 0.24* | 0.0129 | 0.0068 | 3.611720 | 0.867426 |
| 434 | | pyruvate metabolism | glucose-6-phosphate (G6P) | GC/MS | 31260 | 2.74 | 0.8379 | 0.2431 | 0.699393 | 1.913208 |
| 436 | | | glucose | GC/MS | 20488 | 1.30 | 0.4973 | 0.1586 | 2.138502 | 2.781033 |
| 442 | | | Isobar fructose 1,6-diphosphate, glucose 1,6-diphosphate | LC/MS neg | 36984 | 0.18* | <0.001 | 0.0000 | 2.519516 | 0.441328 |
| 450 | | | pyruvate | GC/MS | 599 | *0.53* | 0.0996 | 0.0411 | 2.309850 | 1.228426 |
| 451 | | | lactate | GC/MS | 527 | 0.13* | <0.001 | 0.0000 | 5.553953 | 0.749216 |
| 462 | | Nucleotide | ribitol | GC/MS | 15772 | 0.42* | 0.0220 | 0.0110 | 0.981060 | 0.414604 |
| 463 | | sugars, | threitol | GC/MS | 35854 | 5.38** | <0.001 | 0.0000 | 0.194599 | 1.047048 |
| 466 | | pentose | gluconate | GC/MS | 587 | 0.11* | <0.001 | 0.0002 | 2.464444 | 0.270641 |
| 468 | | metabolism | ribose | GC/MS | 12080 | 1.02 | 0.1081 | 0.0437 | 2.115984 | 2.168290 |
| 473 | | | ribulose | GC/MS | 35855 | 0.12* | 0.0011 | 0.0007 | 1.047534 | 0.122005 |
| 477 | | | UDP-glucuronate | LC/MS neg | 2763 | 0.341 | <0.001 | 0.0002 | 1.681324 | 0.577494 |
| 479 | | | xylitol | GC/MS | 4966 | 1.44 | 0.7366 | 0.2194 | 0.478526 | 0.687893 |
| 491 | Energy | Krebs cycle | citrate | GC/MS | 1564 | *.18* | 0.0689 | 0.0295 | 7.980905 | 1.404370 |
| 499 | | Lipid | tricarballytate | LC/MS neg | 15729 | 2.90** | 0.0089 | 0.0050 | 0.964367 | 2.795634 |
| 501 | | | succinate | GC/MS | 1437 | 11.68** | <0.001 | 0.0000 | 0.356008 | 4.156583 |
| 504 | | | fumarate | GC/MS | 1643 | 0.87 | 0.4414 | 0.1431 | 1.404028 | 1.226511 |
| 507 | | | malate | GC/MS | 1303 | 0.50 | 0.9955 | 0.2761 | 2.411262 | 1.216911 |
| 511 | | Oxidative phosphor- ylation | phosphate | GC/MS | 11438 | 0.79 | 0.4293 | 0.1410 | 1.974197 | 1.568821 |
| 512.5 | | Essential fatty | linoleate (18:2n6) | LC/MS neg | 1105 | 0.64 | 0.2888 | 0.1027 | 2.503180 | 1.612596 |
| 516 | | acid | linolenate [alpha or gamma; (18:3n3 or 6)] | LC/MS neg | 34035 | *0.34* | 0.0777 | 0.0329 | 3.130635 | 1.065817 |
| 517 | | | dihomo-linolenate (20:3n3 or n6) | LC/MS neg | 35718 | 0.44* | 0.0012 | 0.0008 | 2.434987 | 1.078852 |
| 519 | | | docosapentaenoate (n3 DPA; 22:5n3) | LC/MS neg | 32504 | 0.55* | <0.001 | 0.0005 | 1.692179 | 0.931787 |
| 521 | | | docosahexaenoate (DHA, 22*6n3) | LC/MS neg | 19323 | 0.54* | 0.0231 | 0.0114 | 1.407097 | 0.758958 |
| 528 | | Medium chain fatty acid | pelargonate (9*0) | LC/MS neg | 12035 | 1.28** | 0.0437 | 0.0200 | 0.967598 | 1.240067 |
| 535 | | Long chain fatty acid | myristate (14:0) | LC/MS neg | 1365 | 1.66** | <0.001 | 0.0001 | 0.796121 | 1.324662 |
| 536 | | | myristoleate (14:1n5) | LC/MS neg | 32418 | 1.25** | 0.0422 | 0.0196 | 1.045900 | 1.305066 |
| 537 | | | pentadecanoate (15:0) | LC/MS neg | 1361 | 1.57** | 0.0082 | 0.0047 | 0.838910 | 1.315387 |
| 538 | | | palmitate (16:0) | LC/MS neg | 1336 | 0.78 | 0.6337 | 0.1956 | 1.357113 | 1.061208 |
| 539 | | | palmitoleate (16:1n7) | LC/MS neg | 33447 | 1.43 | 0.1048 | 0.0426 | 1.205405 | 1.723318 |
| 541 | | | margarate (17:0) | LC/MS neg | 1121 | 0.62* | 0.0049 | 0.0030 | 1.807274 | 1.114219 |
| 542 | | | 10-heptadecenoate (17:1n7) | LC/MS neg | 33971 | 1.03 | 0.6744 | 0.2057 | 1.522486 | 1.567355 |
| 543 | | | stearate (18:0) | GC/MS | 1358 | 0.38* | 0.0051 | 0.0030 | 2.870164 | 1.082576 |
| 545 | | | oleate (18:1n9) | GC/MS | 1359 | 0.36* | 0.0029 | 0.0019 | 3.131461 | 1.122614 |
| 547 | | | cis-vaccenate (18:1n7) | GC/MS | 33970 | *0.53* | 0.0989 | 0.0410 | 1.308343 | 0.692943 |
| 556 | | | arachidate (20:0) | GC/MS | 1118 | 0.54 | 0.1506 | 0.0570 | 1.215563 | 0.651867 |
| 559 | | | eicosenoate (20:1n9 or 11) | LC/MS neg | 33587 | 1.42 | 0.6726 | 0.2057 | 1.455978 | 2.066571 |
| 561 | | | dihomo-linoleate (20:2n6) | LC/MS neg | 17805 | 1.38 | 0.9759 | 0.2728 | 1.476627 | 2.035057 |
| 565 | | | arachidonate (20:4n6) | LC/MS neg | 1110 | 0.60* | 0.0075 | 0.0043 | 2.562764 | 1.549759 |
| 569 | | | docosadienoate (22:2n6) | LC/MS neg | 32415 | 1.37 | 0.8702 | 0.2487 | 1.276027 | 1.749032 |
| 573 | | | lignocerate (24:0) | GC/MS | 1364 | 0.98 | 0.9003 | 0.2545 | 0.958237 | 0.940437 |
| 589 | | Fatty acid, ester | n-Butyl Oleate | GC/MS | 36802 | *0.64* | 0.0506 | 0.0223 | 0.854271 | 0.544793 |
| 591 | | Fatty acid, monohydroxy | 4-hydroxybutyrate (GHB) | GC/MS | 34585 | 20.00** | <0.001 | 0.0000 | 0.084776 | 1.695504 |
| 602 | | | 2-hydroxystearate | LC/MS neg | 17945 | 1.57 | 0.3032 | 0.1068 | 1.381444 | 2.167484 |
| 603 | | | 13-HODE | LC/MS neg | 37374 | 3.90** | 0.0042 | 0.0026 | 1.448723 | 5.656509 |
| 604 | | | 2-hydroxypalmitate | LC/MS neg | 35675 | 1.24 | 0.8312 | 0.2430 | 2.094107 | 2.590470 |
| 610 | | Fatty acid, | 2-hydroxyglutarate | GC/MS | 37253 | 12.02** | <0.001 | 0.0000 | 0.573594 | 6.896975 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | | | | |
|---|---|---|---|---|---|---|---|---|---|
| 616 | | dicarboxylate | azelate (nonanedioate) | LC/MS neg | 18362 | 0.67 | 0.4340 | 0.1413 | 1.578876 | 1.061955 |
| 621 | | | undecanedioate | LC/MS neg | 35671 | 0.81* | 0.0497 | 0.0222 | 1.094301 | 0.885314 |
| 622 | | | 3-carboxy-4-methyl-5-propyl-2-furanpropanoate (CMPF) | LC/MS neg | 31787 | 0.86 | 0.3299 | 0.1147 | 0.440869 | 0.378743 |
| 632.5 | | Fatty acid, branched | 13-methylmyristic acid | LC/MS neg | 38293 | 1.95** | <0.001 | 0.0000 | 0.710272 | 1.385212 |
| 632.65 | | | methyl palmitate (15 or 2) | LC/MS neg | 38768 | 1.23 | 0.1820 | 0.0678 | 0.966898 | 1.188506 |
| 632.7 | | | 17-methylstearate | LC/MS neg | 38296 | 1.22 | 0.5782 | 0.1806 | 1.227807 | 1.500760 |
| 672 | | Eicosanoid | 12-HETE | LC/MS neg | 37536 | 7.05** | <0.001 | 0.0002 | 0.796090 | 5.614170 |
| 678 | | Endocannabinoid | oleic ethanolamide | LC/MS neg | 38102 | 4.72** | <0.001 | 0.0000 | 0.364114 | 1.811836 |
| 679 | | | palmitoyl ethanolamide | LC/MS neg | 38165 | 4.97** | <0.001 | 0.0000 | 0.470637 | 2.337596 |
| 683 | | Fatty acid metabolism | propionylcarnitine | LC/MS pos | 32452 | 0.24* | <0.001 | 0.0000 | 2.834756 | 0.690499 |
| 685 | | (also BCAA metabolism) | butyrylcarnitine | LC/MS pos | 32412 | 0.34* | <0.001 | 0.0000 | 2.199301 | 0.738763 |
| 691 | | Carnitine metabolism | deoxycarnitine | LC/MS pos | 36747 | 22.972 | <0.001 | 0.0000 | 0.124527 | 2.860155 |
| 692 | | | carnitine | LC/MS pos | 15500 | 0.32* | <0.001 | 0.0000 | 2.285080 | 0.720942 |
| 693 | | | 3-dehydrocarnitine* | LC/MS pos | 32654 | 1.07 | 0.9085 | 0.2549 | 1.056017 | 1.133051 |
| 694 | | | acetylcarnitine | LC/MS pos | 32198 | 0.20* | <0.001 | 0.0000 | 3.840583 | 0.784791 |
| 746 | | Glycerolipid metabolism | ethanolamine | GC/MS | 34285 | 1.59 | 0.0504 | 0.0223 | 1.337565 | 2.130038 |
| 747 | | | phosphoethanolamine | GC/MS | 12102 | 0.70 | 0.2959 | 0.1047 | 1.231679 | 0.856039 |
| 750 | | | glycerol | GC/MS | 15122 | 0.44* | 0.0462 | 0.0209 | 2.884838 | 1.279821 |
| 752 | | | glycerol 3-phosphate (G3P) | GC/MS | 15365 | 0.25* | <0.001 | 0.0001 | 3.593932 | 0.881919 |
| 753 | | | glycerophosphoryl-choline (GPC) | LC/MS pos | 15990 | 0.18* | <0.001 | 0.0000 | 7.439241 | 1.342709 |
| 760 | | Inositol metabolism | myo-inositol | GC/MS | 19934 | 0.31* | <0.001 | 0.0001 | 3.091537 | 0.969853 |
| 767 | | | scyllo-inositol | GC/MS | 32379 | 0.49* | 0.0108 | 0.0058 | 1.564517 | 0.762610 |
| 771 | | Ketone bodies | 1,2-propanediol | GC/MS | 38002 | 0.01 | 0.1276 | 0.0495 | 81.309337 | 1.067614 |
| 778 | | Lysolipid | 2-palmitoleoylglycero-phosphoethanolamine* | LC/MS neg | 36619 | 0.53* | 0.0037 | 0.0023 | 1.407027 | 0.744857 |
| 780 | | | 1-stearoylglycerophos-phoethanolamine | LC/MS neg | 34416 | 0.20* | <0.001 | 0.0000 | 2.538105 | 0.507276 |
| 781 | | | 1-oleoylglycerophos-phoethanolamine | LC/MS neg | 35628 | 0.591 | 0.0444 | 0.0201 | 1.906482 | 1.123846 |
| 782 | | | 2-oleoylglycerophos-phoethanolamine* | LC/MS neg | 35687 | 0.59 | 0.0515 | 0.0226 | 1.788931 | 1.054957 |
| 783 | | | 1-linoleoylglycerophos-phoethanolamine* | LC/MS neg | 32635 | 0.57* | 0.0276 | 0.0134 | 1.609657 | 0.920543 |
| 784 | | | 2-linoleoylglycerophos-phoethanolamine* | LC/MS neg | 36593 | 0.47* | <0.001 | 0.0001 | 1.606901 | 0.759890 |
| 785 | | | 1-arachidonoylglycero-phosphoethanolamine* | LC/MS neg | 35186 | 0.56* | 0.0114 | 0.0061 | 1.424438 | 0.795836 |
| 786 | | | 2-arachidonoylglycero-phosphoethanolamine* | LC/MS neg | 32815 | 0.47* | 0.0020 | 0.0013 | 1.349214 | 0.628647 |
| 794 | | | 1-palmitoylglycero-phosphocholine | LC/MS neg | 33955 | 0.25* | <0.001 | 0.0000 | 1.663882 | 0.411784 |
| 799 | | | 1-stearoylglycerophos-choline | LC/MS pos | 33961 | 1.26 | 0.1396 | 0.0533 | 1.067878 | 1.345730 |
| 802 | | | 2-oleoylglycerophos-phochotine* | LC/MS pos | 35254 | 0.80 | 0.4231 | 0.1401 | 0.836825 | 0.673232 |
| 824 | | | 1-oleoylglycero-phosphoserine | LC/MS neg | 19260 | 0.93 | 0.3897 | 0.1319 | 1.893220 | 1.758314 |
| 825.5 | | | 1-palmitoylplasmenyl-ethanolamine* | LC/MS neg | 39270 | 0.36* | <0.001 | 0.0003 | 2.917835 | 1.051735 |
| 833 | | Monoacyl-glycerol | 1-stearoylglycerol (1-monostearin) | GC/MS | 21188 | 0.30* | 0.0116 | 0.0061 | 1.079715 | 0.323913 |
| 853 | | Sphingolipid | sphinganine | LC/MS pos | 17769 | 0.98 | 0.6974 | 0.2110 | 2.095458 | 2.044173 |
| 855 | | | sphingosine | LC/MS pos | 17747 | 1.02 | 0.1177 | 0.0464 | 2.767111 | 2.823340 |
| 864 | | | palmitoyl sphingomyelin | GC/MS | 37506 | 0.85 | 0.3346 | 0.1158 | 1.625145 | 1.387937 |
| 879 | | Sterol/Steroid | lathosterol | GC/MS | 33488 | 0.73 | 0.2682 | 0.0958 | 0.889059 | 0.645631 |
| 881 | | | cholesterol | GC/MS | 63 | 0.76 | 0.2047 | 0.0752 | 1.697102 | 1.283848 |
| 883 | | | dihydrocholesterol | GC/MS | 21131 | 2.78 | 0.3959 | 0.1331 | 0.822348 | 2.286362 |
| 891 | | | dehydroisoandrosterone sulfate (DHEA-S) | LC/MS neg | 32425 | 0.98 | 0.6553 | 0.2015 | 0.620480 | 0.607584 |
| 895 | | | androsterone sulfate | LC/MS neg | 31591 | 1.09 | 0.5726 | 0.1796 | 0.539983 | 0.587072 |
| 935 | | | 4-androsten-3beta,17beta-diol disulfate 1* | LC/MS neg | 37202 | 1.04 | 0.5474 | 0.1724 | 0.690855 | 0.718376 |
| 947 | Nucleo-tide | Purine metabolism, | xanthine | GC/MS | 3147 | 1.91 | 0.4941 | 0.1582 | 1.005427 | 1.916714 |
| 950 | | | hypoxanthine | LC/MS | 3127 | 0.37* | <0.001 | 0.0003 | 3.114551 | 1.147087 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | | | | |
|---|---|---|---|---|---|---|---|---|---|
| 951 | | (hypo)-xanthine/ inosine containing | inosine | neg LC/MS neg | 1123 | 0.071 | <0.001 | 0.0000 | 1.748493 | 0.119613 |
| 955 | | Purine | adenine | LC/MS pos | 554 | *0.70* | 0.0572 | 0.0248 | 1.459897 | 1.021916 |
| 956 | | metabolism | adenosine | LC/MS pos | 555 | 0.33* | 0.0132 | 0.0069 | 2.679957 | 0.894570 |
| 964 | | adenine containing | adenosine 5'-monophos-phate (AMP) | LC/MS pos | 32342 | 0.36* | <0.001 | 0.0000 | 1.631900 | 0.588981 |
| 973 | | Purine metabolism. | guanine | LC/MS pos | 32352 | 0.40 | 0.2234 | 0.0817 | 3.619263 | 1.459953 |
| 976 | | guanine containing | N2,N2-dimethylguanine | LC/MS pos | 37081 | 1.66** | 0.0428 | 0.0198 | 0.790915 | 1.311851 |
| 977 | | | guanosine | LC/MS pos | 1573 | 0.31* | 0.0044 | 0.0027 | 2.315595 | 0.723458 |
| 988 | | | 2'-O-methylguanosine | LC/MS pos | 36811 | 1.611 | 0.0362 | 0.0169 | 0.429850 | 0.691926 |
| 994 | | Purine metabolism, urate metabolism | urate | LC/MS neg | 1604 | 0.53* | 0.0097 | 0.0053 | 1.241189 | 0.657312 |
| 1016 | | Pyrimidine meta-bolism, thymine containing | thymine | GC/MS | 604 | 18.13** | <0.001 | 0.0000 | 0.177007 | 3.209986 |
| 1021 | | Pyrimidine metabolism, thymine containing; Valine leucine and isoleucine metabolism/ | 3-aminoisobutyrate | GC/MS | 1566 | 1.24 | 0.4286 | 0.1410 | 1.024298 | 1.269410 |
| 1022 | | Pyrimidine | uracil | GC/MS | 605 | 0.62 | 0.1577 | 0.0594 | 2.927632 | 1.811774 |
| 1024 | | metabolism, uracil | uridine | LC/MS neg | 606 | 0.36* | <0.001 | 0.0000 | 2.435443 | 0.880983 |
| 1025 | | containing | pseudouridine | LC/MS neg | 33442 | 0.26* | <0.001 | 0.0000 | 2.247591 | 0.580166 |
| 1030.2 | | | uridine monophosphate (5'or 3') | LC/MS pos | 39879 | 0.81 | 0.1877 | 0.0696 | 0.955846 | 0.778221 |
| 1040 | Co-factors and vita-mins | Ascorbate and aldarate metabolism | ascorbate (Vitamin C) | GC/MS | 1640 | 0.01* | <0.001 | 0.0002 | 11.476273 | 0.106009 |
| 1041 | | | dehydroascorbate | GC/MS | 1659 | 0.53* | 0.0431 | 0.0198 | 0.402364 | 0.215056 |
| 1055 | | Hemoglobin and porphyrin | heme* | LC/MS pos | 32593 | 0.32 | 0.4722 | 0.1518 | 4.510335 | 1.437990 |
| 1063 | | Nicotinate and nicotinamide metabolism | nicotinamide | LC/MS pos | 594 | 0.30* | <0.001 | 0.0002 | 2.563745 | 0.756635 |
| 1066 | | | nicotinamide adenine dinucleotide (NAD+) | LC/MS pos | 5278 | 0.20* | <0.001 | 0.0000 | 1.328450 | 0.268022 |
| 1074 | | | adenosine 5'diphospho-ribose | LC/MS neg | 558 | 0.40* | 0.0220 | 0.0110 | 1.648350 | 0.667043 |
| 1077 | | | nicotoate | LC/MS pos | 1504 | 4.87** | <0.001 | 0.0000 | 0.439218 | 2.139249 |
| 1085 | | Pantothenate and CoA metabolism | pantothenate | LC/MS pos | 1508 | 1.04 | 0.3467 | 0.1189 | 1.248344 | 1.302237 |
| 1088 | | | 3'-dephosphocoenzyme A | LC/MS neg | 18289 | 1.65** | 0.0048 | 0.0029 | 0.305462 | 0.505276 |
| 1098 | | Riboflavin metabolism | flavin adenine dinucleotide (FAD) | LC/MS neg | 2134 | 2.05** | <0.001 | 0.0001 | 0.565367 | 1.159047 |
| 1099 | | | riboflavin (Vitamin B2) | LC/MS pos | 1827 | 1.79 | 0.1402 | 0.0533 | 0.628271 | 1.124005 |
| 1105 | | Tocopherol metabolism | alpha-tocopherol | GC/MS | 1561 | 0.76* | 0.0302 | 0.0143 | 0.560465 | 0.428338 |
| 1117 | | Vitamin B5 metabolism | pyridoxate | LC/MS neg | 31555 | 1.07 | 0.7353 | 0.2194 | 0.989351 | 1.058418 |
| 1123 | Xeno-biotics | Benzoate metabolism | hippurate | LC/MS neg | 15753 | 0.08* | 0.0105 | 0.0057 | 5.395996 | 0.453304 |
| 1126.5 | | | 3-hydroxyhippurate | LC/MS neg | 39600 | 0.33* | 0.0282 | 0.0134 | 1.316128 | 0.435932 |
| 1127 | | | 4-hydroxyhippurate | LC/MS neg | 35527 | 1.08 | 0.8552 | 0.2453 | 0.790986 | 0.855582 |
| 1134 | | | catechol sulfate | LC/MS neg | 35320 | 0.46 | 0.3141 | 0.1102 | 1.497728 | 0.687864 |
| 1157 | | Chemical | glycerol 2-phosphate | GC/MS | 27728 | 0.18* | <0.001 | 0.0002 | 1.215266 | 0.221673 |
| 1161 | | | heptaethylene glycol | LC/MS pos | 38154 | 0.05 | 0.6818 | 0.2071 | 92.519657 | 4.360554 |
| 1162 | | | hexaethylene glycol | LC/MS pos | 38133 | 0.07 | 0.3874 | 0.1317 | 20.503810 | 1.421641 |
| 1163 | | | octaethylene glycol | LC/MS pos | 38155 | 0.05 | 0.3993 | 0.1331 | 107.214971 | 5.896527 |
| 1164 | | | pentaethylene glycol | LC/MS pos | 38158 | 0.56 | 0.1946 | 0.0719 | 2.046873 | 1.150927 |
| 1180 | | | 2-pyrrolidinone | GC/MS | 31675 | 0.34 | 0.1244 | 0.0485 | 1.378630 | 0.466938 |
| 1216 | | Drug | 4-acetaminophen sulfate | LC/MS neg | 37475 | 0.26 | 0.4002 | 0.1331 | 0.699167 | 0.182977 |
| 1217 | | | 4-acetamidophenol | LC/MS pos | 12032 | 0.86 | 0.8519 | 0.2453 | 0.426936 | 0.366874 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| 1218 | | p-acetamidophenylglu-curonide | LC/MS neg | 33423 | 0.11 | 0.3983 | 0.1331 | 2.333262 | 0.260924 |
|---|---|---|---|---|---|---|---|---|---|
| 1219 | | 2-hydroxyacetamino phen sulfate* | LC/MS neg | 33173 | 0.50 | 0.2670 | 0.0958 | 0.553826 | 0.279180 |
| 1220 | | 2-methoxyacetamino phen sulfate* | LC/MS neg | 33178 | 0.91 | 0.5959 | 0.1847 | 0.455487 | 0.413317 |
| 1221 | | 3-(cystein-S-yl) acetaminophen* | LC/MS pos | 34365 | 0.61 | 0.4318 | 0.1412 | 0.753281 | 0.459078 |
| 1268.6 | | benzoylecgonine | LC/MS pos | 39678 | 0.64 | 0.9982 | 0.2761 | 0.899112 | 0.578359 |
| 1281 | Food component/ | saccharin | LC/MD neg | 21151 | 0.84 | 0.4548 | 0.1468 | 0.387694 | 0.327339 |
| 1341 | Plant | stachydrine | LC/MS pos | 34384 | 1.07 | 0.8783 | 0.2492 | 1.455998 | 1.561888 |
| 1343 | Xanthine metabolism | caffeine | LC/MS pos | 569 | 0.94 | 0.5837 | 0.1816 | 1.283809 | 1.211907 |
| 1344 | | paraxanthine | LC/MS pos | 18254 | 1.44 | 0.2391 | 0.0862 | 0.665644 | 0.960747 |
| 1345 | | theobromine | LC/MS pos | 18392 | 1.18 | 0.3540 | 0.1209 | 0.799624 | 0.940328 |
| 1349 | | 1,7-dimethylurate | LC/MS neg | 34400 | 0.96 | 0.8246 | 0.2419 | 0.865293 | 0.832235 |
| 1360 | Sugar, sugar substitute, starch | erythritol | GC/MS | 20699 | 0.94 | 0.7059 | 0.2128 | 0.963717 | 0.901261 |

| BIOCHEMICAL NAME | CAS | PUBCHEM | KEGG | HMDB | RP | MASS |
|---|---|---|---|---|---|---|
| glycine | 56-40-6; | 5,257,127,750 | C00037 | HMDB00123 | 1166 | 101.9 |
| sarcosine (N-Methylglycine) | 107-97-1; | 10,887,311,726 | C00213 | HMDB00271 | 1182.9 | 116 |
| serine | 56-45-1; | 59,516,857,581 | C00065 | HMDB03406 | 1389.1 | 204 |
| N-acetylserine | 97-14-3; | 65249 | | HMDB02931 | 1012 | 148 |
| threonine | 72-19-5; | 69,710,196,288 | C00188 | HMDB00167 | 1412.3 | 218.1 |
| N-acetylthreonine | | 4651717 | C01118 | | 846 | 160.1 |
| betaine | 107-43-7; | 247 | | HMDB00043 | 721 | 118.2 |
| alanine | 56-41-7; | 59,507,311,724 | C00041 | HMDB00161 | 1147.6 | 115.9 |
| beta-alanine | 56-41-7; 107-95-9; | 2,394,755,801 | C00099 | HMDB00056 | 1451.8 | 174 |
| N-acetylalanine | 97-69-8; | 88064 | C02847 | HMDB00766 | 882 | 130.1 |
| aspartate | 56-84-8; | 5960 | C00049 | HMDB00191 | 1529.7 | 232 |
| N-acetylaspartate (NAA) | 997-55-7;997-55-7; | 65065 | C01042 | HMDB00812 | 1222 | 176.1 |
| glutamate | 56-86-0; | 611 | C00025 | HMDB03339 | 700 | 148.1 |
| glutamine | 56-85-9; | 69,920.865,961 | C00064 | HMDB00641 | 684 | 147.2 |
| pyroglutamine* | | 134508 | | | 764 | 129.2 |
| gamma-aminobutyrate (GABA) | 56-12-2; | 6,992,099,119 | C00334 | HMDB00112 | 1539.7 | 304.1 |
| N-acetylglutamate | 5817-09-3; | 1549099 | C00624 | HMDB01138 | 1492 | 190.1 |
| histidine | 5934-29-2; | 7,733,651,426 | C00135 | HMDB00177 | 757 | 154.1 |
| urocanate | 104-98-3; | 736715 | C00785 | HMDB00301 | 1164 | 139.1 |
| histamine | 51-45-6; | 774 | C00388 | HMDB00870 | 1809.7 | 174.1 |
| cadaverine | 462-94-2;1476-39-7; | | C01672 | HMDB02322 | 1780.4 | 174 |
| lysine | 56-87-1; | 5962 | C00047 | HMDB00182 | 1836.7 | 317.2 |
| 2-aminoadipate | 542-32-5;1118-90-7; | 469 | C00956 | HMDB00510 | 16865 | 260.1 |
| pipecolate | 4043-87-2; | 849 | C00408 | HMDB00070 | 1120 | 130.1 |
| N6-acetyllysine | 692-04-6; | 699,197,892,832 | C02727 | HMDB00206 | 1134 | 189.1 |
| phenyllactate (PLA) | 828-01-3; | 3848 | C05607 | HMDB00779 | 2237 | 165.1 |
| phenylalanine | 63-91-2; | 69,256,656,140 | C00079 | HMDB00159 | 2056 | 166.1 |
| Isobar: 1-phenylethanamine, phenylethyamine | | | C02455, C05332 | HMDB02017 HMDB12275 | 2114.7 | 122.1 |
| phenylacetate | 103-82-2; | | C07086 | HMDB00209 | 2127 | 135.1 |
| p-cresol sulfate | 3233-57-7; | 4615422 | C01468 | | 2896 | 187.1 |
| tyrosine | 60-18-4; | 60,576,942,100 | C00082 | HMDB00158 | 1516 | 182.1 |
| 3-(4-hydroxyphenyl)lactate | 6482-98-0; | 9378 | C03672 | HMDB00755 | 1395 | 181.1 |
| tyramine | 60-19-5; | 5610 | C00483 | HMDB00306 | 1503 | 138.1 |
| 4-hydroxyphenylacetate | 156-38-7; | 4693933 | C00642 | HMDB00020 | 1630.6 | 179 |
| N-acetylphenylalanine | 2018-61-3; | 74839 | C03519 | HMDB00512 | 2590 | 206.2 |
| phenylacetylglutamine | 28047-15-6; | 306137 | C05597 | HMDB06344 | 2868 | 265.2 |
| 3-(4-hydroxyphenyl)propionate | 501-97-3; | 10394 | C01744 | HMDB02199 | 1727.9 | 179.1 |
| 3-phenylpropionate (hydrocinnamate) | 501-52-0; | | C05629 | HMDB00764 | 2830 | 149.1 |
| phenol sulfate | 937-34-8; | 74426 | C02180 | | 2199 | 173.1 |
| kynurenate | 492-27-3; | 3845 | C01717 | HMDB00715 | 2243 | 188.1 |
| kynurenine | 2922-83-0; | 1,611,666,971,029 | C00328 | HMDB00684 | 1902 | 209.1 |
| tryptophan | 73-22-3; | 69,235,166,305 | C00078 | HMDB00929 | 2445 | 205.1 |
| indolelactate | 832-97-3; | 92904 | C02043 | HMDB00671 | 1964.9 | 202 |
| tryptophan betaine | 20671-76-5; | 442106 | C09213 | | 2464 | 247.1 |
| tryptamine | 61-54-1; | 1150 | C00398 | HMDB00303 | 2323 | 161.1 |
| 3-indoxyl sulfate | 2642-37-7; | 10258 | | HMDB00682 | 2258 | 212 |
| indolepropionate | 830-96-6; | 3744 | | HMDB02302 | 2795 | 188.2 |
| 3-methyl-2-oxobutyrate | 3715-29-5; | 49 | C00141 | HMDB00019 | 1489 | 115.1 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | |
|---|---|---|---|---|---|---|
| 3-methyl-2-oxovalerate | 51829-07-3; | 47 | C00671 | HMDB03736 | 2106 | 129.2 |
| alpha-hydroxyisocaproate | 10303-64-7; | 83697 | C03264 | HMDB00746 | 1854 | 131.2 |
| isoleucine | 73-32-5; | 791 | C00407 | HMDB00172 | 1614 | 132.1 |
| leucine | 61-90-5; | 70,457,986,106 | C00123 | HMDB00687 | 1674 | 132.2 |
| N-acetylleucine | 1188-21-2; | 70912 | C02710 | HMDB11756 | 3444 | 174.1 |
| N-acetylvaline | 96-81-1; | 66789 | | HMDB11757 | 2654 | 160.1 |
| valine | 72-18-4; | 69,710,186,287 | C00183 | HMDB00883 | 1040 | 118.1 |
| 4-methyl-2-oxopentanoate | 816-66-0; | 70 | C00233 | HMDB00695 | 2200 | 129.2 |
| alpha-hydroxyisovalerate | 600-37-3; | 99823 | | HMDB00407 | 1208 | 145.1 |
| isobutyrylcarnitine | 25518-49-4; | | | | 1941 | 232.2 |
| 2-hydroxy-3-methylvalerate | 488-15-3; | 164623 | | HMDB00317 | 1787 | 131.1 |
| 2-methylbutyroylcarnitine | 31023-25-3; | 6426901 | | HMDB00378 | 2439 | 246.1 |
| cysteine | 52-90-4;56-89-3* | 58,626,419,722 | C00097 | HMDB00574 | 1560.1 | 218 |
| cystine | 56-89-3; | 595 | C00491 | HMDB00192 | 2015.3 | 218 |
| methionine sulfoxide | 3226-65-1; | 1,589,801,548,907 | C02989 | HMDB02005 | 729 | 166.1 |
| N-formylmethionine | 4289-98-9; | 439750 | C03145 | HMDB01015 | 1541 | 176.1 |
| hypotaurine | 300-84-5; | 107812 | C00519 | HMDB00965 | 1598.5 | 188 |
| taurine | 107-35-7; | 11,234,068,592 | C00245 | HMDB00251 | 16164 | 254.1 |
| methionine | 63-68-3; | 69,920,876,137 | C00073 | HMDB00696 | 1252 | 150.1 |
| N-acetylmethionine | 65-82-7; | 448580 | C02712 | HMDB11745 | 1805 | 190.1 |
| 2-hydroxybutyrate (AHB) | 3347-90-8; | 440864 | C05984 | HMDB00008 | 1169.4 | 130.9 |
| dimethylarginine (SDMA + ADMA) | | 123831 | C03626 | HMDB01539. HMDB03334 | 812 | 203.2 |
| arginine | 1119-34-2; | 5,246,487,232 | C00062 | HMDB00517 | 650 | 175.2 |
| ornithine | 3184-13-2; | 6262 | C00077 | HMDB03374 | 1763.8 | 141.9 |
| urea | 57-13-6; | 117,616,150,869 | C00086 | HMDB00294 | 1223.9 | 171 |
| proline | 147-85-3; | 1,457,496,971,047 | C00148 | HMDB00162 | 796 | 116.1 |
| 5-aminovalerate | 660-88-8; | 6,992,101,138 | C00431 | HMDB03355 | 1620.8 | 174 |
| citrulline | 372-75-8* | 833 | C00327 | HMDB00904 | 715 | 176.1 |
| N-acetylornithine | 6205-08-9; | 6,992,102,439,232 | C00437 | HMDB03357 | 875 | 175.2 |
| trans-4-hydroxyproline | 51-35-4; | 58,106,971,053 | C01157 | HMDB00725 | 1537 | 140 |
| creatine | 57-00-1; | 586 | C00300 | HMDB00064 | 758 | 132.1 |
| creatinine | 60-27-5; | 588 | C00791 | HMDB00562 | 730 | 114.1 |
| 2-aminobutyrate | 1492-24-6; | 4,396,916,971,251 | C02261 | HMDB00650 | 1215.7 | 130 |
| 5-methylthioadenosine (MTA) | 2457-80-9; | 439176 | C00170 | HMDB01173 | 2427 | 298.1 |
| putrescine | 110-60-1; | | C00134 | HMDB01414 | 1705.8 | 174 |
| N-acetylputresdne | 18233-70-0; | 122356 | C02714 | HMDB02064 | 895 | 131.1 |
| agmatine | 2482-00-0; | 199 | C00179 | HMDB01432 | 1528 | 174 |
| spermidine | 124-20-9; | 1102 | C00315 | HMDB01257 | 533 | 146.2 |
| spermine | 71-44-3; | 1103 | C00750 | HMDB01256 | 506 | 203.2 |
| glutathione, reduced (GSH) | 70-18-8; | 124886 | C00051 | HMDB00125 | 1274 | 308.1 |
| 5-oxoproline | 98-79-3; | 7405 | C01879 | HMDB00267 | 1446 | 130.1 |
| glutathione, oxidized (GSSG) | 103239-24-3; | 6,535,911,215,652 | C00127 | HMDB03337 | 1535 | 307.3 |
| glycylvaline | 1963-21-9; | 27,248,076.994,979 | | | 1572 | 175.1 |
| glycylglycine | 556-50-3* | 154,889,711,163 | C02037 | HMDB11733 | 1757.9 | 174 |
| glycylproline | 704-15-4* | 30,136,256,993,386 | | HMDB00721 | 1115 | 173.1 |
| glycylisoleucine | 19461-38-2; | | | | 2080 | 189.1 |
| glycylleucine | 869-19-2; | 928,431,548,899 | C02155 | HMDB00759 | 2236 | 189.1 |
| glycylphenylalanine | 3321-03-7; | 154,934,492,953 | | | 2193 | 221.2 |
| glycyltyrosine | 658-79-7; | 928,296,994,980 | | | 1446 | 237.2 |
| alanylalanine | 1948-31-8; | 54,603,626,992,112 | C00993 | HMDB03459 | 815 | 159.2 |
| alanylthreonine | | 426318 | | | 827 | 189 |
| alanylvaline | | 137276 | | | 1513 | 189 |
| alanylleucine | | 259583 | | | 2150 | 203 |
| alanylarginine | | 9964828 | | | 1079 | 244.1 |
| alanylglutamate | | 656476 | | | 766 | 219 |
| alanylisoleucine | | 4,173,585,246.008 | | | 2011 | 203.1 |
| alanylphenylalanine | 3061-90-3; | 2080 | | | 2422 | 237.2 |
| alanyltyrosine | | 5,723,194,099,800 | | | 1642 | 251 |
| aspartylphenylalanine | 13433-09-5; | 93078 | | HMDB0706 | 2538 | 281.1 |
| aspartate-glutamate | 6157-06-8; | 4130574 | | | 603 | 261.2 |
| alpha-glutamylglutamate | 3929-61-1; | 439500 | C01425 | | 857 | 277.1 |
| prolylleucine | 52899-07-7; | 4,441,097,082,009 | | | 2985 | 227.2 |
| isoleucylisoleucine | 42537-99-5; | | | | 2678 | 245.1 |
| isoleucylleucine | 26462-22-6; | 11644431 | | | 2856 | 245.1 |
| leucylleucine | 3303-31-9; | 768,076,992,072 | C11332 | | 3895 | 243.2 |
| threonylphenylalanine | | 40,997,994.099,798 | | | 2500 | 267.2 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | |
|---|---|---|---|---|---|---|
| phenylalanylphenylalanine | 2577-40-4; | 69,930,906.993, 089 | | | 3317 | 313.2 |
| pyroglutamylvaline | | 152416 | | | 1755 | 227.2 |
| valinylglutamate | 3062-07-5; | 7009623 | | | 1346 | 247.1 |
| Isobar: glycylglutamate; glutamylglycine | | | | | 634 | 203.1 |
| glucosamine | 66-84-2; | 441477 | C00329 | HMDB01514 | 1833 | 203 |
| erythronate* | 13752-84-6; | 2781043 | | HMDB00613 | 1546.9 | 292.1 |
| N-acetylneuraminate | 131-48-6; | | C00270 | HMDB00230 | 787 | 310 |
| fucose | 2438-80-4; | 3034656 | C00382 | HMDB00174 | 1682.2 | 204 |
| fructose | 57-48-7; | 5984 | C00095 | HMDB00660 | 1762.7 | 204 |
| galactose | 59-23-4; | 3037556 | C01582 | HMDB00143 | 1793.8 | 203.9 |
| maltose | 6363-53-7; | 439341 | C00208 | HMDB00163 | 2142.1 | 204.1 |
| mannitol | 69-65-8; | 6251 | C00392 | HMDB00765 | 1839 | 319.1 |
| sorbitol | 6706-59-8; | 107428 | C00794 | HMDB00247 | 1843 | 319.1 |
| maltotriose | 1109-28-0; | 439586 | C01835 | HMDB01262 | 2419 | 204 |
| maltotetraose | 34612-38-9; | 446495 | C02052 | HMDB01296 | 965 | 665.1 |
| maltopentaose | 34620-76-3; | 3710145 | C06218 | HMDB12254 | 1100 | 827 |
| maltohexaose | 34620-77-4; | 5288409 | C01936 | HMDB12253 | 1224 | 989 |
| 1,5-anhydroglucitol (1,5-AG) | 154-58-5; | | C07326 | HMDB02712 | 1788.7 | 217 |
| glycerate | 600-19-1; | 752 | C00258 | HMDB00139 | 1360.7 | 189 |
| glucose-6-phosphate (G6P) | 103192-55-8; | | C00668 | HMDB01401 | 2042.7 | 387.2 |
| glucose | 50-99-7; | 79025 | C00293 | HMDB00122 | 1866.8 | 217.1 |
| Isobar: fructose 1,6-diphosphate, glucose 1,6-diphosphate | | | | | 572 | 339 |
| pyruvate | 127-17-3; | 107735 | C00022 | HMDB00243 | 1130.6 | 217 |
| lactate | 79-33-4; | 612 | COO186 | HMDB00190 | 1102.8 | 116.9 |
| ribitol | 488-81-3; | | C00474 | HMDB00508 | 1692.4 | 217 |
| threitol | 2418-52-2; | 169019 | C16884 | HMDB04136 | 1513 | 217.1 |
| gluconate | 527-07-1; | 10690 | C00257 | HMDB00625 | 1879.4 | 333 |
| ribose | 50-69-1; | 5311110 | C00121 | HMDB00283 | 1639.2 | 204 |
| ribulose | 488-84-6; | 79021 | C00309 | HMDB00621, HMDB03371 | 1662 | 306.1 |
| UDP-glucuronate | 28053-08-9; 63700-19-6; | 17473 | C00167 | HMDB00935 | 594 | 579.1 |
| xylitol | 87-99-0; | 6912 | C00379 | HMDB00568 | 1677.6 | 307.2 |
| citrate | 77-92-9; | 311 | C00158 | HMDB00094 | 1763.4 | 273.1 |
| tricarballylate | 99-14-9; | 14925 | | | 592 | 175 |
| succinate | 110-15-6; | 1110 | C00042 | HMDB00254 | 1348 | 247 |
| fumarate | 100-17-8; | | C00122 | HMDB00134 | 1382.1 | 245 |
| malate | 6915-15-7; | 525 | C00149 | HMDB00156 | 1502 | 233 |
| phosphate | 7664-38-2; | 1061 | C00009 | HMDB01429 | 1307.7 | 298.9 |
| linoleate (18:2n6) | 60-33-3; | 5280450 | C01595 | HMDB00673 | 5533 | 279.3 |
| linolenate [alpha or gamma; (18:3n3 or 6)] | | | C06427 | HMDB01388 | 5450 | 277.3 |
| dihomo-linolenate (20:3n3 or 6) | | 5312529 | C03242 | HMDB02925 | 5600 | 305.4 |
| docosapentaenoate (n3 DPA; 22:5n3) | 2234-74-4; | | C16513 | HMDB01976 | 5574 | 329.4 |
| docosahexaenoate (DHA; 22:6n3) | 6217-54-5; | 445580 | C06429 | HMDB02183 | 5518 | 327.3 |
| pelargonate (9:0) | 112-05-0* | 5461016 | C01601 | HMDB00847 | 4847 | 157.2 |
| myristate (14:0) | 544-63-8* | 11005 | C06424 | HMDB00806 | 5439 | 227.3 |
| myristoleate (14:1n5) | 544-64-9; | 5281119 | C08322 | HMDB02000 | 5338 | 225.3 |
| pentadecanoate (15:0) | 1002-84-2; | 13849 | C16537 | HMDB00826 | 5522 | 241.3 |
| palmitate (16:0) | 57-10-3; | 985 | C00249 | HMDB00220 | 5619 | 255.3 |
| palmitoleate (16:1n7) | 373-49-9; | 445638 | C08362 | HMDB03229 | 5477 | 253.3 |
| margarate (17:0) | 506-12-7; | 10465 | | HMDB02259 | 5733 | 269.3 |
| 10-heptadecenoate (17:1 n7) | 29743-97-3; | 5312435 | | | 5558 | 267.3 |
| stearate (18:0) | 57-11-4; | 5281 | C01530 | HMDB00827 | 1994.6 | 341.3 |
| oleate (18:1n9) | 112-80-1; | 445639 | C00712 | HMDB00207 | 1984.4 | 339.2 |
| cis-vaccenate (18:1n7) | 693-72-1; | 5282761 | C08367 | | 1987 | 339.3 |
| arachidate (20:0) | 506-30-9; | 10467 | C06425 | HMDB02212 | 2071.2 | 369.3 |
| eicosenoate (20:1 n9 or 11) | | | | HMDB02231 | 5955 | 309.4 |
| dihomo-linoleate (20:2n6) | 2091-39-6; | 6439848 | C16525 | | 5722 | 307.3 |
| arachidonate (20:4n6) | 506-32-1; | 444899 | C00219 | HMDB01043 | 5525 | 303.4 |
| docosadienoate (22:2n6) | 7370-49-2; | 5282807 | C16533 | | 6017 | 335.4 |
| lignocerate (24:0) | 557-59-5; | 11197 | C08320 | HMDB02003 | 2211 | 425.4 |
| n-Butyl Oleate | 142-77-8; | 5354342 | | | 2045 | 265.3 |
| 4-hydroxybutyrate (GHB) | 502-85-2; | 10413 | C00989 | HMDB00710 | 1277 | 233.1 |
| 2-hydroxystearate | 629-22-1; | 69417 | C03045 | | 5705 | 299.4 |
| 13-HODE | 29623-28-7; | 6443013 | C14762 | HMDB04667 | 5251 | 295.3 |
| 2-hydroxypalmitate | 764-67-0; | 92836 | | | 5508 | 271.3 |
| 2-hydroxyglutarate | 40951-21-1; | 43 | C02630 | HMDB00606 | 1576 | 247 |
| azelate (nonanedioate) | 123-99-9; | 2266 | C08261 | HMDB00784 | 1322 | 187.2 |
| undecanedioate | 1852-04-6; | 15816 | | HMDB00888 | 2376 | 215.1 |
| 3-carboxy-4-methyl-5-propyl-2-furanpropanoate (CMPF) | 86879-39-2; | 123979 | | | 2815 | 239.1 |
| 13-methylmyristic acid | 2485-71-4; | 151014 | | | 5498 | 241.3 |
| methyl palmitate (15 or 2) | | | | | 5698 | 269.4 |
| 17-methylstearate | 2724-59-6; | 3083779 | | | 5987 | 297.4 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | |
|---|---|---|---|---|---|---|
| 12-HETE | 73837-14-6; | | | HMDB06111 | 5295 | 319.3 |
| oleic ethanolamide | 11-58-0;111-58-0; | 5283454 | | HMBD02088 | 6553 | 324.5 |
| palmitoyl ethanolamide | | 4671 | | | 6416 | 298.4 |
| propionylcarnitine | 17298-37-2; | 107738 | C03017 | HMDB00824 | 1589 | 218.2 |
| butyrylcarnitine | 25576-40-3; | 213144 | | | 2007 | 232.2 |
| deoxycarnitine | 6249-56-5; | 725 | C01181 | HMDB01161 | 759 | 146.1 |
| carnitine | 461-05-2; | 10917 | | | 702 | 162.2 |
| 3-dehydrocarnitine* | 10457-99-5; | 6991982 | C02636 | HMDB12154 | 1020 | 160.2 |
| acetylcarnitine | 5080-50-2; | 7045767 | C02571 | HMDB00201 | 1203 | 204.2 |
| ethanolamine | 141-43-5; | | C00189 | HMDB00149 | 1074 | 102 |
| phosphoethanolamine | 1071-23-4; | 52,323,241,015 | C00346 | HMDB00224 | 1577.3 | 299.1 |
| glycerol | 56-81-5; | 753 | C00116 | HMDB00131 | 1311 | 205 |
| glycerol 3-phosphate (G3P) | 29849-82-9; | 754 | C00093 | HMDB00126 | 1719.7 | 357.1 |
| glycerophosphorylcholine (GPC) | 28319-77-9; | 657272 | C00670 | HMDB00086 | 694 | 258.1 |
| myo-inositol | 87-89-8; | | C00137 | HMDB00211 | 1924.9 | 217 |
| scyllo-inositol | 488-59-5; | | C06153 | HMDB06088 | 1893.8 | 318.2 |
| 1,2-propanediol | 57-55-6; | | C00717, C02912, C00583, C01506, C02917 | HMDB01881 | 1041 | 117 |
| 2-palmitoleoylglycerophosphoethanolamine* | | | | | 5611 | 450.3 |
| 1-stearoylglycerophosphoethanolamine | 69747-55-3; | 9547068 | | HMDB11130 | 6200 | 480.4 |
| 1-oleoylglycerophosphoethanolamine | | 9547071 | | HMDB11506 | 5928 | 478.3 |
| 2-oleoylglycerophosphoethanolamine* | | | | | 5848 | 478.3 |
| 1-linoleoylglycerophosphoethanolamine* | | | | HMDB11507 | 5725 | 476.3 |
| 2-linoleoylglycerophosphoethanolamine* | | | | | 5650 | 476.4 |
| 1-arachidonoylglycerophosphoethanolamine* | | | | HMDB11517 | 5731 | 500.3 |
| 2-arachidonoylglycerophosphoethanolamine* | | | | | 5674 | 500.3 |
| 1-palmitoylglycerophosphocholine | 17364-16-8; | 86554 | | | 6046 | 570 |
| 1-stearoylglycerophosphocholine | 19420-57-6; | 497299 | | | 5844 | 524.4 |
| 2-oleoylglycerophosphocholine* | | | | | 5640 | 522.4 |
| 1-oleoylglycerophosphoserine | | 9547099 | | | 5690 | 522.3 |
| 1-palmitoylplasmenylethanolamine* | | | | | 6153 | 436.4 |
| 1-stearoylglycerol (1-monostearin) | 123-94-4; | 24699 | D01947 | | 2186.6 | 399.4 |
| sphinganine | 3102-56-5; | 3126 | C00836 | HMDB00269 | 5175 | 302.3 |
| sphingosine | 123-78-4; | 5353955 | C00319 | HMDB00252 | 5197 | 300.2 |
| palmitoyl sphingomyelin | | 9939941 | | | 2524 | 311.3 |
| lathosterol | 80-99-9; | 65728 | C01189 | HMDB01170 | 2337 | 458.5 |
| cholesterol | 57-88-5; | 6432564 | C00187 | HMDB00067 | 2316.9 | 329.3 |
| dihydrocholesterol | 80-97-7; | 6665 | | HMDB00908 | 2320.8 | 215.2 |
| dehydroisoandrosterone sulfate (DHEA-S) | | 12594 | C04555 | HMDB01032 | 4771 | 367.2 |
| androsterone sulfate | 2479-86-9; | | C00523 | HMDB02759 | 5011 | 369.2 |
| 4-androsten-3beta,17beta-diol disulfate 1* | | | | HMDB03818 | 3735 | 224.3 |
| xanthine | 69-89-6; | 1188 | C00385 | HMDB00292 | 1889.9 | 353 |
| hypoxanthine | 68-94-0; | 790 | C00262 | HMDB00157 | 1313 | 135.1 |
| inosine | 58-63-9; | | | | 1630 | 267.2 |
| adenine | 73-24-5; | 190 | C00147 | HMDB00034 | 1003 | 136.1 |
| adenosine | 58-61-7; | 60961 | C00212 | HMDB00050 | 1650 | 268.1 |
| adenosine 5'-monophosphate (AMP) | 149022-20-8; | 15938965 | C00020 | HMDB00045 | 1210 | 348.1 |
| guanine | 73-40-5; | 764 | C00242 | HMDB00132 | 1022 | 152.1 |
| N2,N2-dimethylguanine | 1445-15-4; | 74047 | | | 1764 | 180 |
| guanosine | 118-00-3; | 6802 | C00387 | HMDB00133 | 1676 | 284 |
| 2'-O-methylguanosine | 2140-71-8; | | C04545 | | 1926 | 298 |
| urate | 69-93-; 2;120K5305 | | C00366 | HMDB00289 | 769 | 167.1 |
| thymine | 65-71-4; | 1135 | C00178 | HMDB00262 | 1429.1 | 255 |
| 3-aminoisobutyrate | 10569-72-9; | 64956 | C05145 | HMDB03911 | 1252.2 | 101.9 |
| uracil | 66-22-8; | 1174 | C00106 | HMDB00300 | 1370.4 | 241 |
| uridine | 58-96-8; | 6029 | C00299 | HMDB00296 | 1467 | 243.1 |
| pseudouridine | 1445-07-4; | | C02067 | HMDB00767 | 1104 | 243.1 |
| uridine monophosphate (5' or 3') | | | | | 1079 | 325 |
| ascorbate (Vitamin C) | 134-03-2; | | C00072 | HMDB00044 | 1850.1 | 332.1 |
| dehydroascorbate | 490-83-5; | 835 | C05422 | HMDB01264 | 1800 | 245.1 |
| heme* | 14875-96-8* | | | | 4985 | 616.2 |
| nicotinamide | 98-92-0; | 936 | C00153 | HMDB01406 | 1267 | 123.1 |
| nicotinamide adenine dinucleotide | 53-84-9; | 1,089,765,158, 925,280,000 | C00003 | HMDB00902 | 1370 | 664 |
| (NAD+)adenosine 5'diphosphoribose | 68414-18-6; | 4475880 | C00301 | HMDB01178 | 964 | 558.1 |
| nicotinate | 59-67-6; | 938 | C00253 | HMDB01488 | 1241 | 124.1 |
| pantothenate | 137-08-6; | 6613 | C00864 | HMDB00210 | 2218 | 220.1 |
| 3'-dephosphocoenzyme A | 3633-59-8; | 444485 | C00882 | HMDB01373 | 2010 | 686.2 |
| flavin adenine dinucleotide (FAD) | 146-14-5;84366-81-4; | 643975 | C00016 | HMDB01248 | 2413 | 784.1 |

TABLE 1-continued

Heat map of statistically significant biochemicals profiled. For paired comparisons, asterisks indicate p≤0.05
** indicate that the mean values are significantly higher for that comparison;* indicates values that are significantly
lower). Italicized text indicates 0.05 < p < 0.10.

| | | | | | | |
|---|---|---|---|---|---|---|
| riboflavin (Vitamin B2) | 83-88-5; | 493570 | C00255 | HMDB00244 | 3111 | 377.2 |
| alpha-tocopherol | 59-02-9; 10191-41-0; | 14985 | C02477 | HMDB01893 | 2305.4 | 502.5 |
| pyridoxate | 82-82-6; | 6723 | C00847 | HMDB00017 | 2210 | 182.1 |
| hippurate | 495-69-2; | 464 | C01586 | HMDB00714 | 2136 | 178.1 |
| 3-hydroxyhippurate | | 450268 | | HMDB06116 | 1670 | 194.1 |
| 4-hydroxyhippurate | 2482-25-9; | 151012 | | | 1439 | 194 |
| catechol sulfate | | 3083879 | C00090 | | 1928 | 188.9 |
| glycerol 2-phosphate | 819-83-0; | 2526 | C02979, D01488 | HMDB02520 | 1691.8 | 243 |
| heptaethylene glycol | 5617-32-3; | 79718 | | | 2836 | 327.2 |
| hexaethylene glycol | 2615-15-8; | 17472 | | | 2651 | 283.2 |
| octaethylene glycol | 5117-19-1; | 78798 | | | 3054 | 371.3 |
| pentaethylene glycol | 4792-15-8; | 62551 | | | 2471 | 239.2 |
| 2-pyrrolidinone | 616-45-5; | 12025 | | HMDB02039 | 1190.9 | 142 |
| 4-acetaminophen sulfate | 10066-90-7;32113-41-0; | 83939 | C06804 | HMDB01859 | 1779 | 230.1 |
| 4-acetamidophenol | 103-90-2; | 1983 | C06804 | HMDB01859 | 2238 | 152.1 |
| p-acetamidophenylglucuronide | 120595-80-4; | 4022661 | | HMDB10316 | 1377 | 326.1 |
| 2-hydroxyacetaminophen sulfate* | | | | | 1703 | 246.1 |
| 2-methoxyacetaminophen sulfate* | | | | | 1977 | 260.1 |
| 3-(cystein-S-yl)acetaminophen* | | 5233914 | | | 1960 | 271.2 |
| benzoylecgonine | 519-09-5; | 442997 | C10847 | | 3100.7 | 290.2 |
| saccharin | 81-07-2; | 5143 | D01085 | | 2013 | 182.1 |
| stachydrine | 4136-37-2; | 115244 | C10172 | HMDB04827 | 860 | 144.1 |
| caffeine | 58-08-2; | 2519 | C07481 | HMDB01847 | 2820 | 195.1 |
| paraxanthine | 611-59-6; | 4687 | C13747 | HMDB01860 | 2444 | 181.2 |
| theobromine | 83-67-0; | 5429 | C07480 | HMDB02825 | 2136 | 181.1 |
| 1,7-dimethylurate | 33868-03-0; | 91611 | C16356 | HMDB11103 | 1607 | 195.1 |
| erythritol | 149-32-6; | | C00503 | HMDB02994 | 1517.5 | 217 |

Having described the invention in detail, it will be apparent that modifications, variations, and equivalent embodiments are possible without departing from the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Experiments ("Cohort A")

Study population and sample collection: The initial study population was derived from two clinic sites in Seattle with enrollment between November 2003 and June 2010: the Public Health, Seattle and KingCounty Sexually Transmitted Diseases Clinic (STD clinic; n=30) and the University of Washington's Women's Research Clinic (WRC; n=30). A case-control study comprising 40 women with BV and 20 women without BV was conducted. BV was defined by both Amsel criteria (21) and Gram stain interpretation using the Nugent method (22); women were classified BV-negative if negative by both diagnostic measures. Cases and controls were randomly selected from both clinics in a 2:1 ratio, with the goal of having a better representation of women with BV given the increased bacterial heterogeneity associated with this condition. All women provided written informed consent, and the studies were approved by Review Boards at the Fred Hutchinson Cancer Research Center and the University of Washington.

Studies were aimed at using mass spectrometry to link specific metabolites with particular bacteria detected in the human vagina by PCR. BV was associated with strong metabolic signatures across multiple pathways affecting amino acid, carbohydrate and lipid metabolism, highlighting the profound metabolic changes in BV. These signatures were associated with the presence and concentrations of particular vaginal bacteria including some bacteria yet to be cultivated, thereby providing clues as to the microbial origin of many metabolites.

A pelvic examination with speculum was performed for collection of samples. Polyurethane foam swabs (Epicenter Biotechnologies, Madison, Wis.) were brushed against the lateral vaginal wall and stored at −80° C. until DNA extraction for bacterial PCRs. Vaginal fluid was also collected for Gram staining, pH, saline microscopy and potassium hydroxide preparation. Cervicovaginal lavage fluid (CVL) was collected by instilling 10 mL sterile saline into the vagina, aspirating, and storing at −80° C. prior to processing for metabolomics studies.

DNA Extraction and quantitative PCR: DNA was extracted using the Ultra Clean Soil DNA Kit or the Bacteremia Kit (Mobio, Carlsbad, Calif.), which gave similar results. DNA was eluted in 150 μL buffer and diluted 1:1 in 1 mM Tris, 0.1 mM EDTA (TE) buffer. Sham swabs without human contact were processed as controls to assess contamination from reaction buffers or sample collection swabs. Samples were evaluated for presence of PCR inhibitors using a qPCR assay targeting a segment of exogenously added jellyfish DNA; inhibition was defined as a delay in the threshold cycle of >2 cycles compared with no template controls (68). Control assays targeting the human 18S rRNA gene were performed to ensure that swabs contained human tissue (68). DNA from each sample was subjected to a panel of 14 qPCR assays to measure concentrations of bacteria. The bacteria targeted included three members of the Clostridiales order which are highly specific for BV, designated BV-associated bacterium-1 (BVAB-1), BVAB-2, and BVAB-3 (8). Other vaginal bacteria targeted included *Gardnerella vaginalis, Leptotrichia/Sneathia* spp., *Megasphaera*-like bacterium (Type 1 & Type 2), *Atopobium vaginae, Lactobacillus crispatus, Lactobacillus jensenii*, and *Lactobacillus iners* (69, 70). Four additional qPCR assays targeting an *Eggerthella*-like bacterium, *Prevotella amnii, Prevotella timonensis* and *Prevotella buccalis* using 16S rRNA gene-specific primers and taxon-directed hydrolysis probes were developed. Assay conditions, primer and probe sequences for qPCR assays developed in this study are presented in Table 2. Core PCR reagents were obtained from Applied Biosystems (Carlsbad, Calif.), and master mixes contained buffer A (1 mM), deoxynucleotide triphosphates (1 mM), magnesium (3 mM), AmpErase uracil-N-glycosylase (0.05 U), and AmpliTaq Gold polymerase (1-1.5 U) per reaction. Primers were added at 0.8 per reaction and final probe concentration was 150 µM. Assays underwent 45 cycles of amplification on the StepOnePlus™ Real-time PCR System (Life Technologies, Grand Island, N.Y.). Plasmid standards were run in duplicate from 106 to 2.5 copies. Specificity and sensitivity testing was conducted as previously described (69). Two microliters of DNA (diluted 1:1 with TE buffer) were added to each qPCR reaction and values are reported as 16S rRNA gene copies per swab.

Broad-range PCR and pyrosequencing of 16S rRNA gene amp/icons: Broad-range 16S rRNA gene PCR with pyrosequencing was performed using 454 Life Sciences FLX technology (Roche, Branford, Conn.) targeting the V3-V4 region of the 16S-rRNA gene for a subset of samples from 20 women with BV and 10 women without BV, a subset of the cohort described previously (11). Sequence reads were classified using a phylogenetic placement tool pplacer (71) and a curated reference set of vaginal bacteria (11). All sequence reads were deposited in the NCBI Short Red Archive (5RA051298) (11). Measurement of levels of biochemicals: Chromatographic separation and full-scan mass spectroscopy (MS) were performed using the Metabolon (Durham, N.C.) platform (72-74). Briefly, CVL samples were extracted to remove the protein fraction while allowing maximal recovery of small molecules using the MicroLab STAR® system (Hamilton, Reno, Nev.). The resulting extract was split into equal parts for analysis by gas chromatography/mass spectrometry (GC/MS) and liquid chromatography/mass spectrometry (LC/MS). Samples were dried by placing them on a Zymark TurboVap® (American Laboratory Trading, East Lyme Conn.) and stored at −80° C. Aliquots of water and solvents used in the extraction were included as controls to assess the contribution of the separation process and extraction methods to the compound signals. Additional samples with known compositions were also included with every run to ensure that there were no process deviations in each run. A reference library of 1000 purified standards with known chemical structures was used to identify the small molecules from the samples by matching chromatographic properties and mass spectral signatures.

Data analysis: Metabolite data were median-centered, and missing values imputed as the minimum observed for that metabolite; median values were then log-transformed. Pyrosequencing taxonomic counts and qPCR measures were log-transformed. Welch's two sample t-tests were used to

TABLE 2

Primer and probe sequences

| PCR Assay | PCR Conditions | Amplicon Size | Primer/Probe | Primer/Probe Sequence |
|---|---|---|---|---|
| Eggerthella-like | 56° C. annealing, 39 s | 84 bp | Egger-like_126F | 5'-GACCAACCTGCCTCTTACATT-3' |
| | 72° C. extension, 30 s | | Egger-like_210R | 5'-G CATACATCATGTG ATATGTG C-3' |
| | | | Egger-like_155-178_pb | 5'-FAMAAAAGAAATTCTGGCTAATACCAA-MG BN FQ-3' |
| Prevotella buccalis | 57° C. annealing, 39 s | 171 bp | Pbuccalis_455F | 5'-G CG CGACGTGTCGTG CA-3' |
| | 72° C. extension, 30 s | | Pbuccalis_626R | 5'-CCGGTTGAGCCGGTACA-3' |
| | | | P.buccalis_587-604_pb | 5'-FAM-CG CCAG RTAAG CGTGTTGMG BN FQ-3' |
| Prevotella timonensis | 64° C. anneal/extend, 60 | 90 bp | Ptimonensis_578F | 5'-GAG CGTAG G CTGTCTATTAAG C-3' |
| | | | Ptimonensis_668R | 5'-CTTCCTG CATACTCAAGTCG A C |
| | | | Ptimonensis_609-629_pb | 5'-FAM-ATTTACCGGCTCAACCGGTGGMG BN FQ-3' |
| Prevotella amnii | 59° C. annealing, 39 s | 69 bp | Pamnii_989F | 5'-GGCTTGAATTG CAGATGTTTATAT-3' |
| | 72° C. extension, 30 s | | Pamnii_1058R | 5'-CCATGCAGCACCTTCACAAAT-3' |
| | | | Pamnii_1014-1033_pb | 5'-FAM-AG ATGATATATTCCCTTCG G-MG BN FQ-3' |

Figure 2:
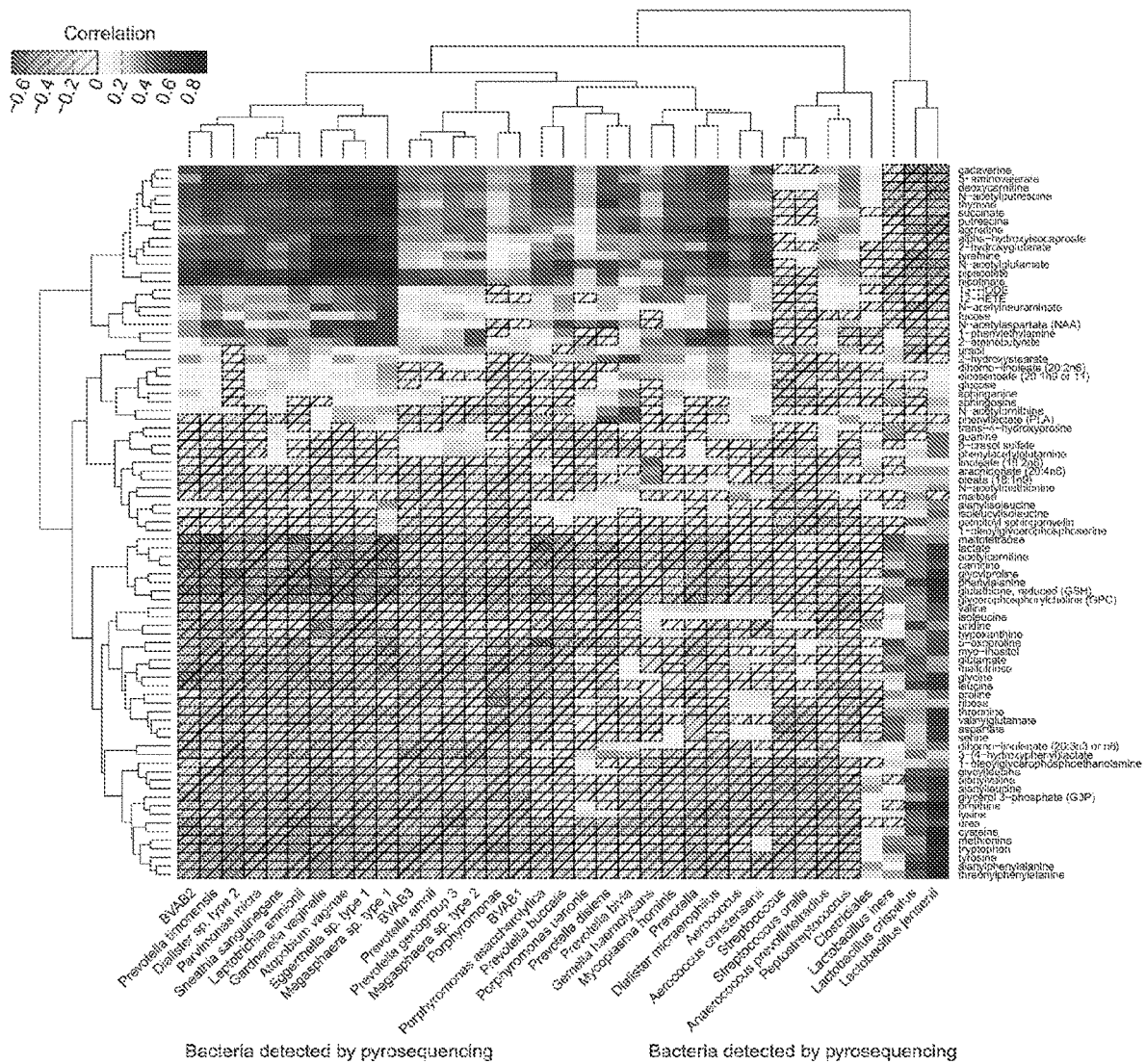
FIG. 2 depicts the association between metabolites and bacterial abundance. Hierarchically clustered Pearson correlation coefficients are displayed in a heat map to demonstrate associations of vaginal bacteria (relative abundance) detected using broad-range PCR and pyrosequencing (x-axis) with the abundance of 30% most variable metabolites (y-axis). Correlation values ranged from −0.7 to 0.84.
Figure 3:
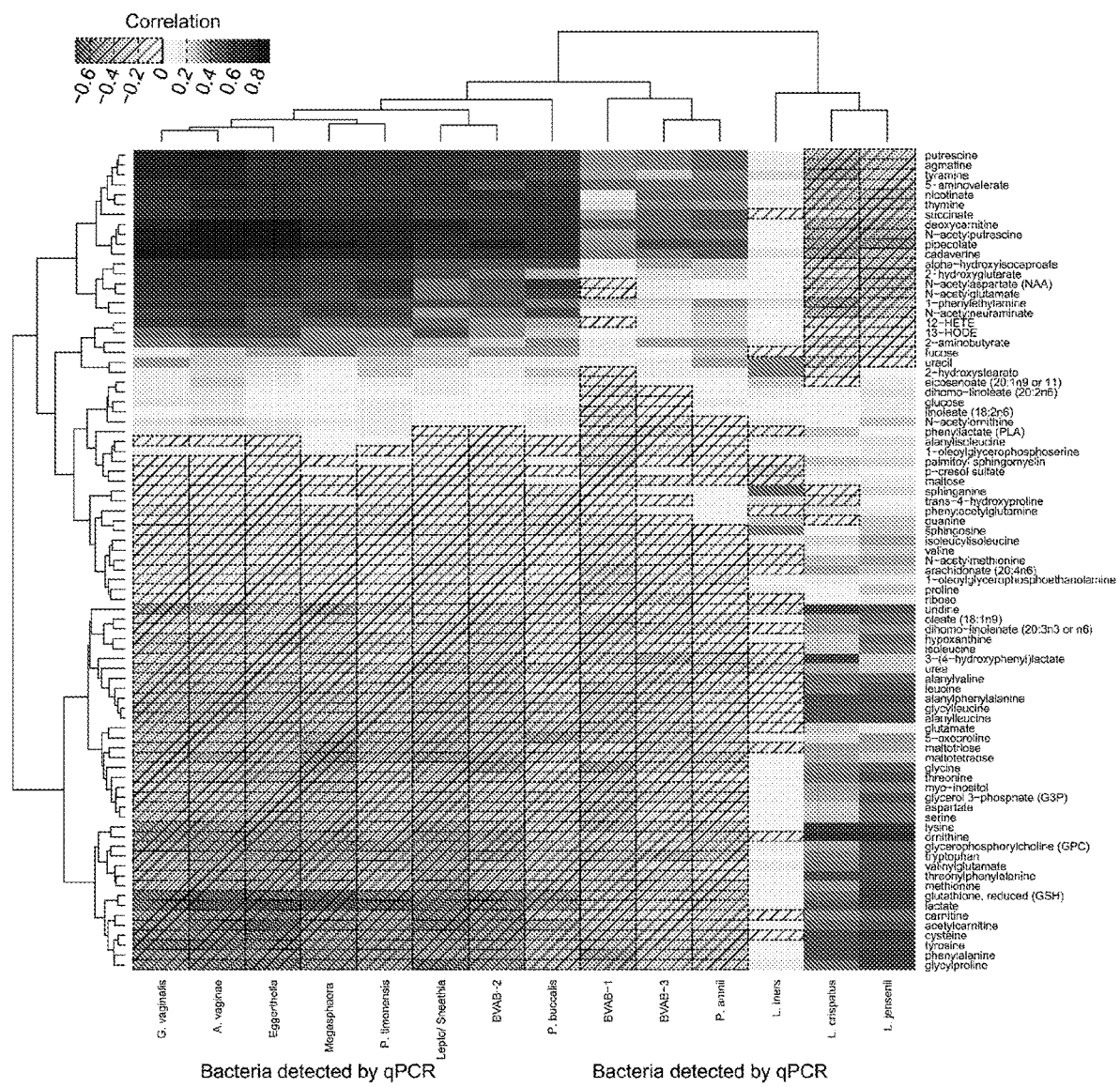
FIG. 3 depicts the association of specific vaginal bacteria with metabolites. Hierarchically clustered Pearson correlation coefficients are displayed in a heat map to demonstrate associations of key vaginal bacterial concentrations (x-axis) measured using taxon directed qPCR with the 30% most variable metabolites (y axis). Correlation values range from −0.71 to 0.85. Two sub-groups of BV associated bacteria were observed, and clustering patterns were similar to that noted in FIG. 2 using untargeted approach for bacterial community analysis. *L. crispatus* and *L. jensenii* exhibited correlation patterns that were similar and opposite to those by BV-associated bacteria.

MG-Minor groove binder, FAM-fluorescein label, BNFQ-Black Hole Non-fluorescent quencher compare metabolites between BV-positive and BV-negative groups. An estimate of false discovery rate (q-value) was calculated to account for multiple comparisons. A low q-value (<0.1) indicates high confidence in a result. Eighty-three metabolites (30%) with largest variability (inter-quartile range) were used to hierarchically cluster samples using Euclidean distance (FIG. 1); identification of four sample groups maximizes silhouette width. To explore the relationship between relative abundances of metabolite and pyrosequencing reads (FIG. 2) or qPCR measures (FIG. 3), Pearson correlations were calculated between metabolite and pyrosequencing reads or qPCR levels; these were used in hierarchical clustering using Euclidean distance. Data transformation was performed in R (http://crans-project.org) (75). Lasso regression with binomial response was used to identify metabolites strongly associated with Amsel clinical criteria (Table 3). The number of metabolites retained was set to the largest value within 1 standard deviation of the cross-validation error. Analysis was performed with the R package glmnet (76).

TABLE 3

Association of metabolites with individual clinical criteria

| Bacterial Taxa | Regression co-efficient' |
|---|---|
| BV Status | |
| deoxycarnitine | 0.5 |
| phenylalanine | −0.299 |
| N-acetylputrescine | 0.254 |
| pipecolate | 0.148 |
| cadaverine | 0.025 |
| Elevated pH | |
| cadaverine | 0.0657 |
| N-acetylputrescine | 0.0577 |
| lactate | −0.0505 |
| glutamate | −0.0249 |

TABLE 3-continued

Association of metabolites with individual clinical criteria

| Bacterial Taxa | Regression co-efficient' |
|---|---|
| sphingosine | −0.0137 |
| tyrosine | −0.0083 |
| tyramine | 0.0033 |
| Presence of Clue Cells | |
| deoxycarnitine | 0.2519 |
| glycylproline | −0.203 |
| glutathione, reduced (GSH) | −0.0311 |
| pipecolate | 0.0024 |
| Presence of Amine Odor | |
| N-acetylputrescine | 0.302 |
| lactate | −0.072 |
| phenylalanine | −0.049 |
| Vaginal Discharge | |
| agmatine | 0.14 |
| cadaverine | 0.11 |

Metabolite Summary of Cohort A

Characteristics of the 60 women from cohort A are presented in Table 4. There was low prevalence of other infections including *Candida* (8%), *Trichomonas vaginalis* (3%), *Chlamydia trachomatis* (3%), and *Neisseria gonorrhoeae* (0%). Cases included women with BV by both Amsel criteria and Nugent score; controls did not have BV by both criteria. Elevated pH>4.5 was the only Amsel criterion noted in all cases (n=40); vaginal fluid from 20% of control women had pH>4.5 (n=4). Presence of >20% clue cells and a positive whiff test (amine odor) were both observed in 83% of cases (n=33); clue cells and a positive whiff test were not detected in the control group. A thin homogeneous discharge that is present in some women with symptomatic BV was noted in 85% of cases (n=34), and 5% (n=1) of women in the control group.

TABLE 4

Characteristics of study participants according to case or control status

| | Cohort A | | | Cohort B | | |
|---|---|---|---|---|---|---|
| Characteristic | Total (n = 60) | Cases (n = 40) | Controls (n = 20) | Total (n = 60) | Cases (n = 40) | Controls (n = 20) |
| Age, Median (range) | 26 (17-56) | 26 (19-42) | 26 (17-56) | 29 (19-49) | 29 (19-45) | 30 (21-49) |
| Race (self-defined)[1] | | | | | | |
| Black or African American | 13 (22) | 10 (25) | 3 (15) | 24 (40) | 22 (55) | 2 (10) |
| White | 41 (68) | 27 (68) | 14 (70) | 28 (47) | 14 (35) | 14 (70) |
| Other | 4 (7) | 2 (5) | 2 (10) | 7 (12) | 4 (10) | 3 (15) |
| Don't Know/Declined to provide data | 2 (3) | 1 (3) | 1 (5) | 1 (1) | 0 (0) | 1 (5) |
| Menses, at visit | 4 (7) | 3 (8) | 1 (5) | 5 (8) | 4 (10) | 1 (5) |
| Vaginal douching, past week[2] | 4 (7) | 3 (8) | 1 (5) | 3 (5) | 2 (5) | 1 (5) |
| Antibiotic use, past month[3] | 5 (8) | 5 (13) | 0 (0) | 5 (8) | 3 (7.5) | 2 (10) |
| Hormonal contraceptive, past month[4] | 7 (60) | 3 (8) | 4 (20) | 18 (30) | 9 (23) | 9 (45) |
| Sexual activity | | | | | | |
| Sex, past 3 months[5] | 55 (92) | 37 (93) | 18 (90) | 50 (83) | 33 (83) | 17 (85) |
| Sex with female partner[6] | 13 (22) | 9 (23) | 4 (20) | 9 (15) | 7 (18) | 2 (10) |
| Sex with male partner[7] | 50 (83) | 33 (83) | 17 (85) | 49 (82) | 34 (85) | 15 (75) |
| Amsel criterion - Vaginal Discharge[8] | | | | | | |
| Normal | 18 (30) | 5 (13) | 13 (65) | 18 (30) | 0 (0) | 18 (90) |
| Abnormal | 35 (58) | 34 (85) | 1 (5) | 35 (58) | 34 (85) | 1 (5) |
| Other | 7 (11) | 1 (3) | 6 (30) | 7 (12) | 6 (15) | 1 (5) |
| Amsel criterion - pH | | | | | | |
| 4.5 and less | 16 (27) | 0 (0) | 16 (80) | 16 (27) | 1 (2) | 15 (75) |
| Greater than 4.5 | 44 (73) | 40 (100) | 4 (20) | 44 (73) | 39 (98) | 5 (25) |

TABLE 4-continued

Characteristics of study participants according to case or control status

| Characteristic | Cohort A | | | Cohort B | | |
|---|---|---|---|---|---|---|
| | Total (n = 60) | Cases (n = 40) | Controls (n = 20) | Total (n = 60) | Cases (n = 40) | Controls (n = 20) |
| Amsel criterion - Clue Cells | | | | | | |
| Absent | 21 (35) | 2 (5) | 19 (95) | 18 (30) | 0 (0) | 18 (90) |
| Less than 20% (few) | 5 (8) | 4 (10) | 1 (5) | 4 (7) | 2 (5) | 2 (10) |
| Greater than 20% (many) | 33 (55) | 33 (83) | 0 (0) | 38 (63) | 38 (95) | 0 (0) |
| Amsel criterion - Whiff Test | | | | | | |
| Negative | 27 (45) | 7 (18) | 20 (100) | 28 (47) | 8 (20) | 20 (100) |
| Positive | 33 (55) | 33 (83) | 0 (0) | 32 (53) | 32 (80) | 0 (0) |
| Other infections | | | | | | |
| *Trichomonas vaginalis* | 2 (3) | 2 (5) | 0 (0) | 1 (2) | 1 (2) | 0 (0) |
| *Chlamydia trachomatis*[9] | 2 (3) | 1 (3) | 1 (5) | 0 (0) | 0 (0) | 0 (0) |
| *Neisseria gonorrhoeae*[9] | 0 (0) | 0 (0) | 0 (0) | 0 (0) | 0 (0) | 0 (0) |
| *Candida* | 5 (8) | 1 (3) | 4 (20) | 4 (7) | 3 (8) | 1 (5) |

Data represent number (%) of participants. Cases included women with BV by both Amsel criteria (21) and by interpretation of Gram stain using Nugent score (22). Controls included women who did not have BV by both criteria.
[1]Study participants were able to select more than one category for race. Black/African American and white indicate women who selected only these categories.
[2]Douching data not available for 1 study participant who did not provide data.
[3]Antibiotic use data not available for 4 study participants.
[4]Hormonal contraceptive data not available for 4 study participants who did not provide data.
[5]Sex data not available for 2 study participants who did not provide data.
[6]Female sex partner data not available for 9 study participants who did not provide data.
[7]Male sex partner data not available for 2 study participants who did not provide data.
[8]Abnormal vaginal discharge indicates those with a thin homogenous discharge that is consistent with BV. Women with vaginal discharge that was not normal, or did not have a thin homogeneous discharge were placed in the other category.
[9]*Chlamydia trachomatis* and *Neisseria gonorrhoeae* data not available for 5 study participants.

279 known metabolites was detected in vaginal fluid from women with and without BV. There were significant differences in levels of 173 metabolites (62% of the 279 detected) on comparison of women with and without BV (q-value=0.02). Women with BV had higher levels of 55 biochemicals (20%), and lower levels of 118 biochemicals (42%). A summary of metabolites altered in BV based on pathway is provided in Table 5.

TABLE 5

Summary of biochemicals altered based on super pathways

| Super Pathway[1] | Total Altered | Biochemicals higher in BV Number (%) | Biochemicals lower in BV Number (%) |
|---|---|---|---|
| Amino Acid | 90 | 32 (35.6) | 35 (38.9) |
| Peptide | 28 | 0 (0.0) | 24 (85.7) |
| Carbohydrate | 27 | 3 (11.1) | 15 (55.6) |
| Energy | 6 | 2 (33.3) | 0 (0.0) |
| Lipid | 74 | 12 (16.2) | 27 (26.5) |
| Nucleotide | 17 | 3 (17.6) | 8 (47.1) |
| Cofactors & Vitamins | 13 | 3 (23.1) | 6 (46.2) |
| Xenobiotics | 24 | 0 (0.0) | 3 (12.5) |

[1]Biochemicals categorized according to KEGG pathways.

Hierarchical clustering depicting this set of the most variable metabolites measured in CVL samples from all women resulted in the creation of four groups, of which 2 clusters were populated by women with BV. Cluster-I had 12 women without BV, and Cluster-II comprised 15 women with BV. Cluster-III included women without BV. Cluster-IV included 25 women with BV and 1 woman without BV (Subject 58) (FIG. 1). Vaginal fluid from Subject 58, the outlier in Cluster-IV, had an elevated pH of 5.6 and a Nugent score of 6, defined as intermediate on this scale.

Example 3

Alterations in Metabolism ("Cohort A")

Amino acids: 19 of 20 important amino acids (95%) that are incorporated into proteins were detected using the Metabolon platform (Table 1). Levels of 18 of 19 amino acids detected (94.7%) were lower among cases; this was statistically significant for 16 of 18 amino acids (84.9%). There were higher concentrations of amino acid catabolites in women with BV (Table 1). Examples of such catabolites include: cadaverine ($p<0.001$) and pipecolate ($p<0.001$) in the lysine degradation pathway; tyramine ($p<0.001$), 4-hydroxyphenylacetate ($p<0.001$) and 3-(4-hydroxyphenyl)propionate ($p<0.001$) in the tyrosine pathway; tryptamine ($p<0.001$) in the tryptophan pathway; and citrulline ($p<0.001$) in the arginine pathway. There was marked elevation of the polyamine putrescine ($p<0.001$), along with lower levels of putrescine precursors arginine ($p<0.001$) and ornithine ($p<0.001$) in women with BV. The polyamine spermine ($p<0.001$), a typical product of putrescine degradation, was lower in BV. Enhanced protein/amino acid catabolism in BV was further supported by detection of lower levels of dipeptides (n=28); this was statistically significant for 24 dipeptides (85.7%). Levels of oxidized ($p<0.001$) and reduced ($p=0.049$) glutathione were lower in BV.

Carbohydrates: Of the four aminosugars detected, N-acetylneuraminate, commonly known as sialic acid, was higher in BV ($p<0.001$), while glucosamine levels were lower ($p=0.0059$). Glucose oligosaccharides of varying length including maltotriose ($p=0.0095$), maltotetraose ($p=0.0016$), maltopentaose ($p<0.001$), and maltohexaose ($p<0.001$) were all lower in BV. Likewise, lower levels of simple sugars and sugar alcohols such as lactate ($p<0.001$), fructose ($p=0.0012$), and mannitol ($p=0.001$) were noted;

galactose (p<0.001) and threitol (p<0.001) were significantly higher in BV. Succinate levels were also higher in BV (p<0.001).

Nicotinamide adenine dinucleotide (NAD): NAD, an essential co-factor for energy metabolism, was below the limit of detection in 82.5% of BV cases and in only 10% of controls (p<0.001). Nicotinamide levels, a precursor to NAD biosynthesis, were also lower in BV (p=0.06), while nicotinate (p=0.002) levels were higher.

Lipids: Multiple components of lipid metabolism were affected in BV. The arachidonic acid catabolite 12-hydroxyeicosatetraenoic acid (12-HETE) was higher in BV (p<0.001) while arachidonate was lower (p=0.0075). Deoxycarnitine, a precursor to carnitine was higher in BV (p<0.001), while carnitine was lower (p<0.001). Ascorbic acid, which is essential to the synthesis of carnitine, was lower in BV (p<0.001). Acyl-carnitines such as acetylcarnitine (p<0.001), propionylcarnitine (p<0.001), and butyryl carnitine (p<0.001) were also lower in BV. Of the four monohydroxy fatty acids detected, levels of 4-hydroxybutyrate (p<0.001) and 13-hydroxyoctadecadienoic acid (13-HODE) (p=0.0042) were higher in BV. Biochemicals involved in glycerol metabolism including glycerol (p=0.046) and glycerol-3-phosphate (p<0.001) were lower in BV.

Example 4

Association Between Metabolites and Bacterial Abundance and Concentrations in Cohort A Association between metabolites and bacterial abundance: Pearson correlation coefficients were used to investigate associations between bacterial abundance and metabolite abundance in vaginal samples. Specifically, the abundance of 30% of the most variable metabolites and relative abundance of bacteria detected by broad-range PCR with pyrosequencing was analyzed in a subset of 20 women with BV and 10 women without BV. A group of ten BV-associated bacteria were highly correlated with metabolites typically associated with BV including succinate, cadaverine, putrescine, tyramine and deoxycarnitine (FIG. 2). *Megasphaera* sp. type 1 had the highest correlation coefficient with the fatty acid, 12-HETE (0.48). A second cluster of BV-associated bacteria including BVAB1, BVAB3, *Megasphaera* sp. type 2 and several *Prevotella* species such *P. amnii, P. disiens, P. buccalis* and *P. bivia* showed similar positive associations with the above-mentioned metabolites, but the correlations were less pronounced. The three lactobacilli, *L. crispatus, L. jensenii* and *L. iners* clustered together and exhibited metabolite correlation patterns that overall were in contrast to the patterns found with BV-associated bacteria.

Association between metabolites and bacterial concentrations: Bacteria were selected for qPCR based on relative abundance measured by broad-range PCR and pyrosequencing in a subset of samples (FIG. 2), and on associations made in previous studies that have demonstrated sensitivity, specificity (31) and significance of these bacteria in BV (11, 20, 32). Associations of concentrations of key vaginal bacteria with the 30% most variable metabolites were investigated using Pearson correlation coefficients (FIG. 3). *L. crispatus, L. jensenii* and *L. iners* clustered together, while the BV-associated bacteria clustered as two groups. Group-1 comprised *Leptotrichia/Sneathia* spp., BVAB2, *Megasphaera* spp., *Prevotella timonensis, Atopobium vaginae, Gardnerella vaginalis, Eggerthella*-like bacterium and *Prevotella buccalis*. Group-2 comprised BVAB1, BVAB3 and *Prevotella amnii*. Clustering patterns noted here also reflected patterns observed in the association analysis of metabolites with bacteria detected by broad range PCR and pyrosequencing. *L. crispatus* and *L. jensenii*, lactobacilli typically associated with vaginal health, exhibited metabolite correlation patterns that were similar; these were in striking contrast to those exhibited by BV-associated bacteria (FIG. 3). *L. iners* exhibited correlation patterns that were intermediate between those of BV-associated bacteria and those of *L. crispatus/L. jensenii*. Concentrations of *L. crispatus* and *L. jensenii* had strong positive correlations with several amino acids and dipeptides, but were negatively correlated with amino acid catabolites (tyramine, pipecolate, cadaverine) and polyamines (putrescine, agmatine). *L. iners* was negatively correlated with some amino acids and dipeptides (glutamate, glycylleucine), but positively correlated with others (proline, threonine, aspartate, serine, and valinylglutamate). *L. crispatus* and *L. jensenii* were positively correlated with sugars such as maltose, maltotriose, and maltohexose, lipid metabolism biochemicals such as arachidonate and carnitine, as well as lactate, urea, and reduced glutathione. These two lactobacilli were negatively correlated with N-acetylneuraminate, succinate, the carnitine precursor deoxycarnitine, the eicosanoid 12-HETE, the fatty acid 13-HODE, and the nucleobase uracil. BV-associated bacteria typically exhibited correlation patterns with metabolites that were opposite to that exhibited by *L. crispatus* and *L. jensenii*. Among BV-associated bacteria, BVAB1 displayed specific differences in metabolite correlation patterns when compared with BV-associated bacteria from Group-1. BVAB1 was negatively correlated with N-acetylaspartate, 12-HETE, fatty acids such as eicosenoate and dihomo linoleate; these metabolites had positive associations with Group-1 BV-associated bacteria. BVAB3 and *P. amnii*, members of Group-2 BV-associated bacteria, exhibited metabolite correlation patterns that were similar to each other.

Example 5

Alterations in Key Vaginal Bacteria and Metabolite Concentration with Changes in BV Status in Cohort 1

Figure 5:
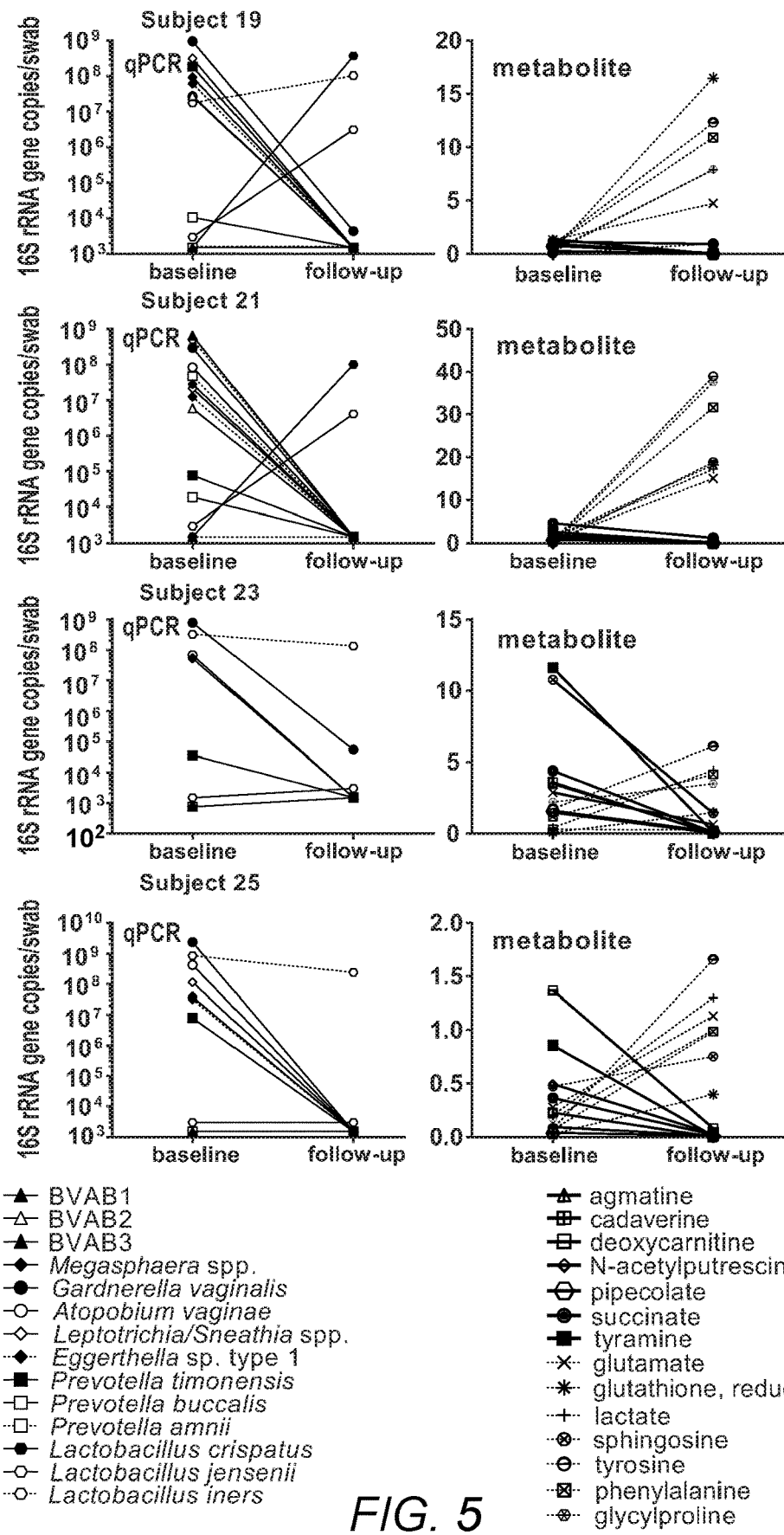
FIG. 5 depicts shifts in concentrations of key vaginal bacteria and metabolites with treatment for BV. Longitudinal data is presented for four study participants (19, 21, 23 & 25) who were cured of BV post treatment with metronidazole at the one month follow-up visit. Bacterial concentrations are displayed as 16S rRNA copies per swab on the y-axis of the XY-plots. Scaled metabolite concentrations (y-axis) of 14 metabolites associated with individual clinical criteria (from FIG. 4 & Table 3) have been classified as positively associated with BV and are higher in women BV and negatively associated with BV and are lower in women with BV. Y-axis scales are different for each subject reflecting differences in metabolite concentrations. All four participants had high concentrations of lactobacilli at their follow-up visits and increased concentrations of metabolites negatively associated with BV. Women with high concentrations of *L. crispatus* at follow-up had high concentrations of metabolites negatively associated with BV. Women with high concentrations of *L. iners* also showed increased concentrations of metabolites negatively associated with BV, but these shifts were not as dramatic as increases seen in women with *L. crispatus* dominant communities.
Figure 6A:
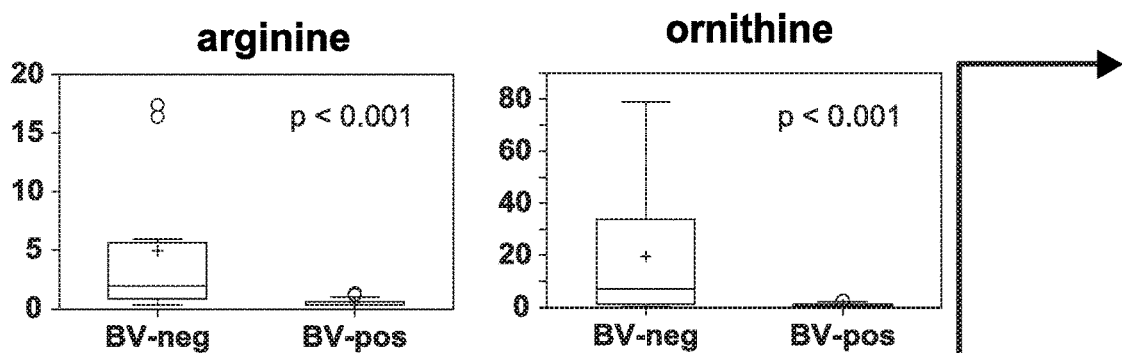
FIG. 6 is a model representing putative putrescine metabolism pathways in bacterial vaginosis. Box plots show selected metabolites that were detected in studies. BV status is indicated on the x-axis of box plots. The y-axis of box plots represent scaled concentrations of metabolites. The lines in box plots depict the mean, and whiskers denote 95% confidence intervals. Arginine typically serves as a precursor for the generation of polyamines putrescine, spermidine and spermine. Levels of putrescine were higher in BV, while levels of spermine were lower. Higher levels of succinate are a hallmark in BV. Recently, a novel putrescine utilization pathway has been discovered in *Escherichia coli* via γ-aminobutaraldehyde (GABA), resulting in succinate production. Higher levels of N acetylputrescine were observed in BV, which can also lead to GABA formation. Arrows next to metabolites indicate metabolites detected in the Examples, and show whether concentrations were higher or lower in women with BV.
Figure 6A:
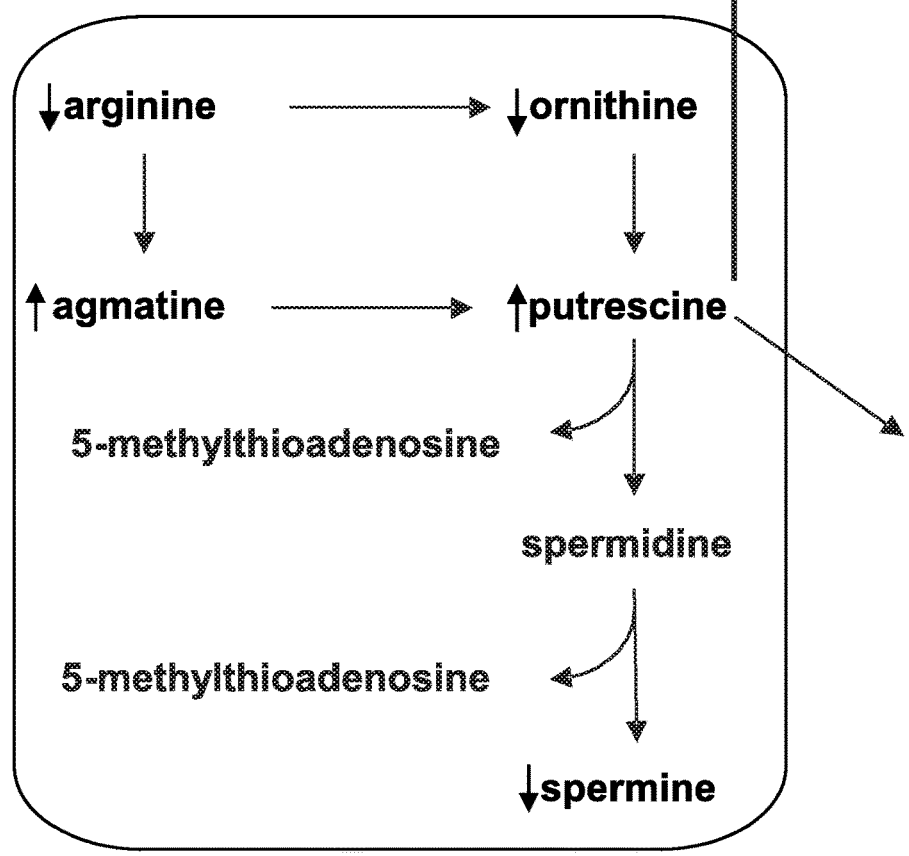
Figure 6A:
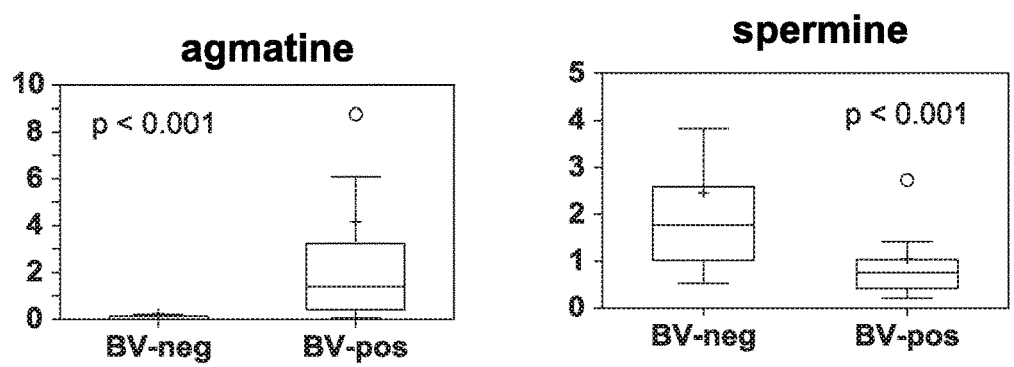
Figure 6B:
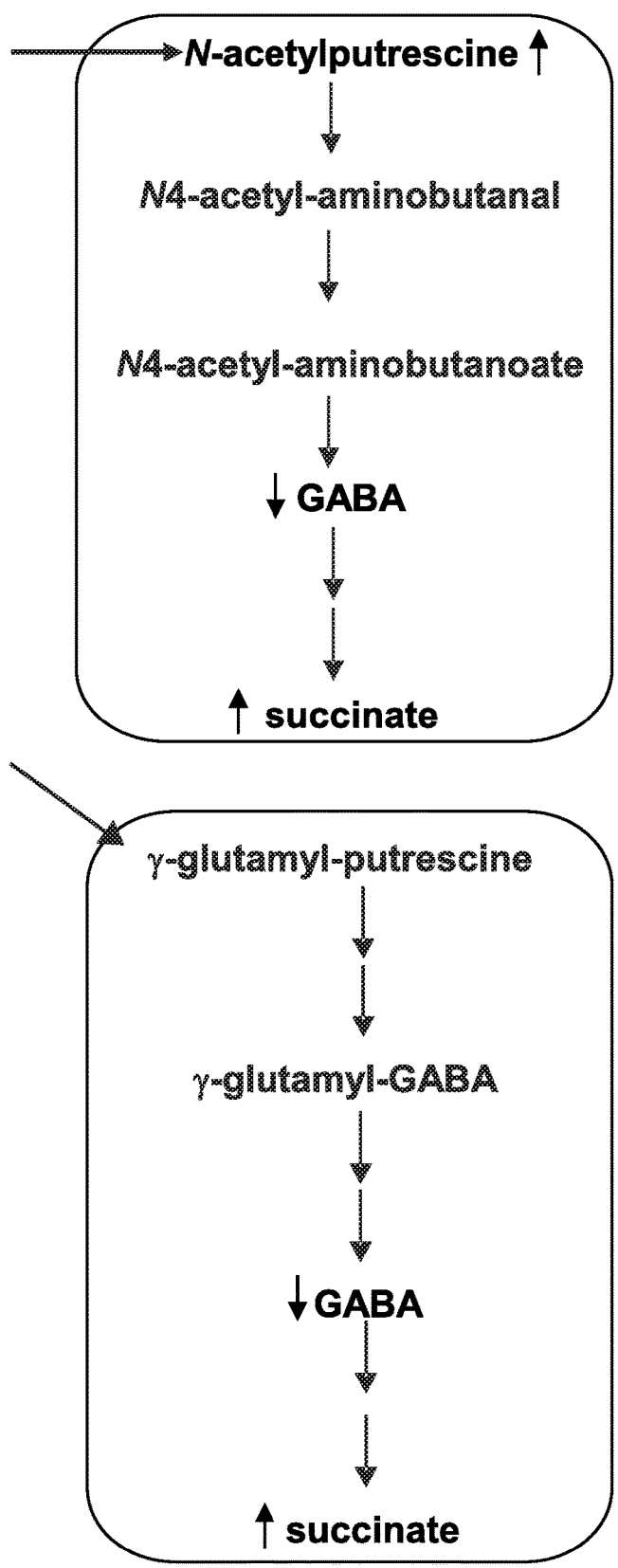
Figure 6B:
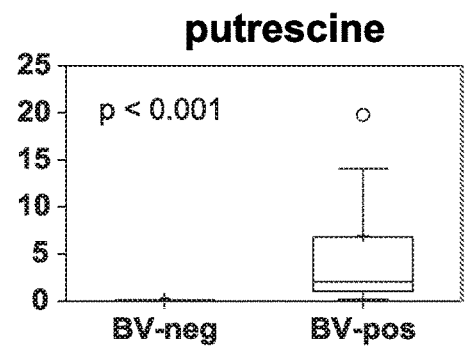
Figure 6B:
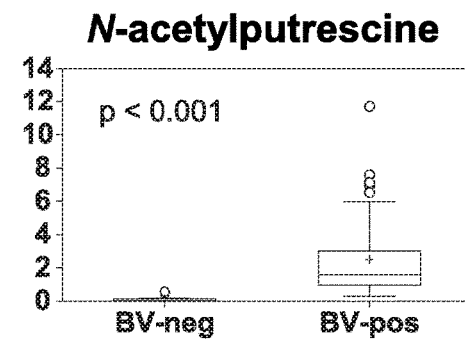
Figure 6B:
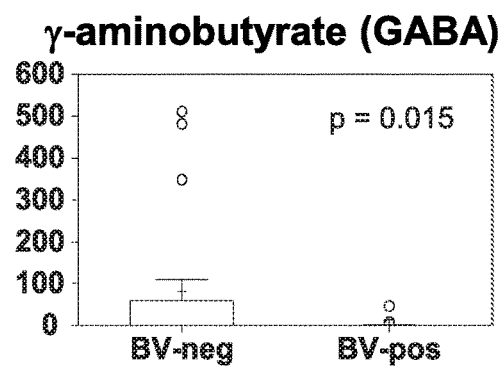
Figure 6B:
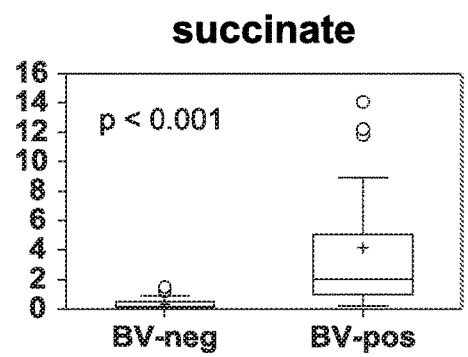
Figure 7A:
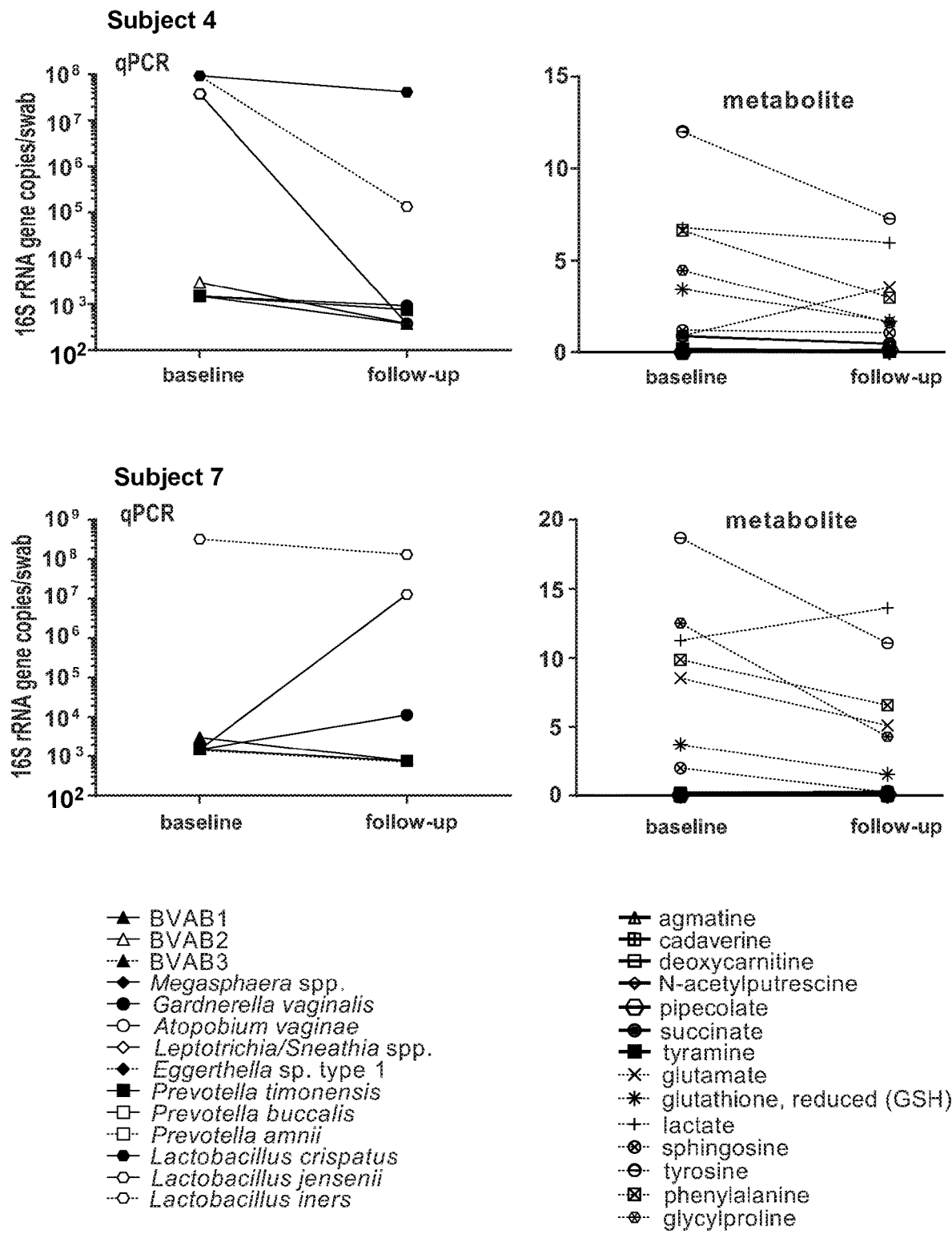
FIG. 7 is a group of graphs depicting bacteria and metabolite concentrations in women with no changes in BV status. Limited longitudinal data are presented for 4 women who returned for follow-up visits 4 weeks after baseline sample collection per study protocol. BV status was evaluated by Amsel criteria and confirmed by Gram stain. Participants diagnosed with BV were treated with metronidazole. Bacterial concentrations are displayed as 16S rRNA copies per swab on the y-axis of the XY-plots. Scaled metabolite concentrations (y-axis) of 14 metabolites associated with individual clinical criteria (from FIG. 4 & Table 3) have been classified as positively associated with BV and negatively associated with BV. Y-axis scales are different for each subject reflecting differences in metabolite concentrations. (A) Study participants 4 and 7 did not have BV at either time point and had high concentrations of lactobacilli at both time points. High concentrations of metabolites negatively associated with BV were also noted at baseline and follow-up. (B) Study participants 12 and 28 had recurrent BV. In both participants, concentrations of metabolites associated with BV declined at the follow-up visit, but there was no associated increase in metabolites negatively associated with BV. This longitudinal analysis showed that stability of the microbiota was associated with few shifts in metabolites even after patients received antibiotic therapy.
Figure 7B:
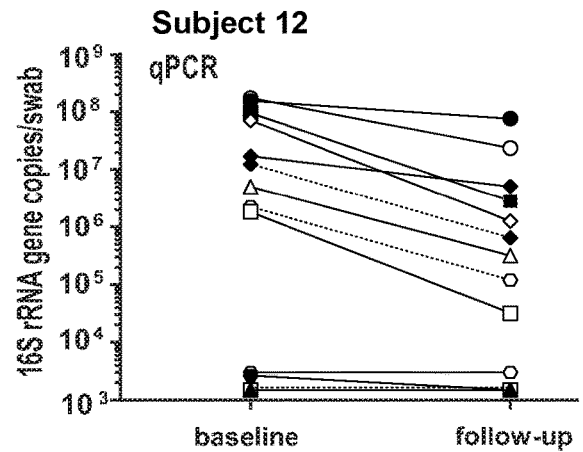
Figure 7B:
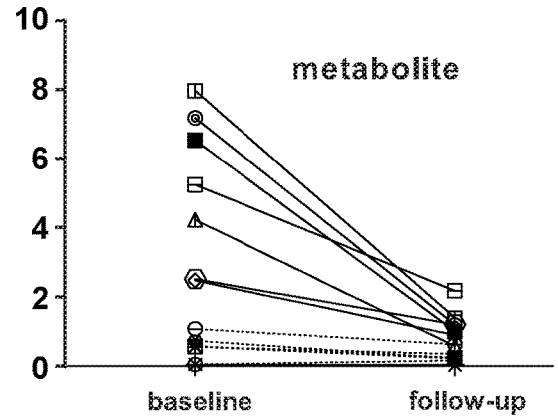
Figure 7B:
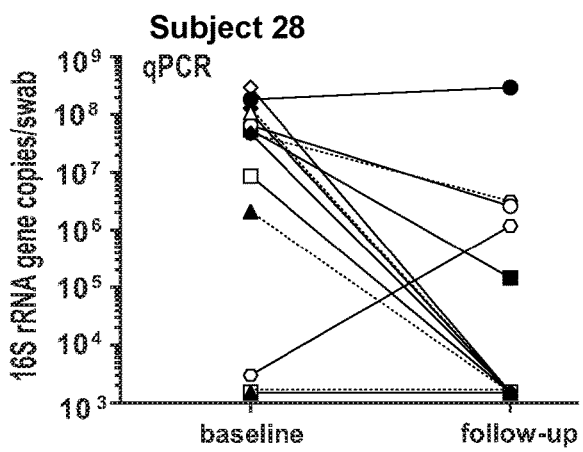
Figure 7B:
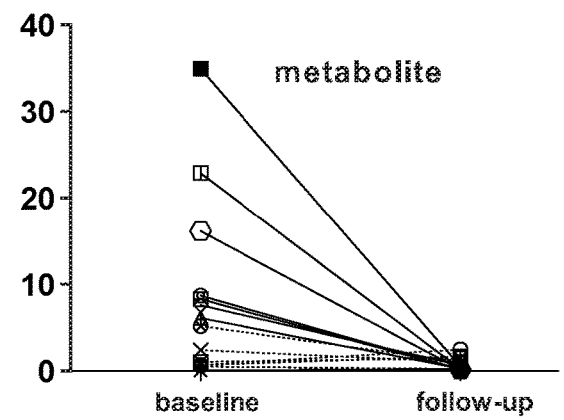

Limited longitudinal data are presented for 8 women who returned for follow-up visits 4 weeks after baseline sample collection per study protocol (FIG. 5, FIG. 7). Participants diagnosed with BV were treated with metronidazole. Study participants 19, 21, 23 and 25 were cured of BV at the follow-up visit (FIG. 5). All four participants had high concentrations of lactobacilli at their follow-up visits and increased concentrations of metabolites negatively associated with BV. Women with high concentrations of *L. crispatus* at follow-up had high concentrations of metabolites negatively associated with BV. Women with high concentrations of *L. iners* also showed increased concentrations of metabolites negatively associated with BV, but these shifts were not as dramatic as increases seen in women with *L. crispatus* dominant communities (FIG. 5). Study participants 4 and 7 did not have BV at either time point and had high concentrations of lactobacilli at both time points (FIG. 7). High concentrations of metabolites negatively associated with BV were also noted at baseline and follow-up. Study participants 12 and 28 had recurrent BV after antibiotic treatment. In both participants, concentrations of metabolites associated with BV declined at the follow-up visit, but there was no associated increase in metabolites negatively associated with BV (FIG. 7). In this longitudinal analysis, changes in the microbiota were associated with shifts in metabolites in the same subject, whereas stability of the microbiota was associated with fewer changes even after patients received antibiotic therapy.

Example 6

Validation Study (Cohort B)

Study population and sample collection: Cohort B in the independent validation study also comprised 40 women with BV and 20 women without BV enrolled in the STD clinic between April 2011 and August 2013. BV definitions and sample collection procedures were the same as Cohort A. An additional 10 women with intermediate (4-6) Nugent scores were included to determine if their metabolite profiles differed from those who had BV (Nugent 7-10) or those who had scores of Nugent 0-3. Of these 10 women, 6 were BV negative and 4 were BV positive by Amsel clinical criteria. All women provided written informed consent, and the study was approved by Institutional Review Board at the Fred Hutchinson Cancer Research Center.

DNA Extraction and molecular methods: DNA was extracted using the Bacteremia Kit (Mobio, Carlsbad, Calif.) and eluted in 150 µL buffer and diluted 1:1 in 1 mM Tris, 0.1 mM EDTA (TE) buffer. The V3-V4 region of the 16S-rRNA gene was targeted for broad-range 16S-rRNA gene PCR with pyrosequencing using 454 Life Sciences Titanium technology (Roche, Branford, Conn.). Reads were processed using the same methods as Cohort A, and reads were deposited in the NCBI Short Red Archive (SRP056030).

Measurement of levels of biochemicals: Sample preparation: Commercially available pooled serum (Innovative Research, Novi, Mich.) was used as quality control (QC) sample and aqueous metabolites were extracted using methanol (250 The supernatant (200 µL) obtained post-centrifugation (20,800×g for 10 min) was dried for 90 min using a Vacufuge Plus evaporator (Eppendorf, Hauppauge, N.Y.) and reconstituted in 600 µL 40% Solvent A (40 mM ammonium acetate in $H_2O$+0.3% acetic acid) and 60% Solvent B (acetonitrile+0.3% acetic acid) containing 5.13 µM L-tyrosine-$^{13}C_2$ and 22.54 µM sodium-L-lactate-$^{13}C_3$ (Cambridge Isotope Laboratory). The isotope-labeled internal standards helped monitor LC-MS assay performance. Samples were filtered through 0.45 pm PVDF filters (Phenomenex, Torrance, Calif.) prior to LC-MS analysis. Acetonitrile, ammonium acetate, methanol, and acetic acid (LC-MS grade) were obtained from Fisher Scientific (Pittsburgh, Pa.) and stable isotope-labeled tyrosine and lactate internal standards (>99% pure) from Cambridge Isotope Laboratories, Inc. (Tewksbury, Mass.). The QC sample was injected every 10 vaginal samples. Vaginal swab samples and CVL (100 µL) were processed using the same procedure as the QC sample, but extracted using 850 µL of methanol. Sham samples (saline solution and swabs without human contact) were included to assess background signals (chemical impurities present in materials used to collect vaginal fluid). Blank saline solution and swab samples were injected once each for every 10 vaginal fluid samples.

Chromatography Conditions: The LC system was composed of two Agilent 1260 binary pumps, an Agilent 1260 auto-sampler and Agilent 1290 column compartment containing a column-switching valve (Agilent Technologies, Santa Clara, Calif.). Each sample was injected twice, 10 µL for analysis using negative ionization mode and 2 µL for analysis using positive ionization mode. Both chromatographic separations were performed in HILIC mode on two parallel SeQuant ZIC-cHILIC columns (150×2.1 mm, 3.0 pm particle size, Merck KGaA, Darmstadt, Germany). While one column was performing the separation, the other column was reconditioning in preparation for the next injection. The flow rate was 0.300 mL/min, auto-sampler temperature was kept at 4° C., the column compartment was set at 40° C., and total separation time for each ionization mode was 18 min. The mobile phase was composed of Solvents A and B; the gradient conditions for both separations were identical and are as follows: 0-2 min, 25% Solvent A, 75% Solvent B; 2-5 min, 25 to 70% Solvent A, linear gradient; 5-9 min, 70% Solvent A; 9-11 min 70 to 25% Solvent A, linear gradient; 11-18 min, 25% Solvent A.

Mass Spectrometry (MS) and data processing: After the chromatographic separation, MS ionization and data acquisition were performed using an AB Sciex QTrap 5500 mass spectrometer (AB Sciex, Toronto, ON, Canada) equipped with electrospray ionization (ESI) source. The instrument was controlled by Analyst 1.5 software (AB Sciex, Toronto, ON, Canada). Targeted data acquisition was performed in multiple-reaction-monitoring (MRM) mode. Additional assays for 19 metabolites of interest based on results from Cohort A were developed wherein biochemicals using the Metabolon platform (Table 6) were measured. 104 and 76 MRM transitions in negative and positive mode, respectively, were monitored (180 transitions total) (Table 6). The source and collision gas was N2 (99.999% purity). The ion source conditions in negative mode were: Curtain Gas (CUR)=25 psi, Collision Gas (CAD)=high, Ion Spray Voltage (IS)=−3.8 KV, Temperature (TEM)=500° C., Ion Source Gas 1 (GS1)=50 psi and Ion Source Gas 2 (GS2)=40 psi. The ion source conditions in positive mode were: Curtain Gas (CUR)=25 psi, Collision Gas (CAD)=high, Ion Spray Voltage (IS)=3.8 KV, Temperature (TEM)=500° C., Ion Source Gas 1 (GS1)=50 psi and Ion Source Gas 2 (GS2)=40 psi. The extracted MRM peaks were integrated using MultiQuant 2.1 software (AB Sciex, Toronto, ON, Canada). Standard compounds corresponding to measured metabolites were purchased from Sigma-Aldrich (Saint Louis, Mo., USA) and Fisher Scientific (95-99% pure).

Data analysis: Metabolite data and pyrosequencing reads were processed and analyzed as described for Cohort A.

TABLE 6

Cohort B - University of Washington NW-MRC Platform

| Biochemical Name | Platform | Comp ID | KEGG | HMDB | Mean Values Neg | Mean Values Pos | Welch's Two Sample t-Test Pos/Neg p-value | Welch's Two Sample t-Test Pos/Neg q-value | Fold Change Pos/Neg | Super Pathway | Measured using Metabolon Platform |
|---|---|---|---|---|---|---|---|---|---|---|---|
| 12-HETE | LC/MS neg | 5312983 | C14777 | HMDB06111 | 0.549761 | 2.153909 | 0.0058 | 0.0225 | 3.918** | Lipid | Yes |
| 13-HODE | LC/MS neg | 5282948 | C14767 | HMDB61708 | 0.296921 | 4.872555 | 0.0004 | 0.0023 | 16.410** | Lipid | Yes |
| 1-Methyladenosine | LC/MS pos | 27476 | C02494 | HMDB03331 | 13.89231 | 1.019602 | 0.2533 | 0.3109 | 0.073 | Nucleotide | No |
| 2-Aminoadipate | LC/MS neg | 469 | C00956 | HMDB00510 | 1.083608 | 1.236384 | 0.5614 | 0.6032 | 1.141 | Amino Acid | Yes |
| 2-Hydroxyglutarate | LC/MS pos | 43 | C02630 | HMDB59655 | 3.932806 | 1.095001 | 0.0389 | 0.0655 | 0.278 | Lipid | Yes |
| 4-Hydroxybutyrate | LC/MS pos | 10413 | C00989 | HMDB00710 | 0.949666 | 1.009497 | 0.1147 | 0.1655 | 1.063 | Lipid | Yes |
| 5-Aminovaleric Acid | LC/MS neg | 138 | C00431 | HMDB03355 | 0.099272 | 3.554135 | <0.001 | <0.001 | 35.802** | Amino Acid | Yes |
| Adenine | LC/MS neg | 190 | C00147 |  | 1.42114 | 0.997052 | 0.3296 | 0.3871 | 0.702 | Nucleotide | Yes |
| Adenosine | LC/MS neg | 60961 | C00212 | HMDB00050 | 2.789559 | 0.829478 | 0.0190 | 0.0392 | 0.297* | Nucleotide | Yes |
| Adenylosuccinate | LC/MS neg | 195 | C03794 | HMDB00536 | 2.850905 | 1.945559 | 0.4879 | 0.5415 | 0.682 | Nucleotide | No |
| Adipic Acid | LC/MS neg | 196 | C06104 | HMDB00448 | 0.969576 | 1.041395 | 0.3615 | 0.4197 | 1.074 | Caprolactam Degradation | No |
| Alanine | LC/MS neg | 5950 | C00041 | HMDB00161 | 1.837288 | 0.955452 | 0.1784 | 0.2435 | 0.520 | Amino Acid | Yes |
| Allantoin | LC/MS pos | 204 | C01551 | HMDB00462 | 1.512457 | 0.908111 | 0.1484 | 0.2082 | 0.600 | Nucleotide | No |
| Alpha-Ketoglutaric Acid | LC/MS neg | 51 | C00026 | HMDB00208 | 0.973055 | 1.024005 | 0.5515 | 0.5989 | 1.052 | Energy | No |
| AMP | LC/MS neg | 15938965 | C00020 | HMDB00045 | 2.399105 | 0.886976 | 0.0053 | 0.0225 | 0.370* | Nucleotide | Yes |
| Anthranilate | LC/MS pos | 227 | C00152 | HMDB01123 | 2.854806 | 0.943821 | 0.0137 | 0.0337 | 0.331* | Amino Acid | No |
| Arachidonate | LC/MS neg | 5960 | C00049 | HMDB60102 | 1.034647 | 0.975074 | 0.0160 | 0.0377 | 0.942* | Lipid | Yes |
| Arginine | LC/MS pos | 232 | C00062 | HMDB00517 | 5.047576 | 0.863601 | 0.0065 | 0.0233 | 0.171* | Amino Acid | Yes |
| Ascorbic Acid (Vit. C) | LC/MS neg | 54670067 | C00072 | HMDB00044 | 1.777006 | 9069.362 | 0.7750 | 0.7987 | 0.760 | Cofactors and Vitamins | No |
| Asparagine | LC/MS pos | 6267 | C00152 | HMDB00168 | 19.02775 | 1.777006 | 0.0257 | 0.0509 | 0.093* | Amino Acid | Yes |
| Aspadic Acid | LC/MS neg | 5960 | C00049 | HMDB00191 | 4.385856 | 0.750243 | 0.0165 | 0.0379 | 0.171* | Amino Acid | No |
| Biotin | LC/MS neg | 171548 | C00120 | HMDB00030 | 4.346047 | 0.965599 | 0.0681 | 0.1090 | 0.222 | Cofadors and Vitamins | Yes |
| Cadaverine | LC/MS pos | 273 | C01672 | HMDB02322 | 0.050142 | 3.857881 | <0.001 | <0.001 | 76.940** | Amino Acid | No |
| Carnitine | LC/MS pos | 2724480 | C00487 | HMDB00062 | 3.279169 | 0.764733 | 0.0274 | 0.0521 | 0.233* | Lipid | Yes |
| Choline | LC/MS pos | 305 | C00114 | HMDB00097 | 2.077764 | 1.520472 | 0.5026 | 0.5517 | 0.732 | Cofactors and Vitamins | No |
| Citraconic Acid | LC/MS neg | 643798 | C02226 | HMDB00634 | 1.018945 | 1.092198 | 0.3098 | 0.3681 | 1.072 | Amino Acid | Yes |
| Citrulline | LC/MS pos | 833 | C00327 | HMDB00904 | 1.667773 | 0.977009 | 0.2058 | 0.2598 | 0.586 | Amino Acid | No |
| Creatine | LC/MS pos | 586 | C00300 | HMDB00064 | 2.444336 | 0.842549 | 0.0104 | 0.0309 | 0.345* | Amino Acid | Yes |
| Creatinine | LC/MS pos | 588 | C00791 | HMDB00562 | 2.874441 | 0.953764 | 0.0347 | 0.0603 | 0.332 | Amino Acid | Yes |
| Cystamine | LC/MS pos | 2915 | N/A | N/A | 2.252528 | 0.949694 | 0.0690 | 0.1090 | 0.422 | Amino Acid | No |
| Cysteine | LC/MS pos | 5862 | C00097 | HMDB00574 | 12.56652 | 1.389119 | 0.0279 | 0.0522 | 0.111* | Amino Acid | Yes |
| Cystine | LC/MS pos | 67678 | C00491 | HMDB00192 | 11.15403 | 0.579027 | 0.0145 | 0.0349 | 0.052* | Amino Acid | No |
| Cytosine | LC/MS pos | 597 | C00380 | HMDB00630 | 1.312866 | 1.543991 | 0.7135 | 0.7586 | 1.176 | Nucleotide | No |
| Dimethylglycine | LC/MS pos | 673 | C01026 | HMDB00092 | 0.918006 | 2.008823 | 0.0294 | 0.0529 | 2.188** | Cofactors and Vitamins | No |
| D-Leucic Acid | LC/MS neg | 439960 | C03264 | HMDB00624 | 0.746823 | 4.282549 | 0.0131 | 0.0336 | 5.734** | Amino Acid | No |
| Epinephrine | LC/MS pos | 5816 | C00788 | HMDB00068 | 1.038287 | 0.952361 | 0.0498 | 0.0824 | 0.917 | Amino Acid | No |
| Erythrose | LC/MS neg | 439574 | C01796 | HMDB02649 | 1.208405 | 1.314378 | 0.4795 | 0.5381 | 1.088 | Carbohydrate | No |
| F16P/F26BP/G16BP | LC/MS neg | 172313/ 105021/ 82400 | C00354/ C00665/ C01231 | HMDB01058/ HMDB01047/ HMDB03514 | 2.395754 | 0.864547 | 0.0009 | 0.0046 | 0.361 | Carbohydrate | Yes |

TABLE 6-continued

Cohort B - University of Washington NW-MRC Platform

| Biochemical Name | Platform | Comp ID | KEGG | HMDB | Mean Values Neg | Mean Values Pos | Pos/Neg Welch's Two Sample t-Test p-value | Pos/Neg Welch's Two Sample t-Test q-value | Pos/Neg Fold Change | Super Pathway | Measured using Metabolon Platform |
|---|---|---|---|---|---|---|---|---|---|---|---|
| Fumaric Acid/Maleic Acid | LC/MS neg | 444972/ 444266 | C00122/ C01384 | HMDB00134/ HMDB00176 | 1.030087 | 1.09067 | 0.4138 | 0.4696 | 1.059 | Energy | Yes |
| G1P/G6P/F6P/F1P | LC/MS neg | 439165/ 5958/ 69507/ 10400369 | C00103/ C000921 C00085/ C01094 | HMDB01586/ HMDB01401/ HMDB00124/ HMDB01076 | 1.014726 | 1.302086 | 0.2004 | 0.2595 | 1.283 | Carbohydrate | Yes |
| Gluconate | LC/MS neg | 444791 | C00191 | HMDB00127 | 3.565885 | 0.862001 | 0.0039 | 0.0177 | 0.242* | Carbohydrate | No |
| Glucose | LC/MS neg | 79025 | C00031 | HMDB00122 | 3.2199 | 0.582469 | <0.001 | <0.001 | 0.181* | Carbohydrate | Yes |
| Glutamic acid | LC/MS neg | 611 | C00025 | HMDB03339 | 3.943463 | 0.950986 | 0.0081 | 0.0264 | 0.241* | Amino Acid | Yes |
| Glutamine | LC/MS pos | 5961 | C00303 | HMDB00641 | 2.096949 | 0.920155 | 0.0851 | 0.1283 | 0.439 | Amino Acid | Yes |
| Glutaric Acid | LC/MS neg | 743 | C00489 | HMDB00661 | 0.483471 | 1.974837 | <0.001 | 0.0001 | 4.085** | Amino Acid | No |
| Glyceraldehyde | LC/MS neg | 751 | C02426 | HMDB01051 | 0.597584 | 1.553495 | <0.001 | 0.0001 | 2.600** | Carbohydrate | Yes |
| Glycerate | LC/MS neg | 752 | C00258 | HMDB00139 | 1.841234 | 1.003125 | 0.0750 | 0.1148 | 0.545 | Carbohydrate | Yes |
| Glycerol-3-P | LC/MS neg | 754 | C00093 | HMDB00126 | 0.420476 | 1.980146 | <0.001 | <0.001 | 4.709** | Lipid | Yes |
| Glycine | LC/MS pos | 750 | C00037 | HMDB00123 | 3.851766 | 0.854576 | 0.0289 | 0.0529 | 0.222* | Amino Acid | Yes |
| Guanidinoacetate | LC/MS neg | 763 | C00581 | HMDB00128 | 2.062227 | 1.084617 | 0.1909 | 0.2537 | 0.526 | Amino Acid | No |
| Guanosine | LC/MS pos | 6802 | C00387 | HMDB00133 | 5.489016 | 0.849731 | 0.0389 | 0.0655 | 0.155 | Nucleotide | Yes |
| Histamine | LC/MS pos | 774 | C00388 | HMDB00870 | 0.360377 | 5.06166 | <0.001 | <0.001 | 14.045** | Amino Acid | Yes |
| Histidine | LC/MS pos | 6274 | C00768 | HMDB00177 | 3.183509 | 0.991506 | 0.0127 | 0.0336 | 0.311* | Amino Acid | Yes |
| Homovanilate | LC/MS neg | 1738 | C05582 | HMDB00118 | 1.061823 | 1.063368 | 0.9792 | 0.9663 | 1.001 | Amino Acid | No |
| Hypoxanthine | LC/MS neg | 790 | C00262 | HMDB00157 | 2.5559 | 0.792758 | 0.0133 | 0.0336 | 0.310* | Nucleotide | Yes |
| iso-Leucine | LC/MS pos | 791 | C00407 | HMDB00172 | 2.822668 | 0.886257 | 0.0112 | 0.0319 | 0.314* | Amino Acid | Yes |
| Kynurenate | LC/MS neg | 3845 | C01717 | HMDB00715 | 0.861798 | 1.163729 | 0.1817 | 0.2446 | 1.350 | Amino Acid | Yes |
| Lactate | LC/MS neg | 612 | C001861 | HMDB00190 | 1.529119 | 0.521579 | <0.001 | <0.001 | 0.341* | Carbohydrate | Yes |
| Leucine | LC/MS pos | 6106 | C00123 | HMDB00687 | 3.152967 | 0.687161 | 0.0009 | 0.0046 | 0.218* | Amino Acid | Yes |
| Linolenic Acid | LC/MS neg | 5280450 | C01595 | HMDB00673 | 1.514934 | 1.302946 | 0.7589 | 0.7901 | 0.860 | Lipid | Yes |
| Lysine | LC/MS pos | 5962 | C00047 | HMDB00182 | 7.517767 | 0.753601 | 0.0071 | 0.0245 | 0.100* | Amino Acid | Yes |
| Malonic Acid/3HBA | LC/MS neg | 867/441 | C00383/ C01089 | HMDB00691/ HMDB00357 | 0.894359 | 1.181646 | 0.0116 | 0.0319 | 1.321** | Energy | No |
| Methionine | LC/MS pos | 6137 | C01733 | HMDB00696 | 10.96199 | 1.212818 | 0.0188 | 0.0392 | 0.111* | Amino Acid | Yes |
| MethylSuccinate | LC/MS neg | 10349 | C08645 | HMDB01844 | 14.1235 | 1.039721 | 0.0060 | 0.0226 | 0.074* | Amino Acid | No |
| N-Acetylneuraminate | LC/MS neg | 445063 | C00270 | HMDB00230 | 0.359184 | 1.490695 | <0.001 | 0.0001 | 4.150** | Carbohydrate | Yes |
| N-Acetylputrescine | LC/MS pos | 122356 | C02714 | HMDB02064 | 0.332351 | 5.445013 | 0.0008 | 0.0046 | 16.383*** | Amino Acid | No |
| Niacinamide | LC/MS pos | 936 | C00153 | HMDB01406 | 1.771045 | 1.271236 | 0.4096 | 0.4696 | 0.718 | Cofactors and Vitamins | Yes |
| Nicotinate (Niacin) | LC/MS neg | 938 | C00253 | HMDB01488 | 0.916006 | 1.026653 | 0.0656 | 0.1069 | 1.121 | Cofactors and Vitamins | No |
| Ornithine | LC/MS pos | 6262 | C01602 | HMDB03374 | 14.05848 | 0.768175 | 0.0087 | 0.0275 | 0.055* | Amino Acid | Yes |
| Oxalic Acid | LC/MS neg | 971 | C00209 | HMDB02329 | 3.292335 | 0.619838 | 0.0003 | 0.0018 | 0.188* | Carbohydrate | No |
| Oxaloacetate | LC/MS neg | 970 | C00036 | HMDB00223 | 0.87623 | 1.162188 | 0.1093 | 0.1600 | 1.326 | Energy | No |
| Oxidized glutathione | LC/MS neg | 975 | C00127 | HMDB03337 | 2.985064 | 1.499132 | 0.1624 | 0.2247 | 0.502 | Amino Acid | Yes |
| Oxypurinol | LC/MS neg | 4644 | C07599 | HMDB00786 | 0.255491 | 1.923879 | 0.0000 | 0.0000 | 7.530** | Nucleotide | No |
| Pantothenate | LC/MS neg | 6613 | C00864 | HMDB00210 | 2.612067 | 1.311789 | 0.2381 | 0.2969 | 0.502 | Cofactors and Vitamins | Yes |
| PEP | LCMS nag | 1005 | C00074 | HMDB00263 | 0.94683 | 2.131465 | 0.0250 | 0.0505 | 2.251** | Carbohydrate | No |
| Phenylalanine | LC/MS pos | 6140 | C02057 | HMDB00159 | 4.386514 | 0.568173 | 0.0001 | 0.0004 | 0.130* | Amino Acid | Yes |

TABLE 6-continued

Cohort B - University of Washington NW-MRC Platform

| Biochemical Name | Platform | Comp ID | KEGG | HMDB | Mean Values Neg | Mean Values Pos | Welch's Two Sample t-Test Pos/Neg p-value | Welch's Two Sample t-Test Pos/Neg q-value | Fold Change Pos/Neg | Super Pathway | Measured using Metabolon Platform |
|---|---|---|---|---|---|---|---|---|---|---|---|
| Pipecolate | LC/MS pos | 6931663 | C00408 | HMDB00070 | 7.316458 | 0.69474 | 0.0180 | 0.0392 | 0.095* | Amino Acid | Yes |
| Proline | LC/MS pos | 145742 | C00148 | HMDB00162 | 2.313779 | 1.453898 | 0.2626 | 0.3157 | 0.628 | Amino Acid | Yes |
| Propionate | LC/MS neg | 1032 | C00163 | HMDB00237 | 0.898881 | 1.848487 | 0.0999 | 0.1485 | 2.056 | Carbohydrate | No |
| Putrescine | LC/MS pos | 1045 | C00134 | HMDB01414 | 0.087085 | 2.737776 | <0.001 | <0.001 | 31.438** | Amino Acid | Yes |
| Pyruvate | LC/MS nag | 1060 | C00022 | HMDB00243 | 1.601785 | 1.049359 | 0.1999 | 0.2595 | 0.655 | Carbohydrate | Yes |
| Reduced glutathione | LC/MS neg | 124886 | C00051 | HMDB00125 | 5.968484 | 1.030784 | 0.0267 | 0.0519 | 0.173* | Amino Acid | Yes |
| Ribose-5-P | LC/MS neg | 439167 | C00117 | HMDB01548 | 1.034082 | 1.011506 | 0.7387 | 0.7772 | 0.978 | Carbohydrate | No |
| Serine | LC/MS pos | 5951 | C00065 | HMDB00187 | 5.933157 | 0.782622 | 0.0185 | 0.0392 | 0.132* | Amino Acid | Yes |
| Shikimic Acid | LC/MS nag | 8742 | C00493 | HMDB03070 | 3.145483 | 1.477166 | 0.1259 | 0.1791 | 0.470 | Amino Acid | No |
| Sorbitol | LC/MS pos | 107428 | C00794 | HMDB00247 | 9.470836 | 0.684095 | 0.0073 | 0.0245 | 0.072* | Carbohydrate | Yes |
| Spemidine | LC/MS pos | 1102 | C00315 | HMDB01257 | 1.065615 | 1.11261 | 0.8640 | 0.8815 | 1.044 | Amino Acid | Yes |
| Succinate/Methylmalonate | LC/MS neg | 1110/487 | C00042/C02170 | HMDB00254/HMDB00202 | 0.493851 | 0.968 | <0.001 | 0.0001 | 1.960** | Energy | Yes |
| Taurine | LC/MS pos | 1123 | C00245 | HMDB00251 | 1.653867 | 0.9972 | 0.2032 | 0.2598 | 0.603 | Amino Acid | Yes |
| Threonine | LC/MS pos | 6288 | C00188 | HMDB00167 | 5.380847 | 0.780656 | 0.0178 | 0.0392 | 0.145* | Amino Acid | Yes |
| Trimethylamine-N-oxide (TMAO) | LC/MS pos | 1146 | C00565 | HMDB00906 | 3.160464 | 1.040264 | 0.0117 | 0.0319 | 0.329* | Redox | No |
| Tryptamine | LC/MS pos | 1150 | C00398 | HMDB00303 | 1.583814 | 53.24717 | 0.0028 | 0.0133 | 33.6207** | Amino Acid | Yes |
| Tryptophan | LC/MS pos | 6305 | C00078 | HMDB00929 | 7.565738 | 0.73977 | 0.0104 | 0.0309 | 0.098* | Amino Acid | Yes |
| Tyramine | LC/MS pos | 5610 | C00483 | HMDB00306 | 0.148074 | 3.726405 | <0.001 | 0.0001 | 25.166** | Amino Acid | Yes |
| Tyrosine | LC/MS pos | 6057 | C00082 | HMDB00158 | 9.126862 | 0.632987 | 0.0056 | 0.0225 | 0.069* | Amino Acid | Yes |
| Uracil | LC/MS nag | 1174 | C00106 | HMDB00300 | 1.044215 | 2.825119 | 0.0299 | 0.0529 | 2.705** | Nucleotide | Yes |
| Urate | LC/MS neg | 1175 | C00366 | HMDB00289 | 2.842325 | 0.801884 | 0.0057 | 0.0225 | 0.282* | Nucleotide | Yes |
| Uridine | LC/MS pos | 6029 | C00299 | HMDB00296 | 3.811939 | 0.963101 | 0.0717 | 0.1114 | 0.253 | Nucleotide | Yes |
| Valine | LC/MS pos | 6287 | C00183 | HMDB00883 | 2.192665 | 1.277254 | 0.2555 | 0.3109 | 0.583 | Amino Acid | Yes |
| Xanthine | LC/MS nag | 1188 | C00385 | HMDB00292 | 0.987576 | 0.988861 | 0.9863 | 0.9863 | 1.001 | Nucleotide | Yes |
| Xanthurenate | LC/MS nag | 5699 | C02470 | HMDB00881 | 3.145443 | 0.755646 | 0.0026 | 0.0130 | 0.240* | Amino Acid | No |

**indicate metabolites that are higher in BV and statistically significant;
*indicates lower in BV and statistically significant;
italicized text indicates metabolites that are trending to significance.

Example 6

Validation Study (Cohort B)

An important question is whether metabolites identified by the global metabolic screen in the primary study (Cohort A) are reproducible in other samples using a different platform to measure the metabolites. Hence, in the validation study (Cohort B) a targeted set of metabolites that were identified as significant in the primary study including amino acids, amino acid catabolites, sialic acid, and eicosanoids 12-HETE and 13-HODE (Table 6) were evaluated. The validation cohort included 40 women with BV and 20 women without BV; BV was diagnosed by both Amsel criteria and Nugent score (Table 1). Of the 101 metabolites that were detected by the Northwest Metabolomics Research Center (NW-MRC) platform, 57 metabolites (56.4%) were significantly different between women with and without BV ($q<0.05$). Of the 57 metabolites, 37 were lower in BV (64.9%) and 20 were higher (35.1%). Most observations made in the primary study were confirmed in the validation study. Examples include lower levels of amino acids in BV, and this was significant for 16/20. Similarly, amino acid catabolites cadaverine ($p<0.001$), tyramine ($p<0.001$) and tryptamine ($p=0.003$) were higher in women with BV. The polyamine putrescine was higher in BV ($p<0.001$), while precursors arginine ($p=0.007$) and ornithine ($p=0.009$) were lower. N-aceytylneuraminate (sialic acid) ($p<0.001$) and succinate ($p<0.001$) were higher, and lactate was lower ($p<0.001$). Components of lipid metabolism, including higher levels of 12-HETE ($p=0.006$) and 13-HODE ($p=0.0004$), and lower levels of the 12-HETE precursor, arachidonate ($p=0.016$) were also corroborated. In some cases such as ascorbate ($p=0.775$) and oxidized glutathione ($p=0.162$), similar trends were observed in the primary and validation studies (both lower in BV), but fold change was not statistically significant in the validation study. Likewise, glucose was higher in women without BV ($p<0.001$), but not statistically significant in the primary study. Pipecolate was lower in BV ($p=0.018$) in the validation study, but found to be higher in BV in the primary study ($p<0.001$), and was associated with the presence of clue cells.

Figure 8:
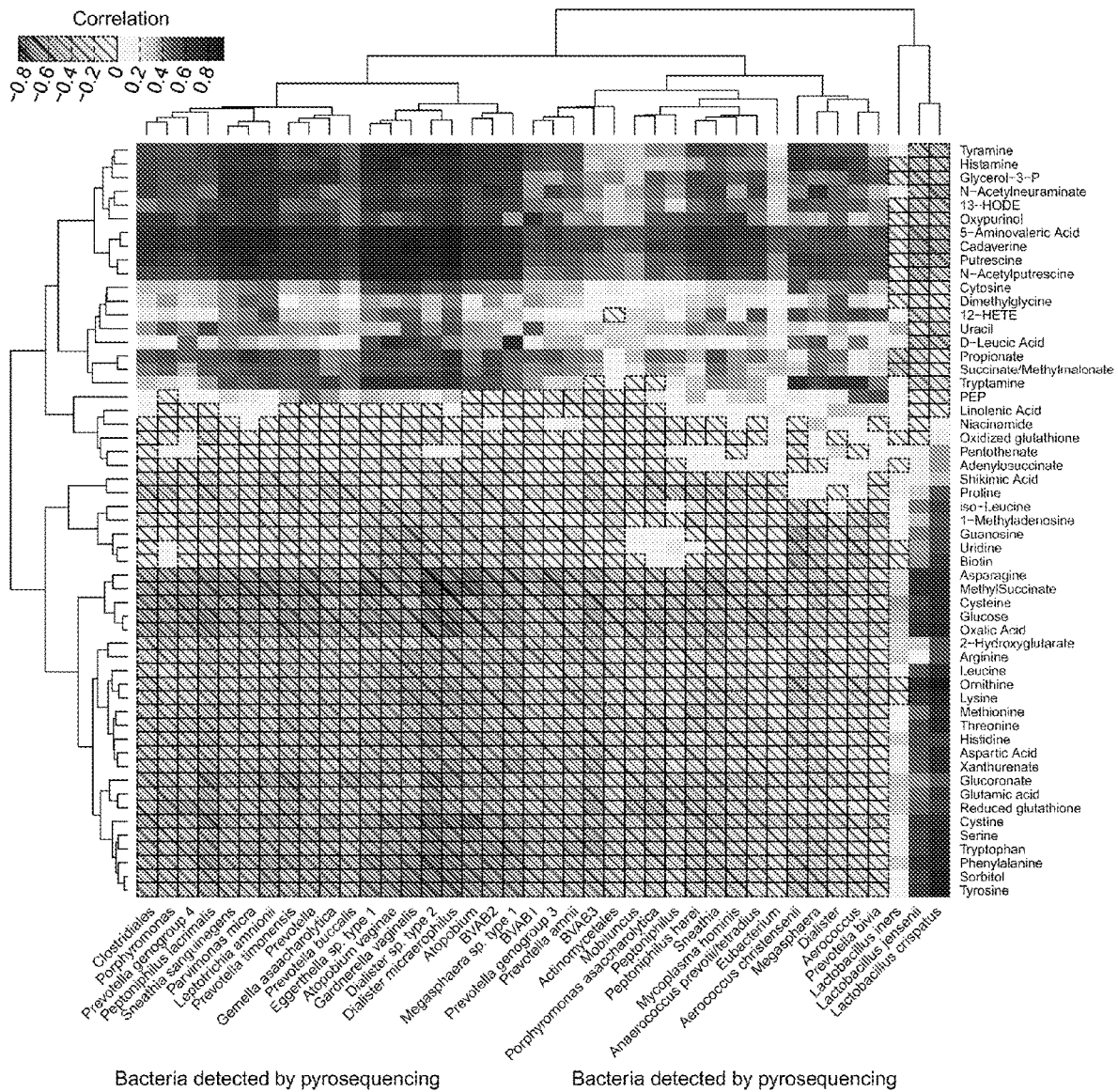
FIG. 8 depicts an association between metabolites and bacterial abundance in the validation study. Hierarchically clustered Pearson correlation coefficients demonstrate associations of vaginal bacteria detected by broad-range PCR and pyrosequencing (x-axis) with metabolites (y-axis, 50% of the most variable metabolites based on inter-quartile range, and 12-HETE, arginine, ornithine, N acetylneuraminate and succinate). Correlation values ranged from −0.86 to −0.86.
Figure 9:
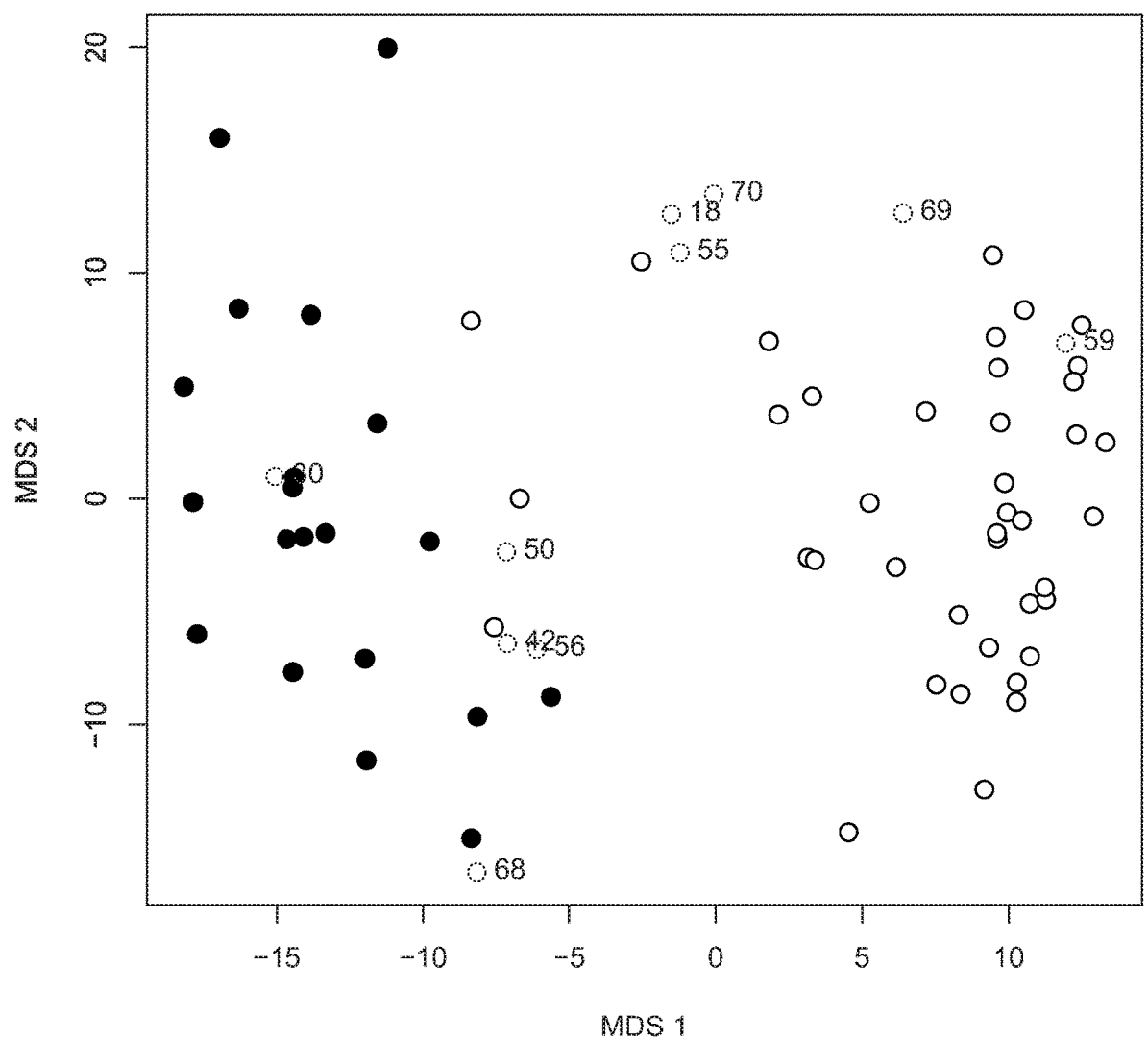

As in the primary study, Pearson correlation coefficients were used to link bacteria detected by broad-range PCR and pyrosequencing with the metabolites detected in the validation study (FIG. 8). BV-associated bacteria were highly correlated with metabolites associated with BV such as amino acid catabolites tyramine and histamine, polyamines putrescine and cadaverine, and fatty acids 13-HODE and 12-HETE. In contrast, the lactobacilli were correlated with intact amino acids and glucose among other metabolites. Clustering patterns were similar to that observed in the primary study with the BV associated bacteria clustering as two groups and the lactobacilli clustering together. *L. iners* exhibited correlation patterns that were intermediate between the BV-associated bacteria and the lactobacilli (FIG. 8).

Example 6

Summary

Research on the human microbiome has been largely focused on describing the composition of microbial communities under conditions of health and disease. Current knowledge of the functional properties of vaginal microbes is just emerging (30, 33). Small molecule metabolites (the metabolome) reflect the enzymatic pathways and complex metabolic networks that drive microbial transformation of host-derived products. The physiological state of the vagina was examined using approaches that integrate microbial community composition with metabolite profiles present in human vaginal fluid. First, metabolites present in vaginal fluid from women with and without BV were determined. Second, vaginal bacterial species was associated with metabolite concentrations using broad-range 16S rRNA gene PCR (to assess representation) as well as taxon directed qPCR (to measure bacterial concentrations). Third, metabolites were correlated with individual clinical criteria used to diagnose BV. And fourth, a set of select metabolites of interest that were identified in the primary study were validated by measuring them in a second set of samples using a different metabolomics platform.

There is a notable delineation of metabolite profiles in women with and without BV across multiple pathways (FIG. 1, Tables 1, 5, 6). The range and magnitude of these differences is striking. Within women with BV, there are at least two sub-types based on the metabolic profiles reflecting different concentrations rather than presence/absence of particular metabolites (FIG. 1). In a recent metabolomics study of eight women with symptomatic BV, clustering analysis resulted in two groups, differentiated by 48 metabolites (30). In the studies described in the Examples, 12/48 metabolites that were reported by Yeoman et al. were detected. Of the 12 metabolites, tryptophan, urea and valine contributed to the differences in the four clusters; the other 9 were not among the top 30% of most variable metabolites presented in FIG. 1. These data support previous studies that have demonstrated that BV is associated with high concentrations of putrescine and cadaverine, and low concentrations of lactate (2, 3, 5, 6, 23-27, 30, 34, 35). However, these data provide additional insight into the global changes in metabolite profiles in BV reflecting numerous pathways, particularly amino acid metabolism.

Lower levels of amino acids and higher levels of amino acid catabolites suggest increased utilization of amino acids in BV. Alternatively, lower amino acid levels in BV could be explained by decreased production of amino acids, but this would not explain the increase in amino acid decarboxylation products. Concomitant with lower levels of amino acids, there were lower levels of dipeptides as well, supporting increased catabolism (Tables 1 & 5). Specific BV-associated bacteria were correlated with presence of amino acid catabolites, whereas *L. crispatus* and *L. jensenii* were associated with the presence of intact amino acids and dipeptides. These data support the notion that BV-associated bacteria may use amino acids as a carbon and nitrogen source, in contrast to lactobacilli which are known to metabolize sugars such as glycogen. In line with these findings, another study that performed comparative analysis of *Lactobacillus* genomes from the human vagina suggested that *Lactobacillus* genomes were underrepresented in amino acid transport and metabolism, while being overrepresented for carbohydrate transport and metabolism (36). Furthermore, genome analysis of *L. iners* AB-1 showed that it lacks genes necessary for the de novo synthesis of amino acids with the possible exception of serine, and that approximately 15% of its genome is dedicated to various transport mechanisms, suggesting that it acquires metabolites such as amino acids crucial for survival from the environment (37). This is consistent with our observations that the metabolite profile of *L. iners* is intermediate to those of *L. crispatus*/*L. jensenii* and the BV-associated bacteria.

The amino acid arginine typically serves as a precursor for the generation of polyamines putrescine, spermidine and spermine. Lower arginine levels and higher putrescine levels in BV support conversion of arginine to putrescine. However, lower spermine and higher succinate levels suggest the presence of alternate pathways in BV (FIG. 6, Tables Si, S2). One possible explanation is that putrescine is converted to succinate via y-aminobutyrate (GABA), a novel alternate putrescine utilization pathway that was recently discovered in *E. coli* (38, 39), wherein putrescine is not converted to spermine. This is also supported by observations of higher levels of N-acetylputrescine in the study, which also leads to the formation of GABA (FIG. 6). Additional pathways may account for the higher levels of succinate in BV.

Carnitine, a product of lysine or methionine degradation, was lower in BV while levels of the precursor, deoxycarnitine, were high. One possible explanation for lower levels of carnitine is conversion to TMA by BV-associated bacteria, a process shown to be mediated by bacteria in the gut (40). TMA is produced from L-carnitine found in meat, and absorbed and converted to trimethylamine oxide (TMAO) in the liver. Production of TMAO can be inhibited by suppressing the intestinal microbiota using antibiotics, demonstrating another role for bacteria in TMA-TMAO metabolism. An alternate explanation for low carnitine in BV is that production is inhibited by lack of ascorbate, which is a necessary cofactor for synthesis.

There were significant alterations in lipid metabolism in BV. Higher levels of 12-HETE and lower levels of its precursor arachidonate in BV observed in both the primary and validation studies (Tables 1, 6) suggests conversion of arachidonate to 12-HETE by BV-associated bacteria. 12-HETE is a signaling eicosanoid that can mediate inflammatory response pathways, is a biomarker for inflammation (41-43) and is a fatty acid that serves membrane structural roles as a component of phospholipids (44). BVAB1 was negatively associated with 12-HETE (−0.028), while other BV-associated bacteria (measured by qPCR), were positively associated with 12-HETE (0.143 to 0.55). Interestingly, 12-HETE has been shown to be correlated with human parturition wherein 12-HETE levels are significantly elevated in laboring women (45). Furthermore, BV is associated with preterm birth (46, 47). Clearly, not all BV-associated bacteria are positively associated with 12-HETE, which suggests that the different sub-types of BV may be correlated with distinct risk factors.

The vaginal epithelium is in a reduced state in BV (48). Nonetheless, there are suggestions of perturbed redox homeostasis in BV, implying oxidative stress in this reduced environment. Reduced glutathione (GSH) to oxidized glutathione (GSSG) ratios are a good estimate of the redox environment; a decrease in GSH to GSSG ratio is suggestive of oxidative stress (49). The GSH/GSSG ratio in women without BV was found to be +3.29, and in BV was 0.23 in the primary study, and similar ratios were noted in the validation study (Table 6). GSH/GSSG ratios are critical in maintaining a reduced environment in the gut (50). All BV-associated bacteria (detected by qPCR) and *L. iners* were negatively correlated with presence of GSH. *L. crispatus* and *L. jensenii* were positively correlated with presence of GSH. In addition, GSH was negatively correlated with the presence of clue cells. Another metabolite indicative of oxidative stress is ascorbate (Vitamin C), a major antioxidant whose levels were significantly lower in BV. A third metabolite that may affect the redox status is spermine, whose concentrations are lower in BV. Spermine is present in semen and has antioxidant properties. Spermine is thought to protect spermatozoa, which contain high levels of polyunsaturated fatty acids that can be susceptible to reactive oxygen species (51). It is unclear why BV is associated with multiple metabolic indictors of oxidative stress when the environment is otherwise considered anaerobic and reduced. There is typically a lack of leukocytes in vaginal fluid from women with BV, so leukocytes are unlikely to contribute to the production of reactive oxygen species.

There were substantial changes in carbohydrate and energy metabolism in BV. One example includes higher levels of N-acetylneuraminate in vaginal fluid from women with BV (Table 1, 6). N acetylneuraminate is the most ubiquitous sialic acid, and is a component of glycoproteins, glycolipids and oligosaccharides (52). A recent study also observed increased quantities of N-acetylneuraminate in vaginal fluid from women with BV (53). There have been many reports of increased activity of sialidases in BV (54-57); sialidases hydrolyze N-acylneuraminic acid residues from oligosaccharides, glycoproteins and glycolipids. A point-of-care diagnostic test for BV that is currently available relies on the measurement of sialidase activity in vaginal fluids (58, 59). Importantly, high sialidase activity in BV has been associated with increased risks for preterm birth (55, 56, 60, 61). Glycoproteins such as mucins are present in mucus, and are reported to create a physical barrier between the host epithelium and bacteria (62, 63); this may be the source of the free N-acetylneuraminate present in vaginal fluid in BV. While little is known about the utilization of this metabolite by vaginal bacteria, a recent study showed that *G. vaginalis* has the metabolic machinery required for the transport and subsequent breakdown of N-acetylneuraminate as a carbon and energy source (53). Interestingly, N-acetylneuraminate has been shown to play a role in bacterial biofilms (64). Indeed, biofilms may play a role in BV, and *G. vaginalis* has been shown to be a key member of these biofilms (65-67). Interfering with production or liberation of N-acetylneuraminate in the vagina may be one approach to prevent BV if this metabolite plays a critical role in biofilm formation.

Figure 4A:
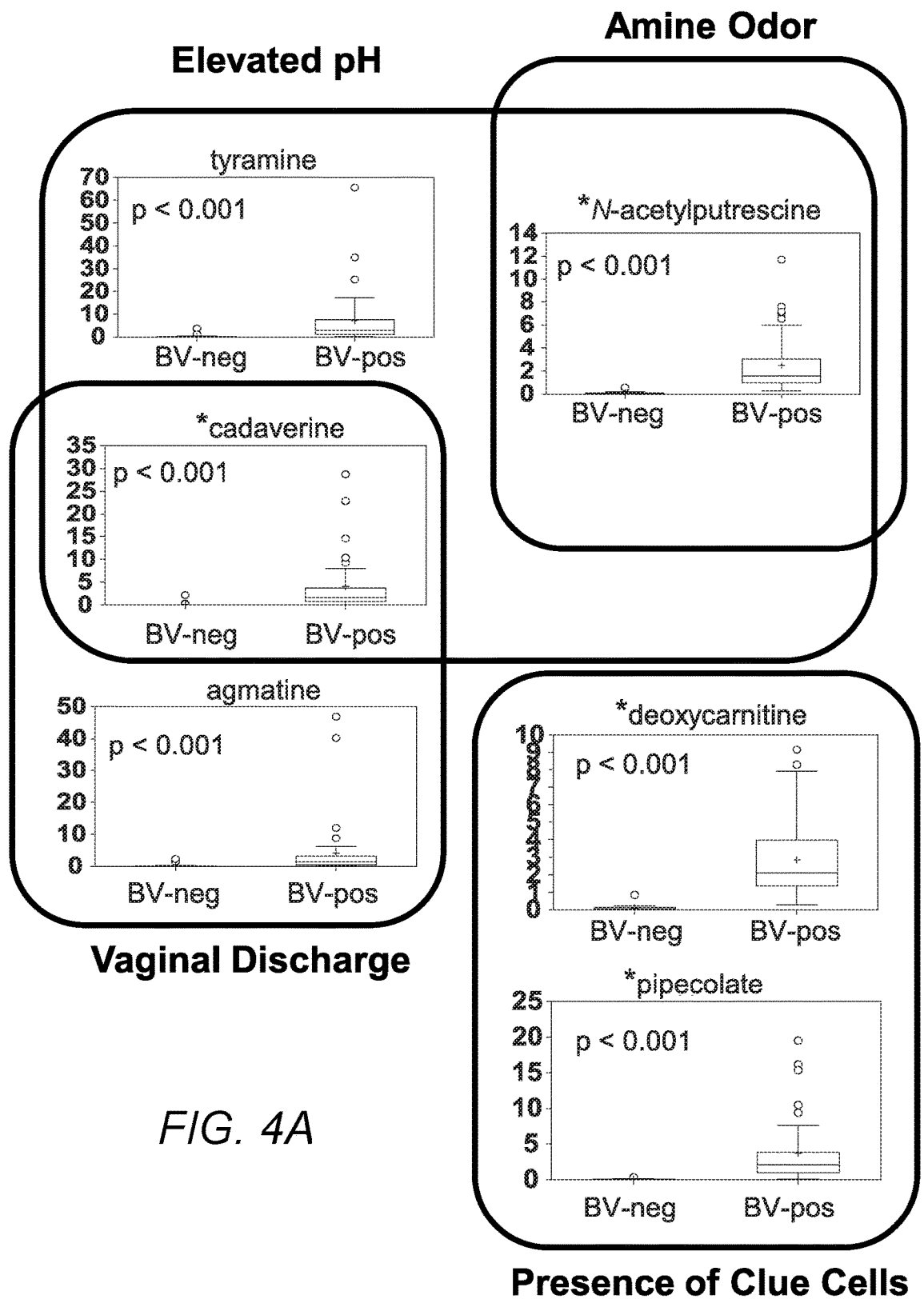
FIG. 4 is a model depicting metabolites associated with individual clinical criteria used in BV diagnosis (21). Stars denote metabolites that were positively or negatively associated with BV status. BV status is indicated on the x-axis of box plots. The y axis of box plots represent scaled concentrations of metabolites. The lines in box plots represent the mean and whiskers denote 95% confidence intervals.
Figure 4B:
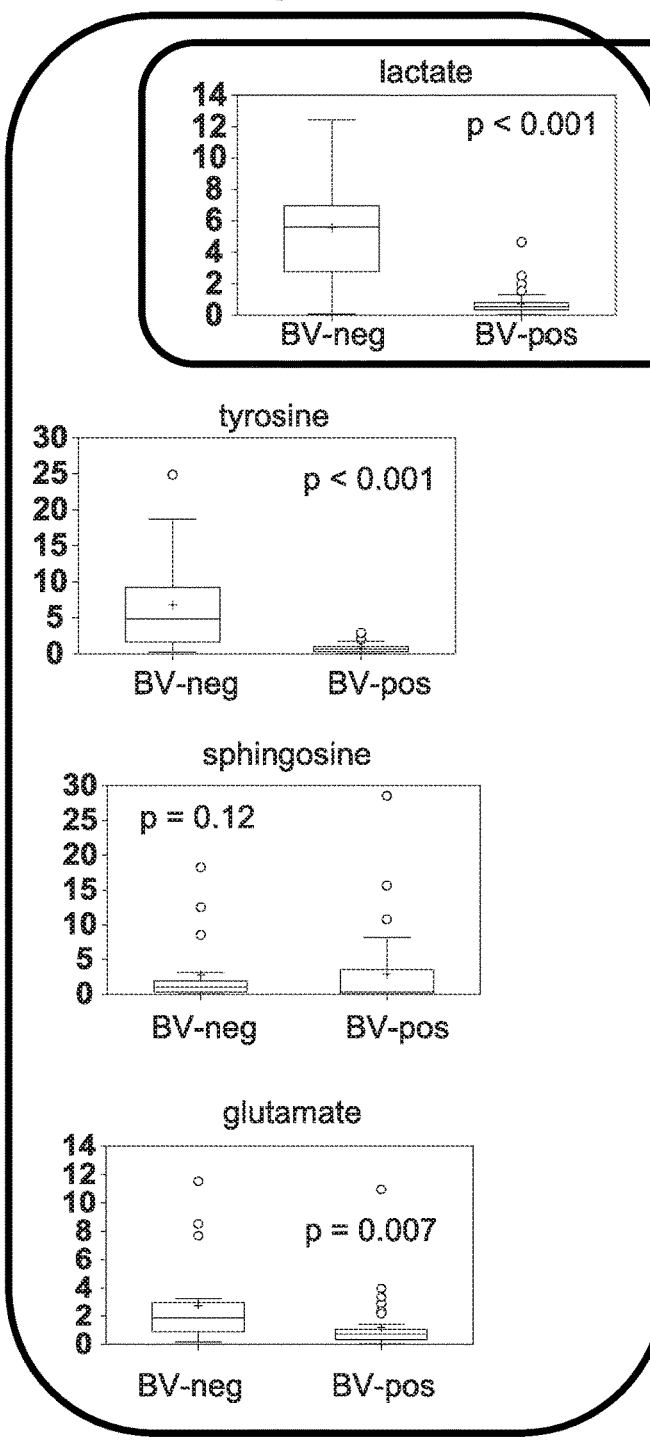
Figure 4B:
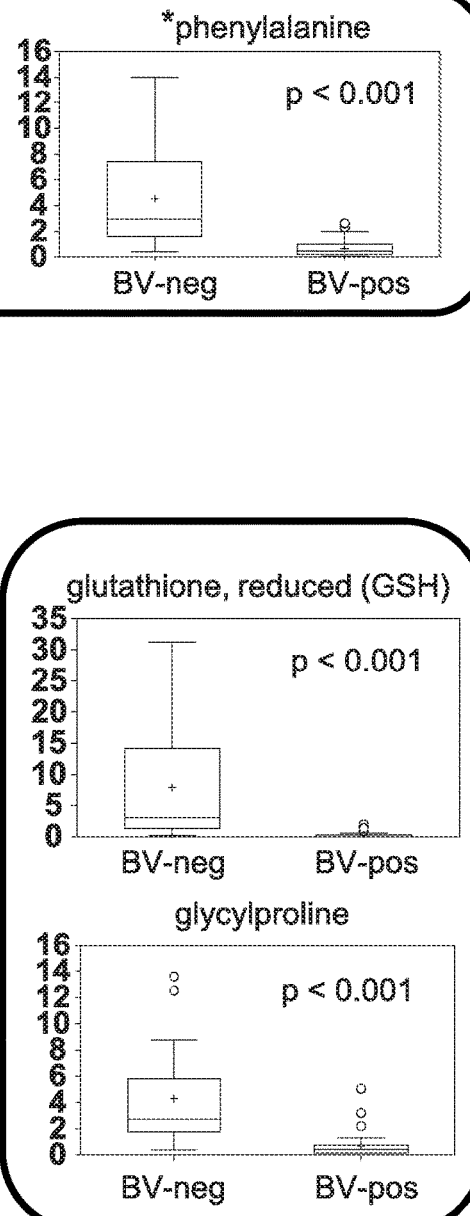

The studies confirm that women with BV had high levels of succinate and low levels of lactate. Consistent with this, BV-associated bacterial concentrations were positively correlated with succinate, while the lactobacilli were negatively correlated. Lactate was also negatively correlated with the presence of an amine odor and elevated pH, two criteria used in the clinical diagnosis of BV FIG. 4, Table 3).

Figure 10:
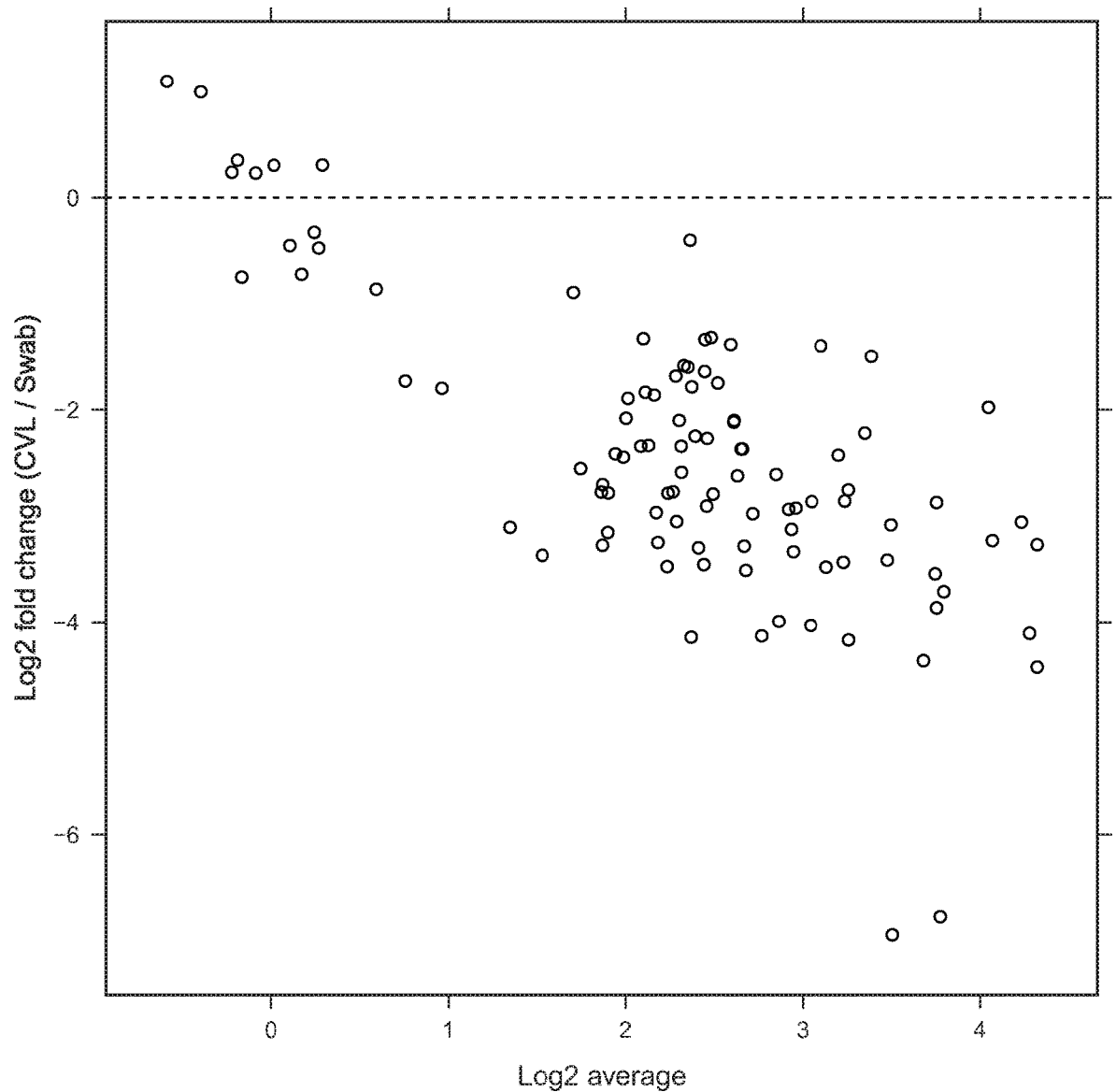
FIG. 10 depicts a comparison of metabolite concentrations in swab samples and CVL. A limited number of swab samples (n=8) were included in the validation study to determine the extent of dilution of metabolites in CVL samples.

Additional experiments as part of the validation studies were performed to address whether dilution in CVL impacts detection of particular metabolites and found that no metabolite was detected only in swab samples. As expected due to dilution, lower concentrations of metabolites were detected in CVL when compared with swabs (FIG. 10).

Metabolic signatures of BV are distinct and broad, consistent with dramatic changes in vaginal bacterial compositions. There are at least two metabolic sub-types in BV.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the invention. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

1. L Hillier S L. 1993. Diagnostic Microbiology of Bacterial Vaginosis. Am J Obstetrics Gynecology 169:455-459.
2. Ison C A, Easmon C S, Dawson S G, Southerton G, Harris J W. 1983. Non-volatile fatty acids in the diagnosis of non-specific vaginitis. J Clin Pathol 36:1367-1370.
3. Krohn M A, Hillier S L, Eschenbach D A. 1988. The diagnosis of bacterial vaginosis. Am J Epidemiol 128: 940-940.
4. Sobel J D. 2000. Bacterial vaginosis. Ann Rev Med 51:349-356.
5. Spiegel C A. 1991. Bacterial Vaginosis. Clin Microbiol Rev 4:485-502.
6. Spiegel C A, Amsel R, Eschenbach D, Schoenknecht F, Holmes K K. 1980. Anaerobic bacteria in nonspecific vaginitis. N Engl J Med 303:601-607.
7. Witkin S S, Ledger W J. 2012. Complexities of the uniquely human vagina Sci Transl Med: 132fs111.
8. Fredricks D N, Fiedler T L, Marrazzo J M. 2005, Molecular identification of bacteria associated with bacterial vaginosis. N Engl J Med 353:1899-1911.
9. Hillier S, Marrazzo J M, Holmes K K. 2008, Bacterial vaginosis, p. 737-768, In Holmes K K, Sparling P-A (ed.), Sexually transmitted diseases. McGraw-Hill, New York.
10. Ravel J, Gajer P, Abdo Z, Schneider G M, Koenig S S, McCulle S L, Karlebach S, Gork R, Russell J, Tacket C O, Brotman R M, Davis C C, Ault K, Peralta L, Forney Li. 2010. Microbes and Health Sackler Colloquium: Vaginal microbiome of reproductive-age women. Proc Natl Acad Sci USA. 108 Suppl 1:4680-4687.
11. Srinivasan S, Hoffman N G, Morgan M T, Matsen F A, Fiedler T L, Hall R W, Ross F J, McCoy C O, Bumgarner R, Marrazzo J M, Fredricks D N. 2012. Bacterial communities in women with bacterial vaginosis: high resolution phylogenetic analyses reveal relationships of microbiota to clinical criteria. PLoS One 7:Article No.: e37818.
12. Koumans E H, Sternberg M, Bruce C, McQuillan G, Kendrick J, Sutton M, Markowitz L E. 2007. The prevalence of bacterial vaginosis in the United States, 2001-2004; associations with symptoms, sexual behaviors, and reproductive health. Sex Transm Dis 34; 864-869.

13. Cherpes T L, Meyn L A, Krohn M A, Lurie J G, Hillier S L. 2003. Association between acquisition of herpes simplex virus type 2 in women and bacterial vaginosis, Clin Infect Dis 37:319-325.

14. Schwebke J R, Desmond R. 2005. Risk factors for bacterial vaginosis in women at high risk for sexually transmitted diseases. Sex Transm Dis 32:654-658.

15. Taha T E, Hoover D R, Dallabetta G A, Kumwenda N I, Mtimavalye L A, Yang L P, Liomba G N, Broadhead R L, Chiphangwi J D, Miotti P G. 1998. Bacterial vaginosis and disturbances of vaginal flora: association with increased acquisition of HIV. AIDS 12:1699-1706.

16. Cohen C R, Lingappa J R, Baeten J M, Ngayo M O, Spiegel C A, Hong T, Donnell D, Celum C, Kapiga S, Delany S, Bukusi E A. 2011 Bacterial vaginosis associated with increased risk of female-to-male HIV-1 transmission: A prospective cohort analysis among African Couples. PLoS Med 9:Article No: e1001251.

17. Hillier S L, Krohn M A, Cassen E, Easterling T R, Rabe L K, Eschenbach D A, 1995, The role of bacterial vaginosis and vaginal bacteria in amniotic-fluid infection in women in preterm labor with intact fetal membranes. Clin Infect Dis 20:S276-5278.

18. Haggerty C L, Hillier S L, Bass D C, Ness R B. 2004 Bacterial vaginosis and anaerobic bacteria are associated with endometritis. Clin Infect Dis 39:990-995.

19. Marrazzo J M, Wiesenfeld H C, Murray Pi, Busse B, Meyn L, Krohn M, Hillier S L. 2006 Risk factors for cervicitis among women with bacterial vaginosis J Infect Dis 193:617-624

20. Hummelen R, Fernandes A D, Macklaim J M, Dickson R J, Changalucha J, Gloor G B, Reid G. 2010. Deep sequencing of the vaginal microbiota of women with HIV. PLoS One 5:Article No.: e12078.

21. Amsel R, Totten P A, Spiegel C A, Chen K C, Eschenbach D, Holmes K K. 1983. Nonspecific vaginitis: diagnostic criteria and microbial and epidemiologic associations, Am J Med 74:14-22.

22. Nugent R P, Krohn M A, Hillier S L. 1991. Reliability of diagnosing bacterial vaginosis is improved by a standardized method of Gram stain interpretation. J Clin Microbiol 29; 297-301.

23. Chen K C, Forsyth P S, Buchanan T M, Holmes K K. 1979. Amine content of vaginal fluid from untreated and treated patients with nonspecific vaginitis. J Clin Invest 63:828-835.

24. Sobel J D, Karpas Z, Lorber A. 2012. Diagnosing vaginal infections through measurement of biogenic amines by ion mobility spectrometry. Eur J Obstet, Gynecol, Reprod Biol 163:81-84.

25. Wolrath H, Forsum U, Larsson P G, Boren H. 2001. Analysis of bacterial vaginosis-related amines in vaginal fluid by gas chromatography and mass spectrometry, J Clin Microbiol 39:4026-4031.

26. Chen K C, Amsel R, Eschenbach D A, Holmes K K. 1982. Biochemical diagnosis of vaginitis: determination of diamines in vaginal fluid. J Infect Dis 145:337-345.

27. Brand J M, Galask R P. 1986. Trimethyla mine: the substance mainly responsible for the fishy odor often associated with bacterial vaginosis. Obstet Gynecol 68:682-685.

28. Giacomini G, Calcinai A, Moretti D, Cristofani R. 1998. Accuracy of cervical/vaginal cytology in the diagnosis of bacterial vaginosis. Sex Transm Dis 25:24-27.

29. Pheifer T A, Forsyth P S, Durfee M A, Pollock H M, Holmes K K. 1978. Nonspecific vaginitis: role of *Haemophilus vaginalis* and treatment with metronidazole, N Engl J Med 298:1429-1434, 30. Yeoman C J, Thomas S M, Miller M E, Ulanov A V, Torralba M, Lucas S, Gillis M, Cregger M, Gomez A, Ho M, Leigh S R, Stumpf R, Creedon D J, Smith M A, Weisbaum J S, Nelson K E, Wilson B A, White B A. 2013, A multi-omic systems-based approach reveals metabolic markers of bacterial vaginosis and insight into the disease, PLoS One 8:e56111, Fredricks D N, Fiedler T L, Thomas K K, Oakley B B, Marrazzo J M. 2007. Targeted PCR for detection of vaginal bacteria associated with bacterial vaginosis. J Clin Microbiol 45:3270-3276.

32. Marrazzo J M, Thomas K K, Fiedler T L, Ringwood K, Fredricks D N. 2008. Relationship of specific vaginal bacteria and bacterial vaginosis treatment failure in women who have sex with women. Ann Intern Med 149:20-28.

33. Abubucker S, Segata N, Coll J, Schubert A M, Izard J, Cantarel B L, Rodriguez-Mueller B, Zucker J, Thiagarajan M, Henrissat B, White 0, Kelley S T, Methe B, Schloss P D, Gevers D, Mitreva M, Huttenhower C. 2012, Metabolic reconstruction for metagenomic data and its application to the human microbiome. PLoS Comp Biol 8:e1002358.

34. Gajer P, Brotman R M, Bai G, Sakamoto J, Schuette U M E, Zhong X, Koenig S S K, Fu L, Ma Z, Zhou X, Abdo Z, Forney U, Ravel J. 2012, Temporal dynamics of the human vaginal microbiota, Sci Transl Med 4:Article No.: 132ra152.

35. Wolrath H, Boren H, Hallen A, Forsum U. 2002. Trimethylamine content in vaginal secretion and its relation to bacterial vaginosis. APMIS 110:819-824.

36. Mendes-Soares H, Suzuki H, Hickey R J, Forney U. 2014. Comparative functional genomics of *Lactobacillus* spp, reveals possible mechanisms for specialization of vaginal lactobacilli to their environment. J Bacteriol 196: 1458-1470.

37. Macklaim J M, Gloor G B, Anukam K C, Cribby S, Reid G. 2011. At the crossroads of vaginal health and disease, the genome sequence of *Lactobacillus iners* AB-1. Proc Natl Aca Sci USA 108:4688-4695

38. Kurihara S, Kato K, Asada K, Kumagai H, Suzuki H, 2010. A putrescine-inducible pathway comprising PuuE-Ynel in which gamma-aminobutyrate Is degraded into succinate in *Escherichia coli* K-12. J Bacteriol 192:4582-4591.

39. Kurihara S, Oda S, Kato K, Kim H G, Koyanagi T, Kumagai H, Suzuki H, 2005, A novel putrescine utilization pathway involves gamma-glutamylated intermediates of *Escherichia coli* K-12, J Blot Chem 280:4602-4608.

40. Koeth R A, Wang Z, Levison B S, Buffa J A, Org E, Sheehy B T, Britt E B, Fu X, Wu Y, Li L, Smith J D, DiDonato J A, Chen J, Li H, Wu G D, Lewis J D, Warner M, Brown J M, Krauss R M, Tang W H W, Bushman F D, Lusis A J, Hazen S L. 2013. Intestinal microbiota metabolism of L-carnitine, a nutrient in red meat, promotes atherosclerosis. Nat Med 19:576-585.

41. Conners M S, Stoltz R A, Dunn M W, Abraham N G, Schwartzman M L. 1994. Cytochrome P450 monooxygenase and lipoxygenase are important in generating a powerful stereospecific inflammatory eicosanoid in the corneal epithelium, Invest Ophth Vis Sci 35:1944.

42. Cunningham F M, Woollard P M, Camp R D, 1985, Proinflammatory properties of unsaturated fatty acids and their monohydroxy metabolites. Prostaglandins 30:497-509.
43. Stoltz R A, Conners M S, Dunn M W, Schwartzmann M L. 1994. Effect of metabolic inhibitors on arachidonic acid metabolism in the corneal epithelium: Evidence for cytochrome P450-mediated reactions. J Ocul Pharmacol 10:307-317.
44. Spector A A. 1999. Essentiality of fatty acids. Lipids 34 Suppl:S1-3.
45. Romero R, Emamian M, Wan M, Grzyboski C, Hobbins J C, Mitchell M D. 1987. Increased concentrations of arachidonic acid lipoxygenase metabolites in amniotic fluid during parturition. Obstet Gynecol 70:849-851.
46. Hillier S L, Nugent R P, Eschenbach D A, Krohn M A, Gibbs R S, Martin D H, Cotch M F, Edelman R, Pastorek J G, Rao A V, McNellis D, Regan J A, Carey J C, Klebanoff M A. 1995. Association between bacterial vaginosis and preterm delivery of a low-birth-weight infant. N Engl J Med 333:1737-1742
47. Klebanoff M A, Hillier S L, Nugent R P, MacPherson C A, Hauth J C, Carey J C, Harper M, Wapner R J, Trout W, Moawad A, Leveno K J, Miodovnik M, Sibai B M, VanDorsten J P, Dombrowski M P, O'Sullivan M J, Varner M, Langer 0. 2005. Is bacterial vaginosis a stronger risk factor for preterm birth when it is diagnosed earlier in gestation? Am J Obstet Gynecol 192:470-477.
48. Holmes K K, Chen K C S, Lipinski C M, Eschenbach D A. 1985. Vaginal redox potential in bacterial vaginosis (Nonspecific Vaginitis). J Infect Dis 152:379-382.
49. Kemp M, Go Y M, Jones D P. 2008. Nonequilibrium thermodynamics of thiol/disulfide redox systems: a perspective on redox systems biology. Free Rad Bio Med 44:921-937.
50. Circu M L, Aw T V. 2011. Redox biology of the intestine. Free Radical Res 45:1245-1266.
51. Henkel R R. 2011. Leukocytes and oxidative stress: dilemma for sperm function and male fertility. Asian Journal Androl 13:43-52.
52. Apicella M A, Jones P A. 2005. Sialylation of the Gram-negative bacterial cell surface, p. 73-85 In Nataro J P, Cohen P S, Mobley H L T, Weiser J N (ed.), Colonization of mucosal surfaces. ASM Press, Washington, D.C.
53. Lewis W G, Robinson L S, Gilbert N M, Perry J C, Lewis A L. 2013. Degradation, foraging, and depletion of mucus sialoglycans by the vagina-adapted Actinobacterium *Gardnerella vaginalis*. J Biol Chem 288:12067-12079.
54. Briselden A M, Moncla B J, Stevens C E, Hillier S L. 1992. Sialidases (Neuraminidases) in bacterial vaginosis and bacterial vaginosis-associated microflora. J Clin Microbiol 30:663-666.
55. Cauci S, Culhane J F. 2011. High sialidase levels increase preterm birth risk among women who are bacterial vaginosis-positive in early gestation. Am J Obstet Gynecol 204:142 e141-149.
56. McGregor J A, French J I, Jones W, Milligan K, McKinney P, Patterson E, Parker R. 1994. Bacterial vaginosis is associated with prematurity and vaginal fluid mucinase and sialidase—results of a controlled trial of topical clindamycin cream. Am J Obstet Gynecol 170:1048-1060.
57. Olmsted S S, Meyn L A, Rohan L C, Hillier S L. 2003. Glycosidase and proteinase activity of anaerobic gram-negative bacteria isolated from women with bacterial vaginosis. Sex Transm Dis 30:257-261.
58. Myziuk L, Romanowski B, Johnson S C. 2003. BVBlue test for diagnosis of bacterial vaginosis. J Clin Microbiol 41:1925-1928.
59. Wiggins R, Crowley T, Horner P J, Soothill P W, Millar M R, Corfield A P. 2000. Use of 5-bromo-4-chloro-3-indolyl-alpha-D-N-acetylneuraminic acid in a novel spot test to identify sialidase activity in vaginal swabs from women with bacterial vaginosis. J Clin Microbiol 38:3096-3097.
60. Cauci S, Hitti J, Noonan C, Agnew K, Quadrifoglio F, Hillier S L, Eschenbach D A. 2002. Vaginal hydrolytic enzymes, immunoglobulin A against *Gardnerella vaginalis* toxin, and risk of early preterm birth among women in preterm labor with bacterial vaginosis or intermediate flora. Am Journal Obstet Gynecol 187:877-881.
61. Cauci S, Thorsen P, Schendel D E, Bremmelgaard A, Quadrifoglio F, Guaschino S. 2003. Determination of immunoglobulin A against *Gardnerella vaginalis* hemolysin, sialidase, and prolidase activities in vaginal fluid: Implications for adverse pregnancy outcomes. J Clin Microbiol 41:435-438.
62. Moran A P, Gupta A, Joshi L. 2011. Sweet-talk: role of host glycosylation in bacterial pathogenesis of the gastrointestinal tract. Gut 60:1412-1425.
63. Slomiany B L, Murty V L, Piotrowski J, Slomiany A. 1996. Salivary mucins in oral mucosal defense. Gen Pharmacol 27:761-771.
64. Greiner L L, Watanabe H, Phillips N J, Shao J, Morgan A, Zaleski A, Gibson B W, Apicella M A. 2004. Nontypeable *Haemophilus influenzae* strain 2019 produces a biofilm containing N-acetylneuraminic acid that may mimic sialylated O-linked glycans. Infect Immunity 72:4249-4260.
65. Srinivasan S, Fredricks D N. 2008. The human vaginal bacterial biota and bacterial vaginosis. Interdiscip Perspect Infect Dis 2008:750479.
66. Swidsinski A, Mendling W, Loening-Baucke V, Ladhoff A, Swidsinski S, Hale L P, Lochs H. 2005. Adherent biofilms in bacterial vaginosis. Obstet Gynecol 106:1013-1023.
67. Swidsinski A, Mendling W, Loening-Baucke V, Swidsinski S, Dorffel Y, Scholze J, Lochs H, Verstraelen H. 2008. An adherent *Gardnerella vaginalis* biofilm persists on the vaginal epithelium after standard therapy with oral metronidazole. Am J Obstet Gynecol 198:97 e91-96.
68. Khot P D, Ko D L, Hackman R C, Fredricks D N. 2008. Development and optimization of quantitative PCR for the diagnosis of invasive aspergillosis with bronchoalveolar lavage fluid. BMC Infect Dis 8:73.
69. Fredricks D N, Fiedler T L, Thomas K K, Mitchell C M, Marrazzo J M. 2009. Changes in vaginal bacterial concentrations with intravaginal metronidazole therapy for bacterial vaginosis as assessed by quantitative PCR. J Clin Microbiol 47:721-726.
70. Srinivasan S, Liu C, Mitchell C M, Fiedler T L, Thomas K K, Agnew K J, Marrazzo J M, Fredricks D N. 2010. Temporal variability of human vaginal bacteria and relationship with bacterial vaginosis. PLoS One 5:e10197.
71. Matsen F A, Kodner R B, Armbrust E V. 2010. pplacer: linear time maximum-likelihood and Bayesian phylogenetic placement of sequences onto a fixed reference tree. BMC Bioinform 11:538.
72. Evans A M, DeHaven C D, Barrett T, Mitchell M, Milgram E. 2009. Integrated, nontargeted ultrahigh performance liquid chromatography/electrospray ionization tandem mass spectrometry platform for the identification and relative quantification of the small-molecule complement of biological systems. Anal Chem 81:6656-6667.
73. Lawton K A, Berger A, Mitchell M, Milgram K E, Evans A M, Guo L, Hanson R W, Kalhan S C, Ryals J A, Milburn M V. 2008. Analysis of the adult human plasma metabolome. Pharmacogenomics 9:383-397.
74. Ohta T, Masutomi N, Tsutsui N, Sakairi T, Mitchell M, Milburn M V, Ryals J A, Beebe K D, Guo L. 2009. Untargeted metabolomic profiling as an evaluative tool of fenofibrate-induced toxicology in Fischer 344 male rats. Toxicol Pathol 37:521-535.
75. R Core Team 2013. R: A language and environment for statisitical computing. R Foundation for Statistical Computing, Vienna Austria. URL http://www.R-project.org/76.
76. Friedman J, Hastie T, Tibshirani R. 2010. Regularization paths for generalized linear models via coordinate descent. J Stat Softw 33:1-22.

The invention claimed is:

1. A method of diagnosing and treating bacterial vaginosis in a subject, the method comprising:
   collecting a sample from the subject;
   assessing a small molecule metabolomic profile by measuring levels of indicative metabolites comprising at least two of:
      a metabolite associated with the presence of clue cells;
      a metabolite associated with the presence of amine odors; and
      a metabolite associated with vaginal discharge;
   comparing the small molecule metabolomic profile with a diagnostic metabolomic profile;
   determining that there is a match between the small molecule metabolomic profile and the diagnostic metabolomic profile of at least 50%, the match being indicative of bacterial vaginosis; and
   administering an antibiotic treatment to the subject.

2. The method of claim 1 wherein the sample is vaginal fluid or Cervicovaginal lavage fluid (CVL).

3. The method of claim 1 wherein the method comprises Chromatographic separation and mass spectroscopy.

4. The method of claim 1 wherein the indicative metabolites comprise one or more metabolites selected from the group consisting of: lipids, amino acids, nucleotides, cofactors, vitamins, carbohydrates, energy molecules and redox molecules.

5. The method of claim 1 wherein the indicative metabolites comprise:
   one or more fatty acids selected from the group consisting of 13-HODE, 12-HETE, Glycerol-3-P, Arachidonate, Carnitine;
   one or more nucleotides selected from the group consisting of Oxypurinol, Uracil, Adenosine, AMP, Hypoxanthine, and Urate; or
   one or more carbohydrates selected from the group consisting of Glyceraldehyde, N-Acetylneuraminate, PEP, F16BP/F26BP/G16BP, Glucoronate, Glucose, Glutamic acid, Lactate, Oxalic Acid, and Sorbitol.

6. The method of claim 1 wherein the match between the small molecule metabolomic profile and the diagnostic metabolomic profile is at least 80%.

7. A method of monitoring disease progression and treating bacterial vaginosis in a subject, the method comprising
collecting a first sample from the subject at a first time;
assessing a first small molecule metabolomic profile by measuring levels of indicative metabolites comprising at least two of:
a metabolite associated with the presence of clue cells;
a metabolite associated with the presence of amine odors; and
a metabolite associated with vaginal discharge;
comparing the first small molecule metabolomic profile with a diagnostic metabolomic profile;
determining that there is a first match between the first small molecule metabolomic profile and the diagnostic metabolomic profile of at least 50%, the first match being indicative of bacterial vaginosis;
collecting a second sample from the subject at a second time that is after the first time;
assessing a second small molecule metabolomic profile by measuring levels of the indicative metabolites;
comparing the second small molecule metabolomic profile with the diagnostic metabolomic profile;
determining that there is a second match between the second small molecule metabolomic profile and the diagnostic metabolomic profile of at least 50%;
determining disease progression of the bacterial vaginosis based at least in part on the first and second matches; and
administering an antibiotic treatment to the subject.

8. The method of claim 7 wherein the period of time between the first time and the second time is at least three days.

9. The method of claim 7 wherein the first sample, the second sample, or both are vaginal fluid or Cervicovaginal lavage fluid (CVL).

10. The method of claim 1, wherein the metabolite associate with the presence of clue cells is Deoxycarnitine or Pipecolate.

11. The method of claim 1, wherein the metabolite associated with the presence of amine odors is N-acetylputrescine.

12. The method of claim 1, wherein the metabolite associated with vaginal discharge is Agmatine or Cadaverine.

13. The method of claim 1, wherein the indicative metabolites further comprise Tyramine, Tryptamine, 5-aminovalerate, 4-hydroxybutyrate, or a combination thereof.

14. The method of claim 1, wherein:
the metabolite associate with the presence of clue cells is Deoxycarnitine or Pipecolate;
the metabolite associated with the presence of amine odors is N-acetylputrescine; and
the metabolite associated with vaginal discharge is Agmatine or Cadaverine.

15. The method of claim 7, wherein the metabolite associate with the presence of clue cells is Deoxycarnitine or Pipecolate.

16. The method of claim 7, wherein the metabolite associated with the presence of amine odors is N-acetylputrescine.

17. The method of claim 7, wherein the metabolite associated with vaginal discharge is Agmatine or Cadaverine.

18. The method of claim 7, wherein the indicative metabolites further comprise Tyramine, Tryptamine, 5-aminovalerate, 4-hydroxybutyrate, or a combination thereof.

* * * * *